(12) United States Patent
Kahne et al.

(10) Patent No.: US 9,573,911 B2
(45) Date of Patent: Feb. 21, 2017

(54) DIPHOSPHATE MIMETICS AND USES THEREOF

(75) Inventors: Suzanne Walker Kahne, Brookline, MA (US); Jiaoyang Jiang, Boston, MA (US); Michael Block Lazarus, West Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 252 days.

(21) Appl. No.: 14/131,024

(22) PCT Filed: Jul. 6, 2012

(86) PCT No.: PCT/US2012/045675
§ 371 (c)(1),
(2), (4) Date: Feb. 25, 2014

(87) PCT Pub. No.: WO2013/006758
PCT Pub. Date: Jan. 10, 2013

(65) Prior Publication Data
US 2014/0163079 A1    Jun. 12, 2014

Related U.S. Application Data

(60) Provisional application No. 61/504,958, filed on Jul. 6, 2011, provisional application No. 61/584,443, filed on Jan. 9, 2012.

(51) Int. Cl.
*C07D 263/58* (2006.01)
*A61K 45/06* (2006.01)

(52) U.S. Cl.
CPC ............. *C07D 263/58* (2013.01); *A61K 45/06* (2013.01)

(58) Field of Classification Search
None
See application file for complete search history.

(56) References Cited

U.S. PATENT DOCUMENTS

| | | |
|---|---|---|
| 8,524,444 B2 | 9/2013 | Gross et al. |
| 8,957,075 B2 | 2/2015 | Kahne et al. |
| 8,993,718 B2 | 3/2015 | Gross et al. |
| 2002/0128235 A1 | 9/2002 | Konrad et al. |
| 2003/0186948 A1 | 10/2003 | Kudlow et al. |
| 2004/0191811 A1 | 9/2004 | Burghardt et al. |
| 2004/0259910 A1 | 12/2004 | Bolin et al. |
| 2005/0026266 A1 | 2/2005 | Clausen et al. |
| 2005/0032145 A1 | 2/2005 | Burghardt et al. |
| 2005/0113407 A1 | 5/2005 | Bolin et al. |
| 2005/0113436 A1 | 5/2005 | Elokdah et al. |
| 2005/0250678 A1 | 11/2005 | DeFrees et al. |
| 2006/0099688 A1 | 5/2006 | Clausen et al. |
| 2007/0027068 A1 | 2/2007 | DeFrees et al. |
| 2009/0163545 A1 | 6/2009 | Goldfarb |
| 2009/0325944 A1 | 12/2009 | Kahne et al. |
| 2010/0290987 A1 | 11/2010 | Gross et al. |
| 2012/0108605 A1 | 5/2012 | Kahne et al. |
| 2014/0187444 A1 | 7/2014 | Gross et al. |

FOREIGN PATENT DOCUMENTS

| | | | |
|---|---|---|---|
| CH | 570990 A | | 12/1975 |
| CH | 572305 A | | 2/1976 |
| DE | 2210419 | * | 2/1974 |
| FR | 2179293 A5 | | 11/1973 |
| GB | 1330611 A | | 9/1973 |
| WO | WO 2007/120638 A2 | | 10/2007 |
| WO | WO 2008/057933 A2 | | 5/2008 |
| WO | WO 2008/156676 A1 | | 12/2008 |
| WO | WO 2009/086952 A1 | | 7/2009 |
| WO | WO 2010/141074 A2 | | 12/2010 |
| WO | PCT/US2012/045675 | | 11/2012 |
| WO | WO 2013/006758 A1 | | 1/2013 |
| WO | PCT/US2012/045675 | | 1/2014 |

OTHER PUBLICATIONS

Ninkovic et al., O-glycosylated human MUC1 repeats are processed in vitro by immunoproteasomes. J Immunol. Aug. 15, 2007;179(4):2380-8.
International Search Report and Written Opinion for PCT/US2012/045675, mailed Nov. 22, 2012.
International Preliminary Report on Patentability for PCT/US2012/045675, mailed Jan. 16, 2014.
Akimoto et al., Elevated expression of O-GlcNAc-modified proteins and O-GlcNAc transferase in corneas of diabetic Goto-Kakizaki rats. Invest Ophthalmol Vis Sci. Sep. 2003;44(9):3802-9.
Alexander et al., Mechanism of carbamate inactivation of FAAH: implications for the design of covalent inhibitors and in vivo functional probes for enzymes. Chem Biol. Nov. 2005;12(11):1179-87.
Andres et al., 4-Thiazolidinones: novel inhibitors of the bacterial enzyme MurB. Bioorg Med Chem Lett. Apr. 17, 2000;10(8):715-7.
Brown et al., Glycan antagonists and inhibitors: a fount for drug discovery. Crit Rev Biochem Mol Biol. Nov.-Dec. 2007;42(6):481-515.
Cline et al., Effects of a novel glycogen synthase kinase-3 inhibitor on insulin-stimulated glucose metabolism in Zucker diabetic fatty (fa/fa) rats. Diabetes. Oct. 2002;51(10):2903-10.

(Continued)

*Primary Examiner* — Kamal Saeed
(74) *Attorney, Agent, or Firm* — Wolf, Greenfield & Sacks, P.C.

(57) ABSTRACT

The present invention provides compounds of Formulae (I)-(V), pharmaceutically acceptable salts thereof, and pharmaceutical compositions thereof. In one aspect, compounds of the present invention are useful as glycosyltransferase inhibitors, in particular, O-linked N-acetylglucosamine (O-GlcNAc) transferase (OGT) inhibitors. In another aspect, compounds of the present invention are useful as kinase inhibitors, in particular, PLK1 inhibitors, GSK3β inhibitors, or MAPKAPK2 inhibitors. The present invention further provides methods of using the inventive compounds, e.g., as biological probes to study the inhibition of OGT and/or kinase activity and as therapeutics, e.g., for the treatment of OGT-associated and/or kinase-associated conditions.

21 Claims, 15 Drawing Sheets

(56) References Cited

OTHER PUBLICATIONS

Compain et al., Carbohydrate mimetics-based glycosyltransferase inhibitors. Bioorg Med Chem. Dec. 2001;9(12):3077-92.

Compain et al., Design, synthesis and biological evaluation of iminosugar-based glycosyltransferase inhibitors. Curr Top Med Chem. 2003;3(5):541-60.

Dorfmueller et al., Cell-penetrant, nanomolar O-GlcNAcase inhibitors selective against lysosomal hexosaminidases. Chem Biol. Nov. 24, 2010;17(11):1250-5.

Dorfmueller et al., GlcNAcstatin: a picomolar, selective O-GlcNAcase inhibitor that modulates intracellular O-glcNAcylation levels. J Am Chem Soc. Dec. 27, 2006;128(51):16484-5.

Dorfmueller et al., Substrate and product analogues as human O—GlcN Ac transferase inhibitors. Amino Acids. Mar. 2011;40(3):781-92. Epub Jul. 17, 2010.

Frantom et al., UDP-(5F)-GlcNAc acts as a slow-binding inhibitor of MshA, a retaining glycosyltransferase. J Am Chem Soc. May 19, 2010;132(19):6626-7.

Gao et al., Dynamic O-glycosylation of nuclear and cytosolic proteins: cloning and characterization of a neutral, cytosolic beta-N-acetylglucosaminidase from human brain. J Biol Chem. Mar. 30, 2001;276(13):9838-45. Epub Jan. 8, 2001.

Gloster et al., Glycosidase inhibition: assessing mimicry of the transition state. Org Biomol Chem. Jan. 21, 2010;8(2):305-20. Epub Nov. 5, 2009.

Gould et al., Glycogen synthase kinase-3: a putative molecular target for lithium mimetic drugs. Neuropsychopharmacology. Jul. 2005;30(7):1223-37.

Gross et al., A strategy to discover inhibitors of O-linked glycosylation. J Am Chem Soc. Jan. 16, 2008;130(2):440-1. Epub Dec. 20, 2007.

Gross et al., Discovery of O-GlcNAc transferase inhibitors. J Am Chem Soc. Oct. 26, 2005;127(42):14588-9.

Hadjuch et al., A convenient synthesis of the C-1-phosphonate analogue of UDP-GlcNAc and its evaluation as an inhibitor of O-linked GlcNAc transferase (OGT). Carbohydr Res. Feb. 4, 2008;343(2):189-95. Epub Nov. 1, 2007.

Hagen et al., All in the family: the UDP-GalNAc:polypeptide N-acetylgalactosaminyltransferases. Glycobiology. 2003;13(1):1R-16R.

Hanover, Glycan-dependent signaling: O-linked N-acetylglucosamine FASEB J. Sep. 2001;15(11):1865-76.

Hart et al., Chapter 18. The O-GlcNAc modification. In: Essentials of glycobiology. Varki et al., eds. Cold Spring Harbor Laboratory Press, Cold Spring Harbor, Ny. 2009. 21 pages.

Helm et al., Identification of active-site inhibitors of MurG using a generalizable, high-throughput glycosyltransferase screen. J Am Chem Soc. Sep. 17, 2003;125(37):11168-9.

Hooper et al., The GSK3 hypothesis of Alzheimer's disease. J Neurochem. Mar. 2008;104(6):1433-9. Epub Dec. 18, 2007.

Hu et al., Identification of selective inhibitors for the glycosyltransferase MurG via high-throughput screening. Chem Biol. May 2004;11(5):703-11.

Hurtado-Guerrero et al., Molecular mechanisms of O-GlcNAcylation. Curr Opin Struct Biol. Oct. 2008;18(5):551-7. Epub Oct. 6, 2008.

Izumi et al., Bisubstrate analogues as glycosyltransferase inhibitors. Curr Top Med Chem. 2009;9(1):87-105.

Jiang et al., A neutral diphosphate mimic crosslinks the active site of human O-GlcNAc transferase. Nat Chem Biol. Nov. 13, 2011;8(1):72-7. doi: 10.1038/nchembio.711. Supplementary Information included.

Jope et al., Glycogen synthase kinase-3 (GSK3): inflammation, diseases, and therapeutics. Neurochem Res. Apr.-May. 2007;32(4-5):577-95. Epub Aug. 30, 2006.

Kannoji et al., GSK3beta: a master switch and a promising target. Expert Opin Ther Targets. Nov. 2008;12(11):1443-55. doi: 10.1517/14728222.12.11.1443.

Koh et al., Inhibition of GSK-3 reduces infarct volume and improves neurobehavioral functions. Biochem Biophys Res Commun Jul. 11, 2008;371(4):894-9. doi: 10.1016/j.bbrc.2008.05.006. Epub May 12, 2008.

Konrad et al., Alloxan is an inhibitor of the enzyme O-linked N-acetylglucosamine transferase. Biochem Biophys Res Commun Apr. 26, 2002;293(1):207-12.

Lazarus et al., Structure of human O-GlcNAc transferase and its complex with a peptide substrate. Nature. Jan. 27, 2011;469(7331):564-7. Epub Jan. 16, 2011.

Lee et al., A potent and highly selective inhibitor of human alpha-1,3-fucosyltransferase via click chemistry. J Am Chem Soc. Aug. 13, 2003;125(32):9588-9.

Lee et al., Alloxan is an inhibitor of O-GlcNAc-selective N-acetyl-beta-D-glucosaminidase. Biochem Biophys Res Commun Dec. 1, 2006;350(4):1038-43. Epub Oct. 6, 2006.

Lefebvre et al., Effect of okadaic acid on O-linked N-acetylglucosamine levels in a neuroblastoma cell line. Biochim Biophys Acta. Oct. 18, 1999;1472(1-2):71-81.

Li et al., Regulation of mouse brain glycogen synthase kinase-3 by atypical antipsychotics. Int J Neuropsychopharmcacol. 2007;10:7-19.

Macauley et al., Increasing O-GlcNAc levels: an overview of small-molecule inhibitors of O-GlcNAcase. Biochim Biophys Acta. Feb. 2010;1800(2):107-21. Epub Aug. 4, 2009.

MaCauley et al., O-GlcNAcase uses substrate-assisted catalysis: kinetic analysis and development of highly selective mechanism-inspired inhibitors. J Biol Chem. Jul. 8, 2005;280(27):25313-22. Epub Mar. 28, 2005.

Nikoulina et al., Potential role of glycogen synthase kinase-3 in skeletal muscle insulin resistance of type 2 diabetes. Diabetes. Feb. 2000;49(2):263-71.

Ougolkov et al., Targeting GSK-3: a promising approach for cancer therapy? Future Oncol. Feb. 2006;2(1):91-100.

Peineau et al., LTP inhibits Ltd in the hippocampus via regulation of GSK3beta. Neuron. Mar. 1, 2007;53(5):703-17.

Pesnot et al., Structural and mechanistic basis for a new mode of glycosyltransferase inhibition. Nat Chem Biol. May 2010;6(5):321-3. Epub Apr. 4, 2010.

Phiel et al., GSK-3alpha regulates production of Alzheimer's disease amyloid-beta peptides. Nature. May 22, 2003;423(6938):435-9.

Rempel et al., Covalent inhibitors of glycosidases and their applications in biochemistry and biology. Glycobiology. Aug. 2008;18(8):570-86. Epub May 22, 2008.

Ring et al., Selective glycogen synthase kinase 3 inhibitors potentiate insulin activation of glucose transport and utilization in vitro and in vivo. Diabetes. Mar. 2003;52(3):588-95.

Saotome et al., Combinatorial library of five-membered iminocyclitol and the inhibitory activities against glyco-enzymes. Chem Biol. Nov. 2001;8(11):1061-70.

Sereno et al., A novel GSK-3beta inhibitor reduces Alzheimer's pathology and rescues neuronal loss in vivo. Neurobiol Dis. Sep. 2009;35(3):359-67. doi: 10.1016/j.nbd.2009.05.025. Epub Jun. 10, 2009.

Stambolic et al., Lithium inhibits glycogen synthase kinase-3 activity and mimics wingless signalling in intact cells. Curr Biol. Dec. 1, 1996;6(12):1664-8.

Szczepankiewicz et al., Association analysis of the GSK-3beta T-50C gene polymorphism with schizophrenia and bipolar disorder. Neuropsychobiology. 2006;53(1):51-6. Epub Jan. 4, 2006.

Tanabe et al., Genetic Deficiency of Glycogen Synthase Kinase-3β Corrects Diabetes in Mouse Models of Insulin Resistance. PloS Biology. 2008;6(2):307-318.

Wang et al., A search for pyrophosphate mimics for the development of substrates and inhibitors of glycosyltransferases. Bioorg Med Chem. Apr. 1997;5(4):661-72.

Wang et al., Glycogen synthase kinase 3 in MLL leukaemia maintenance and targeted therapy. Nature. Oct. 30, 2008;455(7217):1205-9. doi: 10.1038/nature07284. Epub Sep. 17, 2008.

(56) References Cited

OTHER PUBLICATIONS

Zhou et al., Growth control of multiple myeloma cells through inhibition of glycogen synthase kinase-3. Leukemia & Lymphoma, 2008;49(10):1945-1953.
U.S. Appl. No. 13/375,036, filed Jan. 9, 2012, Kahne et al.
U.S. Appl. No. 12/226,151, filed Sep. 11, 2009, Kahne et al.
U.S. Appl. No. 12/664,559, filed Jul. 21, 2010, Gross et al.
U.S. Appl. No. 14/013,860, filed Aug. 29, 2013, Gross et al.

* cited by examiner

DIPHOSPHATE MIMETICS AND USES THEREOF

RELATED APPLICATIONS

The present application is a national stage filing under 35 U.S.C. §371 of international PCT application, PCT/US2012/045675, filed Jul. 6, 2012, which claims priority under 35 U.S.C. §119(e) to U.S. provisional patent applications, U.S. Ser. No. 61/504,958, filed Jul. 6, 2011, and U.S. Ser. No. 61/584,443, filed Jan. 9, 2012, each of which is incorporated herein by reference.

GOVERNMENT SUPPORT

This invention was made with U.S. Government support under grants GM078477 and GM076710 awarded by the National Institutes of Health. The U.S. Government has certain rights in the invention.

BACKGROUND OF THE INVENTION

A diverse range of glycoconjugates exists in nature. See, e.g., Varki et al., Essentials of Glycobiology, 2nd edition, Cold Spring Harbor Laboratory Press, Cold Spring Harbor, N.Y., 2009. These glycoconjugates play fundamental roles in cell structure, signaling processes, and cell-cell recognition, but studying them is challenging due to a lack of suitable chemical tools. See, e.g., Kiessling et al., *Annu. Rev. Biochem.* (2010) 79:619-653. Glycosyltransferases (Gtfs) are the enzymes that assemble these glycoconjugates from carbohydrate building blocks. See, e.g., Wagner et al., *Chembiochem.* (2010) 11:1939-1949; Brown et al., *Crit. Rev. Biochem. Mol. Biol.* (2007) 42:481-515; Pesnot et al., *Nat. Chem. Biol.* (2010) 6:321-323; and Frantom et al., *J. Am. Chem. Soc.* (2010) 132:6626-6627. Most Gtfs transfer a sugar from an anionic leaving group, for example, a nucleotide, to an acceptor such as another sugar, a protein, or a lipid. See, e.g., Lairson et al., *Annu. Rev. Biochem.* (2008) 77:521-555.

O-linked N-acetylglucosamine (O-GlcNAc) transferase (OGT) catalyzes the addition of a single N-acetylglucosamine in O-glycosidic linkage to serine or threonine residues of intracellular proteins. OGT is an essential vertebrate Gtf that β-O-GlcNAcylates a wide variety of nuclear and cytoplasmic proteins, including transcription factors, cytoskeletal proteins, metabolic enzymes, kinases, phosphatases, proteasome components, chaperones, and neural proteins. See, e.g., Gambetta et al., *Science* (2009) 325:93-96; Sinclair et al., *Proc. Natl. Acad. Sci. USA* (2009) 106:13427-32; Love et al., *Proc. Natl. Acad. Sci. USA* (2010) 107:7413-18. OGT-mediated glycosylation is dynamic. A corresponding glycosidase, O-GlcNAc hydrolase (OGA), removes O-GlcNAc residues from proteins. See, e.g., Goldberg et al., *Endocrinology* (2006) 147:222-31; Kreppel et al., *J. Biol. Chem.* (1997) 272:9308-15. O-GlcNAc cycling is sensitive to stress conditions and nutrient status, particularly glucose levels. See, e.g., Lubas et al., *J. Biol. Chem.* (1997) 272:9316-24. OGT glycosylates many aminoacid side chains that could otherwise be phosphorylated, suggesting that OGlcNAcylation modulates kinase signaling. See, e.g., Jinek et al., *Nat. Struct. Mol. Biol.* (2004) 11:1001-07; Ha et al., *Protein Sci.* (2000) 9:1045-52; Hu et al., *Proc. Natl. Acad. Sci. USA* (2003) 100:845-849. Excessive OGT activity results in hyper-OGlcNAcylation, which is correlated with widespread transcriptional changes and a number of pathologies, including cancer. See, e.g., Wrabl et al., *J. Mol. Biol.* (2001) 314:365-74; Martinez-Fleites et al., *Nat. Struct. Mol. Biol.* (2008) 15:764-65.

Small molecule inhibitors of OGT have been sought for many years as cellular probes, and different approaches to identify such inhibitors have been explored. See, e.g., Gloster et al., *Nat. Chem. Biol.* (2011) 7:174-181; Konrad et al., *Biochem. Biophys. Res. Commun.* (2002) 293:207-212; Hajduch et al., *Carbohydr. Res.* (2008) 343:189-195. OGT has been found to be a challenging target because it is a nucleotide-sugar glycosyltransferase and the donor sugar substrate contains a diphosphate leaving group. The proposed transition state for these types of enzymes is dissociative, and the oxonium ion-like portion resembles the transition state of glycosidases. See, e.g., Vocadlo et al., *Curr. Opin. Chem. Biol.* (2008) 12:539-555; Gloster et al., *Org. Biomol. Chem.* (2010) 8:305-320. A key difference in glycosidase and Gtf transition states is that in the latter a negatively charged diphosphate leaving group rather than a carboxylate side chain helps stabilize the oxonium character. See, e.g., Lairson et al., *Annu. Rev. Biochem.* (2008) 77:521-555. Accordingly, although there are many good inhibitors of glycosidases, including OGA, these compounds typically do not inhibit Gtfs effectively. See, e.g., Macauley et al., *Biochim. Biophys. Acta* (2010) 1800:107-121; Rempel et al., *Glycobiology* (2008) 18:570-586; Dorfmueller et al., *Chem. Biol.* (2010) 17:1250-1255; Kim et al., *J. Am. Chem. Soc.* (2006) 128:4234-4235.

Efforts to identify selective Gtf inhibitors have focused primarily on the design of substrate mimics of negatively charged diphosphates. See, e.g., Trunkfield et al., *Bioorg. Med. Chem.* (2010) 18:2651-2663; Izumi et al., *Curr. Top. Med. Chem.* 9, 87-105 (2009); Skropeta et al., *Glycoconj. J.* (2004) 21:205-219. A major hurdle has been finding suitable replacements for the anionic phosphates. See, e.g., Wang et al., *Bioorg. Med. Chem.* (1997) 5:661-672; Helm et al., *J. Am. Chem. Soc.* (2003) 125:11168-11169; Hang et al., *Chem. Biol.* (2004) 11:337-345. These phosphates contribute significantly to binding affinity, and replacing them with neutral linkers usually results in weak inhibitors. Furthermore, retaining the phosphates typically prevents the Gtf inhibitor from getting into a cell. Vocadlo and coworkers developed protected sugar analogs of Gtf inhibitors which were fed to cells and subsequently metabolized into the corresponding nonhydrolyzable nucleotide-sugar donors in vitro. See, e.g., Gloster et al., *Nat. Chem. Biol.* (2011) 7:174-181. The method of Vocadlo allows polar donor analogs to be used as inhibitors in cells but it offers limited opportunities to tune selectivity since the inhibitors produced closely resemble common cellular substrates. Thus, there continues to remain a need for new and alternative approaches in the development of Gtf inhibitors, particularly OGT inhibitors, for use in studying the role of glycosylation in the cell as well as in the treatment of diseases associated with aberrant glycosylation.

Another important class of enzymes that could be inhibited with diphosphate mimetics is protein kinases. Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. Kinases may be categorized into families by the substrates they phosphorylate (e.g., protein-tyrosine, protein-serine/threonine, lipids, etc.). In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein's biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, neurodegenerative diseases, and proliferative diseases (e.g., cancer). Accordingly, there remains a need to find protein kinase inhibitors useful as therapeutic agents.

SUMMARY OF THE INVENTION

The present invention provides compounds and pharmaceutically acceptable salts thereof for use in inhibiting enzymes, e.g., glycosyltransferases and kinases. In certain embodiments, compounds of the present invention are useful as glycosyltransferase inhibitors, in particular, as inhibitors of O-linked N-acetylglucosamine (O-GlcNAc) transferase (OGT) activity. In certain embodiments, compounds of the present invention are useful as kinase inhibitors (e.g., PLK1 inhibitors, GSK3β inhibitors, MAPKAPK2 inhibitors). The present invention further provides pharmaceutical compositions and methods of using the inventive compounds. For example, provided compounds can be used as biological probes to study the effects of inhibiting enzyme activity, e.g., OGT activity and/or kinase activity. Provided compounds can also be used as therapeutics, e.g., for the treatment of conditions associated with inhibition of OGT activity and/or kinase activity, such as, for example, for the treatment of proliferative diseases, neurodegenerative diseases, diabetes or complications thereof, autoimmune diseases, and inflammatory diseases.

In one aspect, the present invention provides compounds of Formula (I):

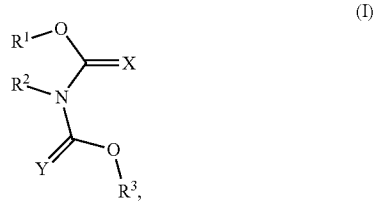

(I)

or pharmaceutically acceptable salts thereof, wherein X, Y, $R^1$, $R^2$, and $R^3$ are as defined herein. In certain embodiments, X and Y are each oxygen, and the compound is a dicarbamate. In certain other embodiments, X and Y are each sulfur, and the compound is a dithiocarbamate. In yet other embodiments, X is sulfur and Y is oxygen, or X is oxygen and Y is sulfur. In certain embodiments, $R^1$ and $R^2$ form a 5-membered oxazolidin-2-one ring or a 6-membered 1,3-oxazinan-2-one ring, wherein the ring is optionally substituted or fused to an optionally substituted carbocyclyl, optionally substituted heterocyclyl, optionally substituted aryl, or optionally substituted heteroaryl ring. In certain embodiments, $R^3$ is optionally substituted aryl. In certain embodiments, a compound of Formula (I) comprises one or more electron-withdrawing substituents attached to $R^1$ and/or $R^2$, or the ring formed therefrom. In certain embodiments, a compound of Formula (I) comprises one or more electron-withdrawing substituents attached to the group $R^3$. In certain embodiments, a compound of Formula (I) comprises one or more electron-donating substituents attached to the group $R^3$. In certain embodiments, a compound of Formula (I) comprises one or more electron-withdrawing attached to $R^1$ and/or $R^2$, or a ring formed therefrom, and one or more electron-donating substituents attached to the group $R^3$.

In another aspect, pharmaceutical compositions are provided which comprise an effective amount of a compound of Formula (I), or a pharmaceutically acceptable salt thereof, and optionally a pharmaceutically acceptable excipient.

In yet another aspect, methods of inhibiting an enzyme are provided which comprise contacting a compound of Formula (I), or a pharmaceutically acceptable salt thereof, with an enzyme in an amount sufficient to inhibit the enzyme's activity.

In certain embodiments, methods of inhibiting O-GlcNAc transferase are provided which comprise contacting a compound of Formula (I), or a pharmaceutically acceptable salt thereof, with a O-GlcNAc transferase in an amount sufficient to inhibit activity of O-GlcNAc transferase. The OGT may be purified or crude, and may be present in a cell, tissue, or a subject. Thus, such methods encompasses both inhibition of in vitro and in vivo OGT activity.

In certain embodiments, methods of inhibiting a kinase are provided which comprise contacting a compound of Formula (I), or a pharmaceutically acceptable salt thereof, with a kinase in an amount sufficient to inhibit the kinase's activity. The enzyme may be purified or crude, and may be present in a cell, tissue, or a subject. Thus, such methods encompasses both inhibition of in vitro and in vivo kinase activity.

In still another aspect, methods of treating an O-linked N-acetylglucosamine (O-GlcNAc) transferase (OGT)-mediated condition are provided which comprise administering an effective amount of a compound of Formula (I), or a pharmaceutically acceptable salt thereof, to a subject in need thereof. In certain embodiments, the O-linked N-acetylglucosamine (O-GlcNAc) transferase (OGT)-mediated condition is selected from the group consisting of proliferative diseases, neurodegenerative diseases, diabetes or complications thereof, autoimmune diseases, and inflammatory diseases. In certain embodiments, the O-linked N-acetylglucosamine (O-GlcNAc) transferase (OGT)-mediated condition is a proliferative disease, e.g., cancer.

In yet another aspect, methods of treating a kinase-mediated condition are provided which comprise administering an effective amount of a compound of Formula (I), or a pharmaceutically acceptable salt thereof, to a subject in need thereof. In certain embodiments, the kinase-mediated condition is selected from the group consisting of proliferative diseases, neurodegenerative diseases, autoimmune diseases, and inflammatory diseases. In certain embodiments, the kinase-mediated condition is a proliferative disease, e.g., cancer.

This application refers to various issued patent, published patent applications, journal articles, and other publications, all of which are incorporated herein by reference.

The details of one or more embodiments of the present invention are set forth herein. Other features, objects, and advantages of the present invention will be apparent from the Detailed Description, the Figures, the Examples, and the Claims.

DEFINITIONS

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_1$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3 to 10-membered non aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{bb}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)R$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHS O$_2$ (C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-5}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O) (R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$, are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, pphenylbenzamide, onitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2(o-nitrophenoxy)propanamide, 2-methyl-2(ophenylazophenoxy) propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O) OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Sulfonamide nitrogen protecting groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

These and other exemplary substituents are described in more detail in the Detailed Description, Examples, and claims. The present invention is not intended to be limited in any manner by the above exemplary listing of substituents.

Other Definitions

"Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, quaternary salts.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female at any stage of development. A non-human animal may be a transgenic animal.

"Condition," "disease," and "disorder" are used interchangeably herein.

"Treat," "treating" and "treatment" encompasses an action that occurs while a subject is suffering from a condition which reduces the severity of the condition or retards or slows the progression of the condition ("therapeutic treatment"). "Treat," "treating" and "treatment" also encompasses an action that occurs before a subject begins to suffer from the condition and which inhibits or reduces the severity of the condition ("prophylactic treatment").

An "effective amount" of a compound refers to an amount sufficient to elicit the desired biological response, i.e., treat the condition. As will be appreciated by those of ordinary skill in this art, the effective amount of a compound of the invention may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount"

can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "kinase" represent transferase class enzymes that are able to transfer a phosphate group from a donor molecule to an acceptor molecule, e.g., an amino acid residue of a protein or a lipid molecule. Representative, non-limiting examples of kinases include Abl, ACK, Akt1/PKBα, Akt2/PKBβ, Akt3/PKBγ, ALK1, ALK2, Alk4, AMPKα1/β1/γ1, AMPKα1/β1/γ2, AMPKα1/β1/γ3, AMPKα1/β2/γ1, AMPKα2/β1/γ1, AMPKα2/β2/γ2, Abl2, ARKS, Ask1, Aurora A, Aurora B, Aurora C, Axl, BARK1, Blk, Bmx, B-Raf, Brk, BrSK1, BrSK2, Btk, CaMK1α, CaMK1β, CaMK1γ, CaMK1δ, CAMK2α, CaMK2β, CAMK2δ, CAMK2γ, CAMK4, CAMKK1, CAMKK2, CDK1, CDK2, CDK3, CDK4, CDK5, CDK6, CDK7, CDK9, CDK1/cyclin B, CDK2/cyclin A, CDK2/cyclin E, CDK3/cyclin E, CDK5/p25, CDK5/p35, CDK6/cyclinD3, CDK7/cyclin H/MAT1, CDK9/cyclin T1, CHK1, CHK2, CK1(γ), CK1δ, CK2α1, CK2α2, cKit, c-RAF, CLK1, CLK2, CLK3, COT, Csk, DAPK1, DAPK2, DAPK3, DCAMLK2, DDR2, DMPK, DRAK1, DYRK1A, DYRK2, DYRK3, eEF2K, EGFR, EPHA1, EPHA2, EPHA3, EPHA4, EPHA5, EPHA6, EPHA7, EPHA8, EphB1, EphB2, EphB3, EphB4, ErbB4, Erk1, Erk2, FAK, Fer, Fes, FGFR1, Flt2, Flt4, FLT3 D835Y, FGFR2, FGFR3, FGFR4, Fgr, Flt1, Flt3, Fms, FRK, FynA, GCK, GPRK5, GRK2, GRK4, GRK6, GRK7, GSK3α, GSK3β, Hck, HER2, HER4, HIPK1, HIPK2, HIPK3, HIPK4, IGF1R, IKKβ, IKKα, IKKε, IR, InsR, IRR, IRAK1, IRAK2, IRAK4, Itk, JAK2, JAK3, JNK1, JNK2, JNK3, KDR, KHS1, Kit, Lck, LIMK1, LKB1, LOK, LRRK2, Lyn A, Lyn B, MAPK1, MAPK2, MAPK12, MAPKAP-K2, MAPKAP-K3, MAPKAPK2, MAPKAPK3, MAPKAPK5, MARK1, MARK2, MARK3, MARK4, MELK, MEK1, MEK2, MEKK2, MEKK3, Mer, Met, MET M1250T, MINK, MKK4, MKK6, MKK7β, MLCK, MLK1, MLK3, MNK1, MNK2, MRCKα, MRCKβ, MSK1, MSK2, MSSK1, STK23, STK4, STK3, STK24, MST1, MST2, MST3, MST4, MUSK, mTOR, MYO3β, MYT1, NDR1, NEK11, NEK2, NEK3, NEK6, NEK7, NEK9, NLK, NUAK2, p38α, p38β, p38δ, p38γ, p70S6K, S6K, SRK, PAK1/CDC42, PAK2, PAK3, PAK4, PAK5, PAK6, PAR-1Bα, PASK, PBK, PDGFRα, PDGFRβ, PDK1, PEK, PHKG2, PI3Kα, PI3Kβ, PI3Kγ, PI3Kδ, Pim1, Pim2, PKAcα, PKAcβ, PKAcγ, PKA(b), PKA, PKBα, PKBPβ, PKBγ, PKCα, PKCβ1, PKCβ2, PKCβ11, PKCδ, PKCε, PKCγ, PKCμ, PKCη, PKCι, PKCθ, PKCζ, PKD1, PKD2, PKD3, PKG1α, PKG1B, PKN1, PKN2, PKR, PLK1, PLK2, PLK3, PLK4, Polo, PRAK, PRK2, PrKX, PTK5, PYK2, QIK, Raf1, Ret, RIPK2, RIPK5, ROCK1, ROCK2, RON, ROS, Rse, RSK1, RSK2, RSK3, RSK4, SAPK2a, SAPK2b, SAPK3, SAPK4, SGK1, SGK2, SGK3, SIK, MLCK, SLK, Snk, Src, SRPK1, SRPK2, STK33, SYK, TAK1-TAB1, TAK1, TBK1, TAO1, TAO2, TAO3, TBK1, TEC, TESK1, TGFβR1, TGFβR2, Tie2, TLK2, TrkA, TrkB, TrkC, TSSK1, TSSK2, TTK, TXK, TYK2, TYRO3, ULK1, ULK2, WEE1, WNK2, WNK3, Yes1, YSK1, ZAK, ZAP70, ZC3, and ZIPK.

BRIEF DESCRIPTION OF THE DRAWINGS

FIG. 2a is a graph showing OGT inactivation for representative BZX compounds after a five-minute preincubation with a three-fold excess of each test compound (1-6). Following dilution of the preincubation mixture, enzyme activity was tested as described, see, e.g., Clarke et al., Embo. J. (2008) 27:2780-88, and normalized to DMSO control. FIG. 2b shows time-dependent inactivation of OGT at 1.5:1 of inhibitor (2 and 6):enzyme ratio. After preincubation, the enzyme activity was tested. Percent enzyme activity corresponds to the mean±s.e.m., n=3.

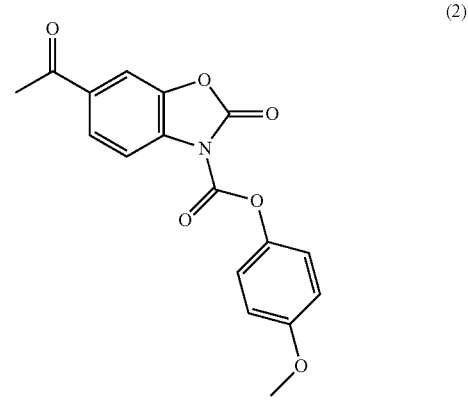

(2)

Figure 3:
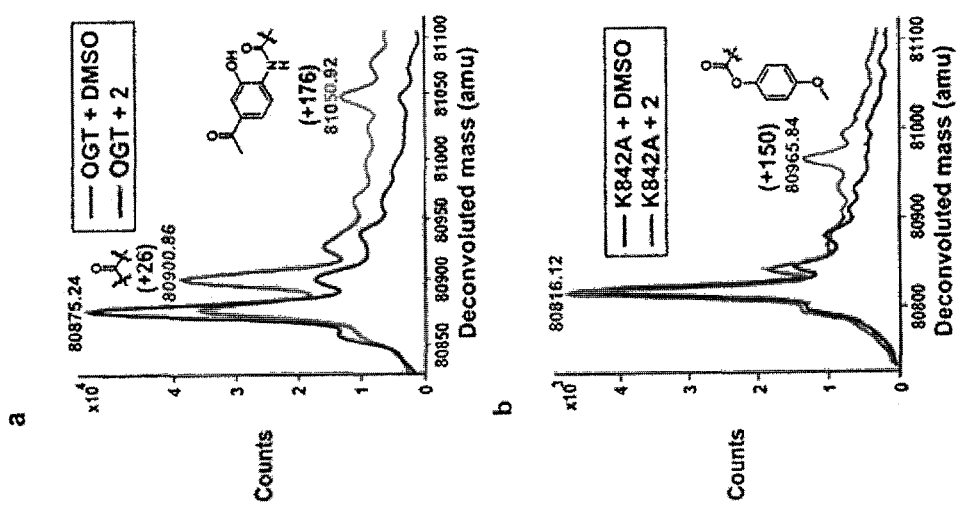

FIG. 3 depicts a covalent modifications map to active site lysine 842 and a hypothetical structure for each modification. An intact protein mass spectroscopic overlay of OGT treated with DMSO and compound (2) shows two covalent modifications (+26 Da and +176 Da) of the treated protein (FIG. 3a). An intact protein mass spectrum of (2)-treated K842A shows that mutation of K842 to alanine abolished +26 and +176 modifications, but a new +150 mass peak appeared and a possible structure corresponding to this adduct is shown (FIG. 3b).

Figure 4:
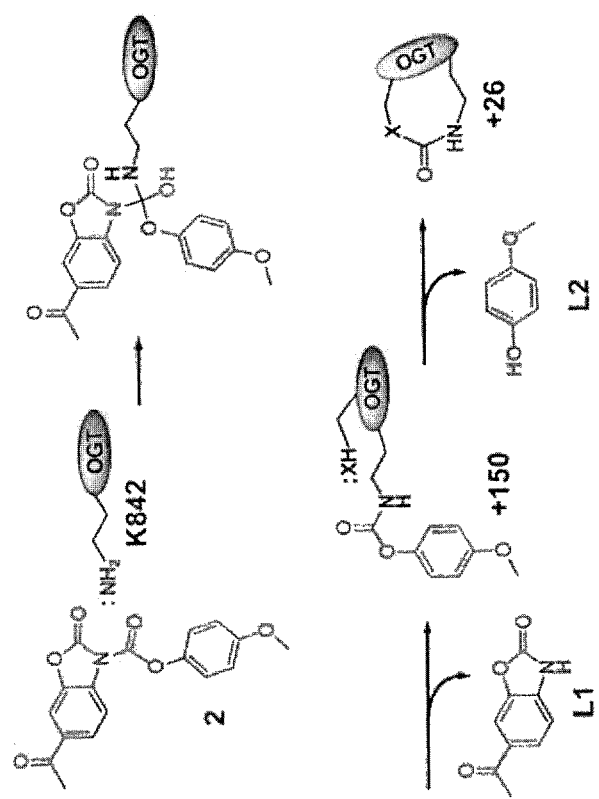

FIG. 4 depicts a proposed double displacement mechanism for the reaction of compound (2) with OGT. Mutation of K842 to alanine abolished the formation of the +26 modification, suggesting that K842 is the residue that reacts first with the acyclic carbamate of compound (2).

Figure 5:
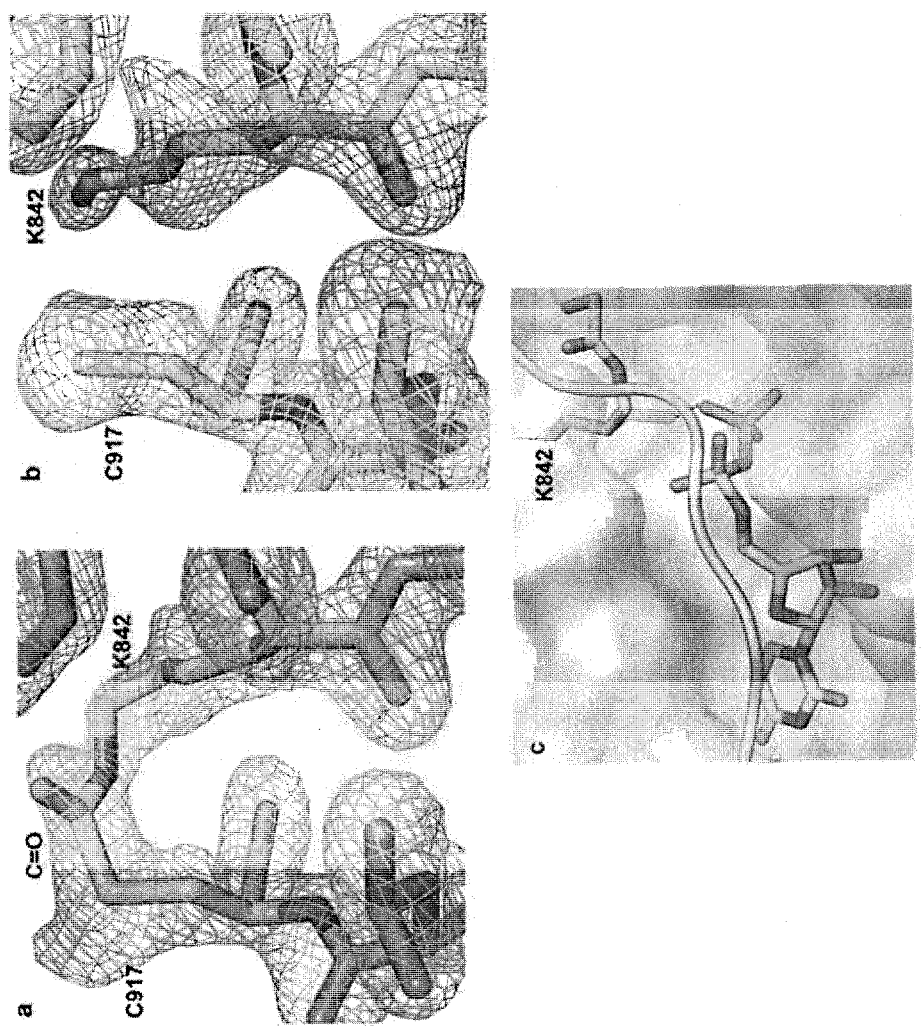

FIG. 5 depicts an active site comparison of OGT with and without treatment with compound (2). 2Fo-Fc composite omit map of OGT-2-UDP-CKII, FIG. 5a, shows the C=O crosslink bridging K842 and C917 together, contoured at 1.25 σ (map calculated to 1.95 Å). The map was calculated from a model lacking the crosslink. 2Fo-Fc composite omit map of OGT-UDP-CKII (PDB3PE4, 1.95 Å), FIG. 5b, shows that K842 and C917 are separated from each other, contoured at 1.25 σ. FIG. 5c depicts a surface representation of the active site of the OGT-2-UDP-CKII complex. The CKII peptide and UDP-GlcNAc are bound in the same conformations as in the absence of inhibitor. The crosslinked K842 is overlaid with the uncrosslinked K842 from the OGT-UDP-CKII complex. The inferred H-bond between the uncrosslinked K842 side chain and the β-phosphate of UDP is shown with a dashed line.

Figure 6:
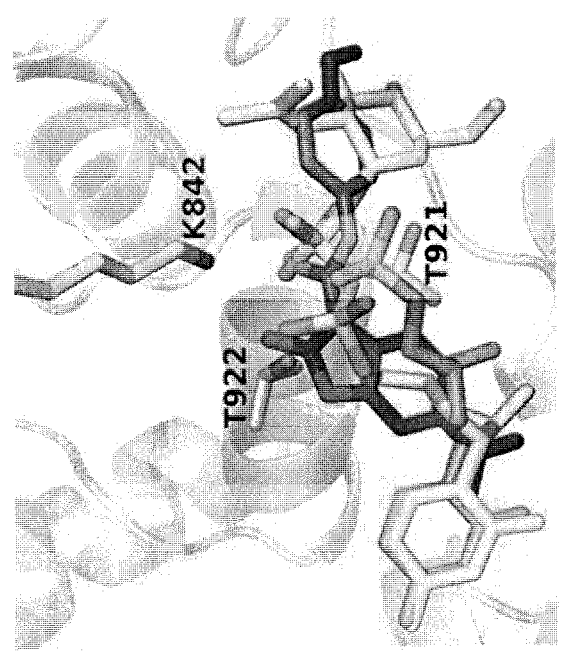

FIG. 6 depicts an overlay of UDP (PDB 3PE4) in the OGT active site with top-scoring poses of docked compound (2) and UDP-GlcNAc shows that the dicarbamate of compound (2) binds in the same location as the diphosphate. The side chain amine of K842 is located between the dicarbamate carbonyls, which are sandwiched by two neighboring threonines (T921 and T922) in the diphosphate binding site.

Figure 7:
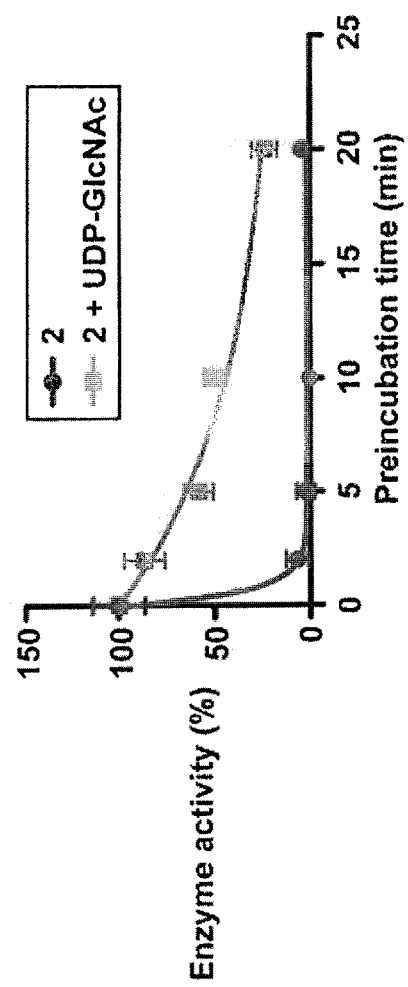

FIG. 7 shows that UDP-GlcNAc protects OGT from inactivation by compound (2). OGT (5 µM) was preincubated with compound (2) (20 µM) in the presence and absence of UDP-GlcNAc (40 µM) at room temperature for 2-20 min. The enzyme mixture was diluted 100-fold before reacting with substrates (6 µM UDP-$^{14}$C-GlcNAc and 500 µM CKII peptide) and incubated at room temperature for another 2 h. The final concentration of added cold UDP-GlcNAc is 5% of the total UDP-GlcNAc concentration, and its effect should be negligible. Values correspond to the mean±s.e.m., n=3.

Figure 8:
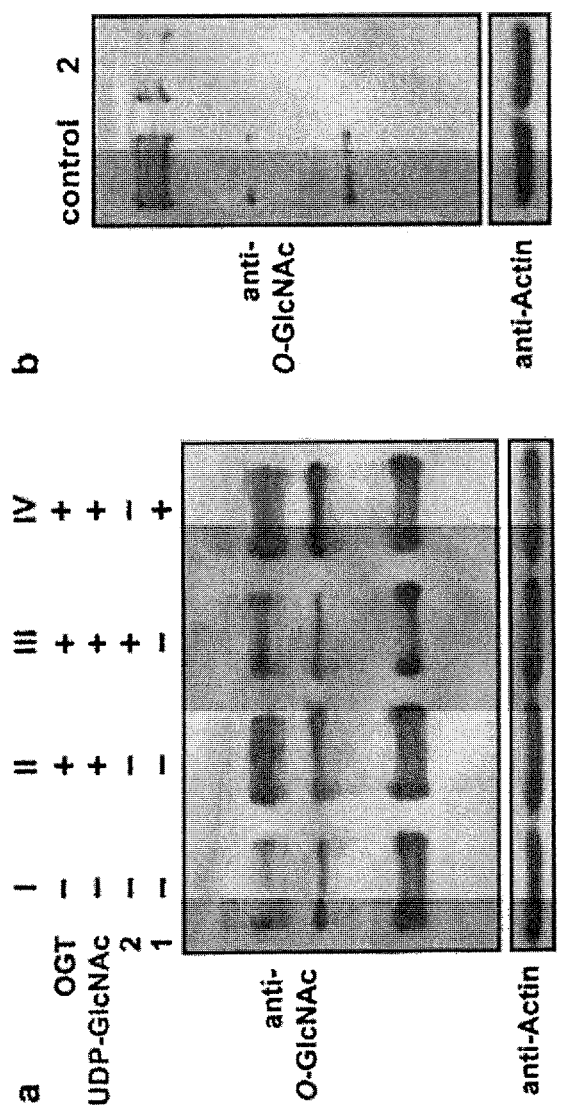

FIG. 8 depicts Western blots showing reduced O-GlcNAcylation by OGT in the presence of BZX compounds. FIG. 8a shows a Western blot of MCF-10A ErbB2 cell lysates treated as indicated. OGT was used at 2 µM, UDP-GlcNAc at 1 mM, and BZX inhibitors at 200 µM. FIG. 8b shows a Western blot of lysates from MCF-100A ErbB2 cells treated with compound (2). Actin was used as a loading control.

Figure 9:
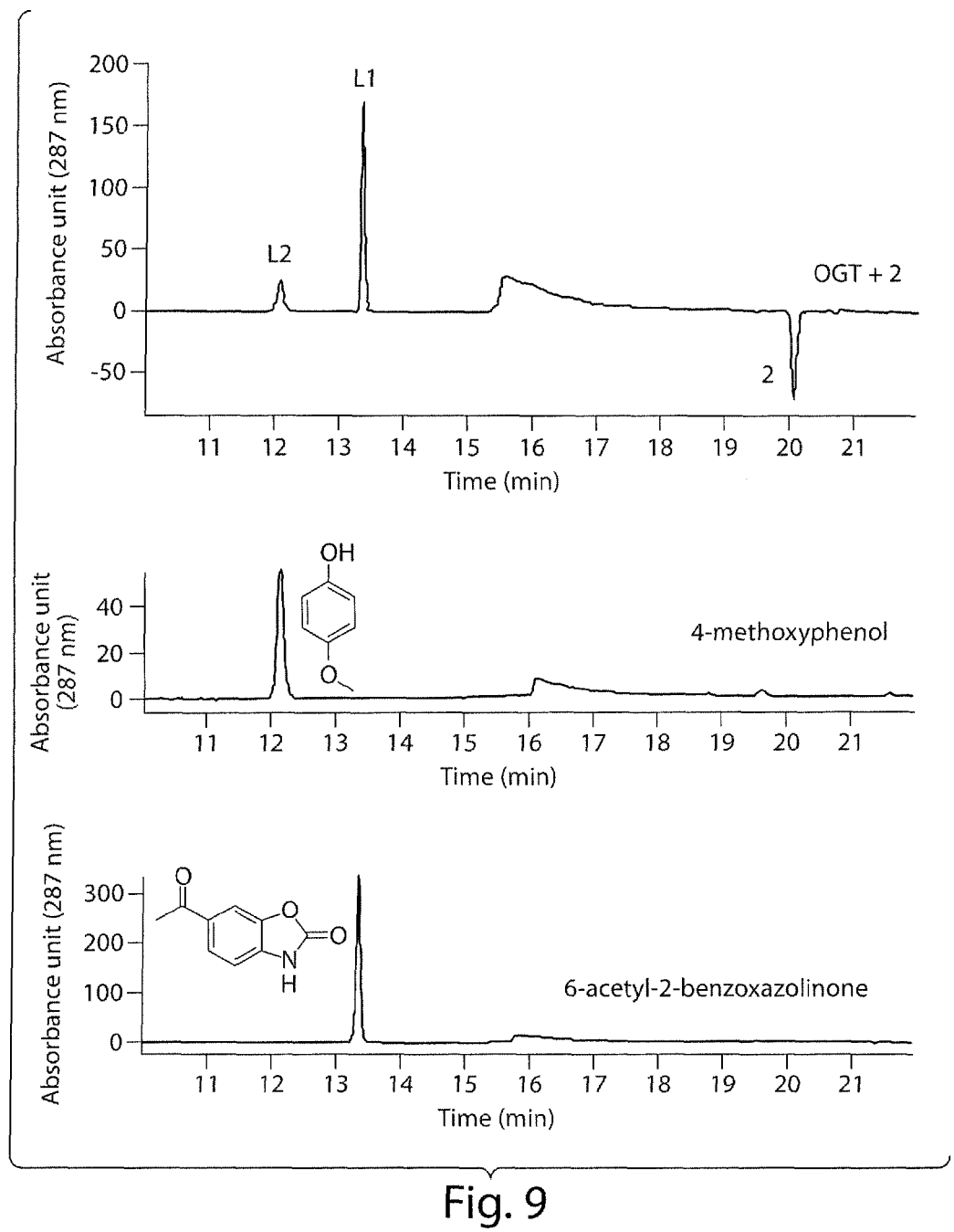

FIG. 9 depicts LC-MS spectra identifying leaving groups from the reaction of OGT with compound (2). The two leaving groups generated from the reaction have the same elution times and the same exact masses as authentic standards of 4-methoxyphenol ($\epsilon_{287}$ nm=3.16 mM$^{-1}$ cm$^{-1}$) and 6-acetyl-2-benzoxazolinone ($\epsilon_{287}$ nm=10.14 mM$^{-1}$ cm$^{-1}$), respectively (the no enzyme control was subtracted to minimize the background UV$_{287nm}$ absorbance). 6-Acetyl-2-benzoxazolinone [M+H]$^+$ m/z 178.050; detected (L) [M+H]$^+$ m/z 178.049. 4-Methoxyphenol [M+H]+m/z 125.059; detected (L2) [M+H]$^+$ m/z 125.059.

Figure 10A:
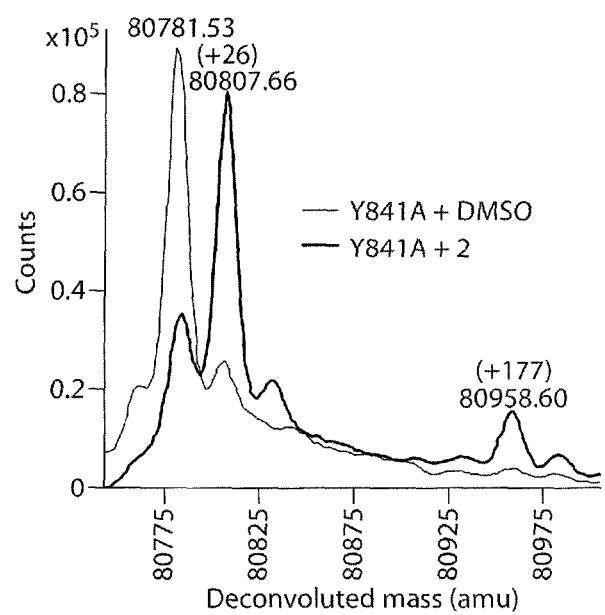
Figure 10B:
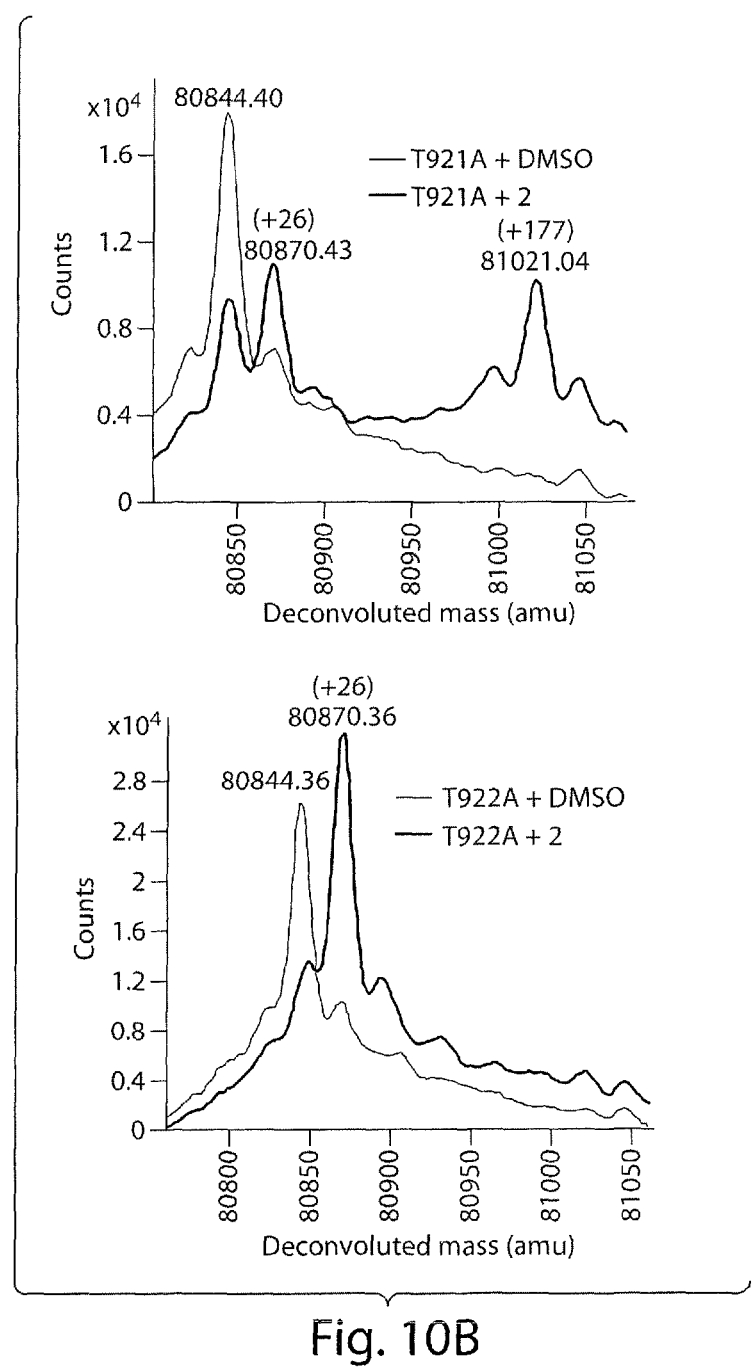
Figure 10C:
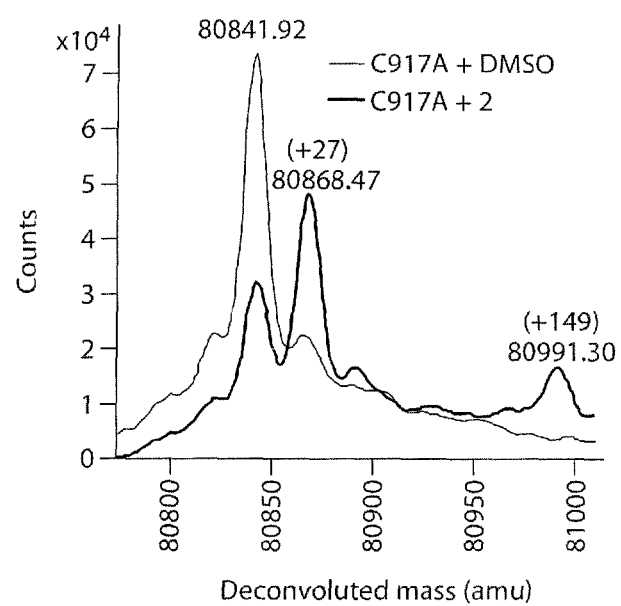

FIG. 10 depicts an overlay of intact protein mass spectra of DMSO-treated (control) and compound (2)-treated OGT mutants. Three possible outcomes are illustrated: FIG. 10a: Y841A—no change. FIG. 10b: T921A and T922A—changes in apparent product distributions. FIG. 10c: C917A—accumulation of the +150 modification on K842. The site of modification was determined by analyzing tryptic digests.

Figure 11:
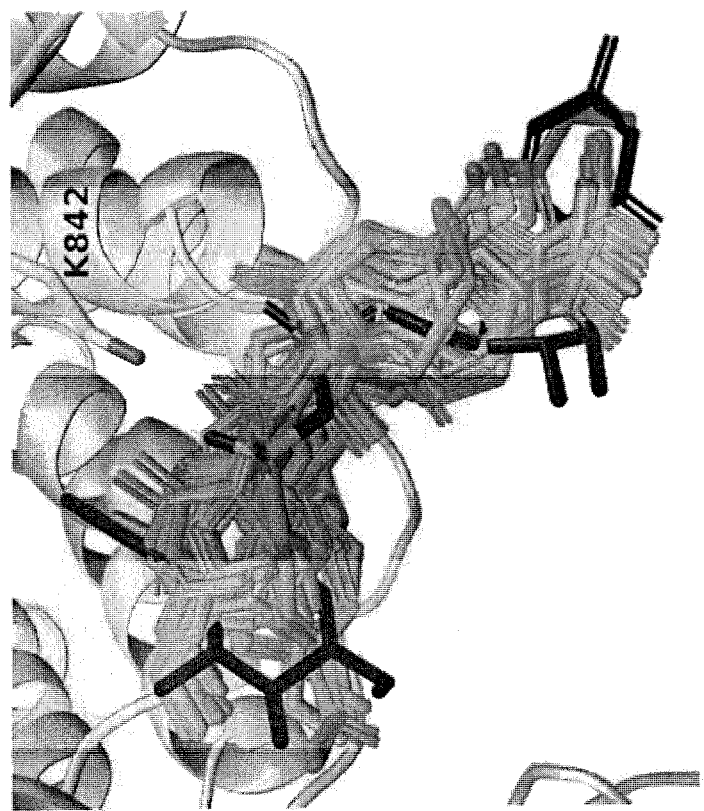

FIG. 11 depicts an overlay of 50 docking poses of compound (2) with top-scoring docked UDP-GlcNAc. The overlay shows that in all fifty cases the dicarbamate aligns in the same location as the diphosphate in the active site of OGT. K842 is pointing to the dicarbamate carbonyls.

Figure 12:
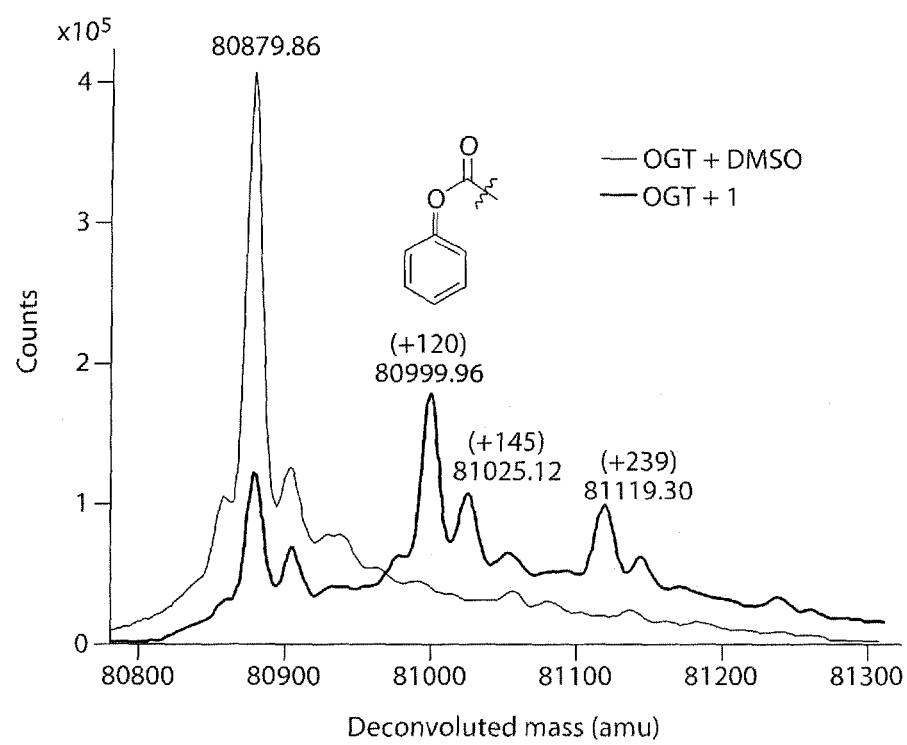

FIG. 12 depicts an intact protein mass spectrum of hOGT$_{45}$ overlaid with an intact protein mass spectrum of compound (1)-treated OGT (incubated at a 1:1 ratio at room temperature for 30 min.). Multiple peaks were observed, and some can only be explained if the protein is modified more than once. LC-MS/MS analyses of tryptic digests for OGT treated with compound (1) are consistent with predicted cross-linking to cysteine and lysine residues.

Figure 13:
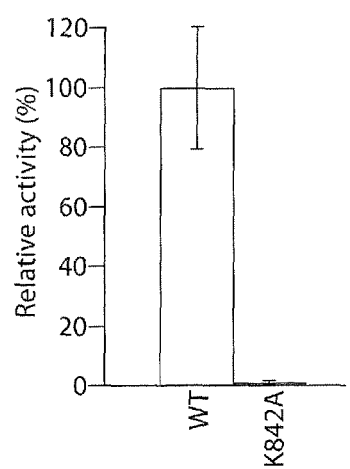

FIG. 13 depicts the relative activity of the K842A mutant compared to the wild-type (WT) hOGT$_{4.5}$ enzyme, tested as previously described. See Gross et al., J. Am. Chem. Soc. (2005) 127:14588-14589. Values correspond to the mean±s.e.m., n=3. This is consistent with data reported by others. See, e.g., Martinez-Fleites et al., Nat. Struct. Mol. Biol. (2008) 15:764-765.

DETAILED DESCRIPTION OF CERTAIN EMBODIMENTS OF THE INVENTION

The present invention provides compounds which are useful for the inhibition of enzymes, such as kinases and glycosyltransferases, in particular, O-linked N-acetylglucosamine (O-GlcNAc) transferase (OGT). The present invention further provides pharmaceutical compositions of the inventive compounds and methods of using the inventive compounds. In certain embodiments, a provided compound is an OGT inhibitor. In certain embodiments, a provided compound is a kinase inhibitor. In certain embodiments, a provided compound is a PLK1 inhibitor. In certain embodiments, a provided compound is a GSK3β inhibitor. In certain embodiments, a provided compound is a MAP-KAPK2 inhibitor. In certain embodiments, a provided compound is used to treat a kinase-mediated condition or an OGT-mediated condition selected from the group consisting of proliferative diseases, neurodegenerative diseases, diabetes or complications thereof, autoimmune diseases, and inflammatory diseases.

Without wishing to be bound by any particular theory, it is proposed provided compounds behave as neutral diphosphate mimics. In some embodiments, provided compounds are useful for inhibiting enzymes that use substrates containing diphosphates or triphosphates. For example, a provided compound can inhibit an enzyme by reacting with an essential active site lysine that normally anchors the diphosphate of the nucleotide-sugar substrate of Gtf O-linked N-acetylglucosamine (O-GlcNAc) transferase (OGT), and further reacting with a nearby cysteine to cross-link the active site of the enzyme. Through changing the nature and location of the substituents on the molecular scaffold, e.g., by fine tuning the electronics of the scaffold, compounds which effectively inhibit OGT function have been discovered and are described herein. In certain embodiments, a provided compound inhibits one or more kinases. In certain embodiments, a provided compound inhibits PLK (e.g., PLK1, PLK2, PLK3, and/or PLK4). In certain embodiments, a provided compound inhibits PLK1.

Compounds

As generally described above, the present invention provides compounds useful as enzyme inhibitors, e.g., OGT inhibitors, or kinase inhibitors, e.g., PLK1 inhibitors, GSK30 inhibitors, MAPKAPK2 inhibitors. In one aspect, the present invention provides compound of Formula (I):

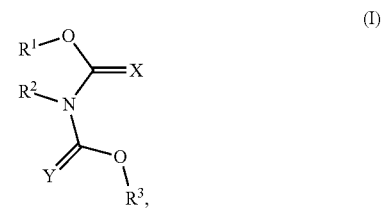

or a pharmaceutically acceptable salt thereof;
wherein:
X is O or S;
Y is O or S;

R[1] and R[2] are independently optionally substituted alkyl, optionally substituted alkenyl, optionally substituted alkynyl, optionally substituted carbocyclyl, optionally substituted heterocyclyl, optionally substituted aryl, or optionally substituted heteroaryl, or R[1] and R[2] are taken together to form a 5-membered oxazolidin-2-one ring or a 6-membered 1,3-oxazinan-2-one ring, wherein the ring is optionally substituted or fused to an optionally substituted carbocyclyl, optionally substituted heterocyclyl, optionally substituted aryl, or optionally substituted heteroaryl ring; and R[3] is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, a compound of Formula (I) is not:

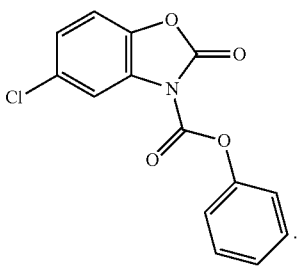 [SMILES: O=C(Oc1ccccc1)n1c(=O)oc2ccc(Cl)cc21]

In certain embodiments, X and Y are each oxygen, and a provided compound is of Formula (II):

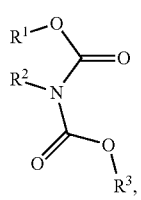

(II)

or a pharmaceutically acceptable salt thereof;
wherein:

R[1] and R[2] are independently optionally substituted alkyl, optionally substituted alkenyl, optionally substituted alkynyl, optionally substituted carbocyclyl, optionally substituted heterocyclyl, optionally substituted aryl, or optionally substituted heteroaryl, or R[1] and R[2] are taken together to form a 5-membered oxazolidin-2-one ring or a 6-membered 1,3-oxazinan-2-one ring, wherein the ring is optionally substituted or fused to an optionally substituted carbocyclyl, optionally substituted heterocyclyl, optionally substituted aryl, or optionally substituted heteroaryl ring; and R[3] is optionally substituted alkyl, optionally substituted alkenyl, optionally substituted alkynyl, optionally substituted carbocyclyl, optionally substituted heterocyclyl, optionally substituted aryl, or optionally substituted heteroaryl;

provided that the compound is not:

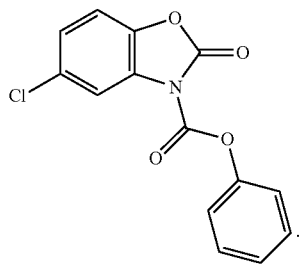 [SMILES: O=C(Oc1ccccc1)n1c(=O)oc2ccc(Cl)cc21]

In certain embodiments, a compound of Formula (I) or (II) is not:

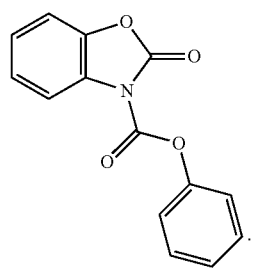 [SMILES: O=C(Oc1ccccc1)n1c(=O)oc2ccccc21]

In certain embodiments, a compound of Formula (I) or (II) is not:

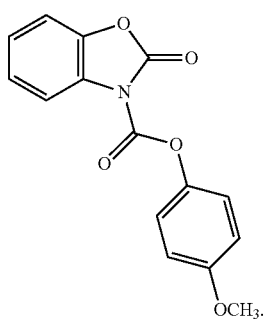 [SMILES: COc1ccc(OC(=O)n2c(=O)oc3ccccc32)cc1]

In certain embodiments, a compound of Formula (I) or (II) is not:

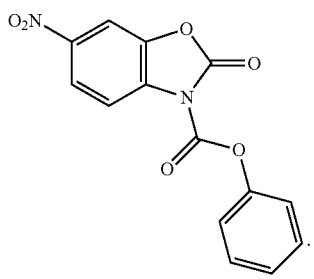

In certain embodiments, X is sulfur and Y is oxygen, and a provided compound is of Formula (III):

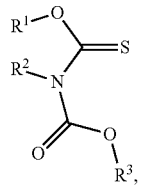

(III)

or a pharmaceutically acceptable salt thereof;
wherein:

$R^1$ and $R^2$ are independently optionally substituted alkyl, optionally substituted alkenyl, optionally substituted alkynyl, optionally substituted carbocyclyl, optionally substituted heterocyclyl, optionally substituted aryl, or optionally substituted heteroaryl, or $R^1$ and $R^2$ are taken together to form a 5-membered oxazolidin-2-one ring or a 6-membered 1,3-oxazinan-2-one ring, wherein the ring is optionally substituted or fused to an optionally substituted carbocyclyl, optionally substituted heterocyclyl, optionally substituted aryl, or optionally substituted heteroaryl ring; and $R^3$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, X is oxygen and Y is sulfur, and a provided compound is of Formula (IV):

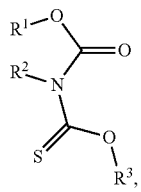

(IV)

or a pharmaceutically acceptable salt thereof;
wherein:

$R^1$ and $R^2$ are independently optionally substituted alkyl, optionally substituted alkenyl, optionally substituted alkynyl, optionally substituted carbocyclyl, optionally substituted heterocyclyl, optionally substituted aryl, or optionally substituted heteroaryl, or $R^1$ and $R^2$ are taken together to form a 5-membered oxazolidin-2-one ring or a 6-membered 1,3-oxazinan-2-one ring, wherein the ring is optionally substituted or fused to an optionally substituted carbocyclyl, optionally substituted heterocyclyl, optionally substituted aryl, or optionally substituted heteroaryl ring; and $R^3$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, X and Y are each sulfur, and a provided compound is of Formula (V):

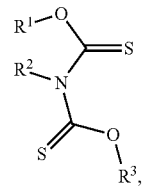

(V)

or a pharmaceutically acceptable salt thereof;
wherein:

$R^1$ and $R^2$ are independently optionally substituted alkyl, optionally substituted alkenyl, optionally substituted alkynyl, optionally substituted carbocyclyl, optionally substituted heterocyclyl, optionally substituted aryl, or optionally substituted heteroaryl, or $R^1$ and $R^2$ are taken together to form a 5-membered oxazolidin-2-one ring or a 6-membered 1,3-oxazinan-2-one ring, wherein the ring is optionally substituted or fused to an optionally substituted carbocyclyl, optionally substituted heterocyclyl, optionally substituted aryl, or optionally substituted heteroaryl ring; and $R^3$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

As generally defined above, $R^1$ and $R^2$ are independently optionally substituted alkyl, optionally substituted alkenyl, optionally substituted alkynyl, optionally substituted carbocyclyl, optionally substituted heterocyclyl, optionally substituted aryl, or optionally substituted heteroaryl, or $R^1$ and $R^2$ are taken together to form a 5-membered oxazolidin-2-one ring or a 6-membered 1,3-oxazinan-2-one ring, wherein the ring is optionally substituted or fused to an optionally substituted carbocyclyl, optionally substituted heterocyclyl, optionally substituted aryl, or optionally substituted heteroaryl ring.

In certain embodiments, $R^1$ is optionally substituted alkyl, e.g., $C_{1-10}$ alkyl. In certain embodiments, $R^1$ is optionally substituted $C_{1-8}$ alkyl, optionally substituted $C_{1-6}$ alkyl, optionally substituted $C_{1-4}$ alkyl, optionally substituted $C_{1-2}$ alkyl, optionally substituted $C_{2-8}$ alkyl, optionally substituted $C_{2-6}$ alkyl, or optionally substituted $C_{2-4}$ alkyl.

In certain embodiments, $R^1$ is optionally substituted alkenyl, e.g., $C_{2-10}$ alkenyl. In certain embodiments, $R^1$ is optionally substituted $C_{2-8}$ alkenyl, optionally substituted $C_{2-6}$ alkenyl, optionally substituted $C_{2-4}$ alkenyl, or optionally substituted $C_{2-3}$ alkenyl.

In certain embodiments, $R^1$ is optionally substituted alkynyl, e.g., $C_{2-10}$ alkynyl. In certain embodiments, $R^1$ is optionally substituted $C_{2-8}$ alkynyl, optionally substituted $C_{2-6}$ alkynyl, optionally substituted $C_{2-4}$ alkynyl, or optionally substituted $C_{2-3}$ alkynyl.

In certain embodiments, $R^1$ is optionally substituted carbocyclyl, e.g., $C_{3-10}$carbocyclyl. In certain embodiments, $R^1$ is optionally substituted $C_{3-8}$carbocyclyl, optionally substituted $C_{4-8}$carbocyclyl, optionally substituted $C_{5-8}$carbocyclyl, optionally substituted $C_{5-7}$carbocyclyl, or optionally substituted $C_{5-6}$carbocyclyl.

In certain embodiments, $R^1$ is optionally substituted heterocyclyl, e.g., a 5- to 10-membered optionally substituted heterocyclyl. In certain embodiments, $R^1$ is a 5- to 8-membered optionally substituted heterocyclyl, a 5- to 7-membered optionally substituted heterocyclyl, or a 5- to 6-membered optionally substituted heterocyclyl.

In certain embodiments, $R^1$ is optionally substituted aryl, e.g., $C_6$ aryl or $C_{10}$ aryl. In certain embodiments, $R^1$ is optionally substituted $C_6$ aryl (i.e., phenyl). In certain embodiments, $R^1$ is optionally substituted $C_{10}$ aryl (i.e., napthyl).

In certain embodiments, $R^1$ is optionally substituted heteroaryl, e.g., a 5- to 10-membered optionally substituted heteroaryl. In certain embodiments, $R^1$ is a 5-membered optionally substituted heteroaryl, or a 6-membered optionally substituted heteroaryl.

In certain embodiments, $R^2$ is optionally substituted alkyl, e.g., $C_{1-10}$ alkyl. In certain embodiments, $R^2$ is optionally substituted $C_{1-8}$ alkyl, optionally substituted $C_{1-6}$ alkyl, optionally substituted $C_{1-4}$ alkyl, optionally substituted $C_{1-2}$ alkyl, optionally substituted $C_{2-8}$ alkyl, optionally substituted $C_{2-6}$ alkyl, or optionally substituted $C_{2-4}$ alkyl.

In certain embodiments, $R^2$ is optionally substituted alkenyl, e.g., $C_{2-10}$ alkenyl. In certain embodiments, $R^2$ is optionally substituted $C_{2-8}$ alkenyl, optionally substituted $C_{2-6}$ alkenyl, optionally substituted $C_{2-4}$ alkenyl, or optionally substituted $C_{2-3}$ alkenyl.

In certain embodiments, $R^2$ is optionally substituted alkynyl, e.g., $C_{2-10}$ alkynyl. In certain embodiments, $R^2$ is optionally substituted $C_{2-8}$ alkynyl, optionally substituted $C_{2-6}$ alkynyl, optionally substituted $C_{2-4}$ alkynyl, or optionally substituted $C_{2-3}$ alkynyl.

In certain embodiments, $R^2$ is optionally substituted carbocyclyl, e.g., $C_{3-10}$ carbocyclyl. In certain embodiments, $R^2$ is optionally substituted $C_{3-8}$ carbocyclyl, optionally substituted $C_{4-8}$ carbocyclyl, optionally substituted $C_{5-8}$ carbocyclyl, optionally substituted $C_{5-7}$ carbocyclyl, or optionally substituted $C_{5-6}$ carbocyclyl.

In certain embodiments, $R^2$ is optionally substituted heterocyclyl, e.g., a 5- to 10-membered optionally substituted heterocyclyl. In certain embodiments, $R^2$ is a 5- to 8-membered optionally substituted heterocyclyl, a 5- to 7-membered optionally substituted heterocyclyl, or a 5- to 6-membered optionally substituted heterocyclyl.

In certain embodiments, $R^2$ is optionally substituted aryl, e.g., $C_6$ aryl or $C_{10}$ aryl. In certain embodiments, $R^2$ is optionally substituted $C_6$ aryl (i.e., phenyl). In certain embodiments, $R^2$ is optionally substituted $C_{10}$ aryl (i.e., napthyl).

In certain embodiments, $R^2$ is optionally substituted heteroaryl, e.g., a 5- to 10-membered optionally substituted heteroaryl. In certain embodiments, $R^2$ is a 5-membered optionally substituted heteroaryl, or a 6-membered optionally substituted heteroaryl.

In certain embodiments, $R^1$ and $R^2$ are taken together to form a 5-membered oxazolidin-2-one ring or a 6-membered 1,3-oxazinan-2-one ring, wherein the ring is optionally substituted or fused to an optionally substituted carbocyclyl, optionally substituted heterocyclyl, optionally substituted aryl, or optionally substituted heteroaryl ring.

In certain embodiments, $R^1$ and $R^2$ are taken together to form an optionally substituted 5-membered oxazolidin-2-one ring (i.e., a monocyclic ring system).

In certain embodiments, $R^1$ and $R^2$ are taken together form a polycyclic ring system, e.g., $R^1$ and $R^2$ are taken together form an optionally substituted 5-membered oxazolidin-2-one ring fused to an optionally substituted carbocyclyl, optionally substituted heterocyclyl, optionally substituted aryl, or optionally substituted heteroaryl ring. In certain embodiments, $R^1$ and $R^2$ are taken together to form an optionally substituted 5-membered oxazolidin-2-one ring fused to an optionally substituted carbocyclyl ring. In certain embodiments, $R^1$ and $R^2$ are taken together to form an optionally substituted 5-membered oxazolidin-2-one ring fused to an optionally substituted heterocyclyl ring. In certain embodiments, $R^1$ and $R^2$ are taken together to form an optionally substituted 5-membered oxazolidin-2-one ring fused to an optionally substituted aryl ring, e.g., fused to an optionally substituted phenyl ring. In certain embodiments, $R^1$ and $R^2$ are taken together to form an optionally substituted 5-membered oxazolidin-2-one ring fused to a substituted phenyl ring, e.g., a monosubstituted, disubstituted, trisubstituted, or tetrasubstituted phenyl ring. In certain embodiments, $R^1$ and $R^2$ are taken together to form an optionally substituted 5-membered oxazolidin-2-one ring fused to a monosubstituted phenyl ring, e.g., substituted at the ortho, meta, or para position of the phenyl ring relative to the oxygen of the fused oxazolidin-2-one ring. In certain embodiments, $R^1$ and $R^2$ are taken together to form an optionally substituted 5-membered oxazolidin-2-one ring fused to a disubstituted phenyl ring, e.g., substituted at the 1,2-, the 1,3-, the 1,4-, the 2,3-, the 3,4-, or the 2,4-positions of the phenyl ring relative to the oxygen of the fused oxazolidin-2-one ring. In certain embodiments, $R^1$ and $R^2$ are taken together to form an optionally substituted 5-membered oxazolidin-2-one ring fused to a trisubstituted phenyl ring, e.g., substituted at the 1,2,3-, the 1,2,4-, or the 2,3,4-, positions of the phenyl ring relative to the oxygen of the fused oxazolidin-2-one ring. In certain embodiments, $R^1$ and $R^2$ are taken together to form an optionally substituted 5-membered oxazolidin-2-one ring fused to a tetrasubstituted phenyl ring. In certain embodiments, $R^1$ and $R^2$ are taken together to form an optionally substituted 5-membered oxazolidin-2-one ring fused to an optionally substituted heteroaryl ring, e.g., fused to an optionally substituted pyridinyl ring.

In certain embodiments, $R^1$ and $R^2$ are taken together to form an optionally substituted 6-membered 1,3-oxazinan-2-one ring (i.e., a monocyclic ring system).

In certain embodiments, $R^1$ and $R^2$ are taken together to form a polycyclic ring system, e.g., a 6-membered 1,3-oxazinan-2-one ring fused to an optionally substituted carbocyclyl, optionally substituted heterocyclyl, optionally substituted aryl, or optionally substituted heteroaryl ring. In certain embodiments, $R^1$ and $R^2$ are taken together to form a 6-membered 1,3-oxazinan-2-one ring fused to an optionally substituted carbocyclyl ring. In certain embodiments, $R^1$ and $R^2$ are taken together to form a 6-membered 1,3-oxazinan-2-one ring fused to an optionally substituted heterocyclyl ring. In certain embodiments, $R^1$ and $R^2$ are taken together to form a 6-membered 1,3-oxazinan-2-one ring fused to an optionally substituted aryl ring, e.g., fused to an optionally substituted phenyl ring. In certain embodiments, $R^1$ and $R^2$ are taken together to form an optionally substituted 6-membered 1,3-oxazinan-2-one ring fused to a substituted phenyl ring, e.g., a monosubstituted, disubstituted, trisubstituted, or tetrasubstituted phenyl ring. In certain embodiments, $R^1$ and $R^2$ are taken together to form an optionally substituted 6-membered 1,3-oxazinan-2-one ring fused to a monosubstituted phenyl ring, e.g., substituted at the ortho, meta, or para position of the phenyl ring relative to the oxygen of the fused 1,3-oxazinan-2-one ring. In certain embodiments, $R^1$ and $R^2$ are taken together to form an optionally substituted 6-membered 1,3-oxazinan-2-one ring fused to a disubstituted phenyl ring, e.g., substituted at the 1,2-, the 1,3-, the 1,4-, the 2,3-, the 3,4-, or the 2,4-positions of the phenyl ring relative to the oxygen of the fused 1,3-oxazinan-2-one ring. In certain embodiments, $R^1$ and R² are taken together to form an optionally substituted 6-membered 1,3-oxazinan-2-one ring fused to a trisubstituted phenyl ring, e.g., substituted at the 1,2,3-, the 1,2,4-, or the 2,3,4-, positions of the phenyl ring relative to the oxygen of the fused 1,3-oxazinan-2-one ring. In certain embodiments, R¹ and R² are taken together to form an optionally substituted 6-membered 1,3-oxazinan-2-one ring fused to a tetrasubstituted phenyl ring. In certain embodiments, R¹ and R² are taken together to form a 6-membered 1,3-oxazinan-2-one ring fused to an optionally substituted heteroaryl ring, e.g., fused to an optionally substituted pyridinyl ring.

In any of the embodiments described herein, $R^1$, $R^2$, and the monocyclic or polycyclic (fused) ring system formed therefrom, is defined as optionally substituted. In certain embodiments, $R^1$ and/or $R^2$, or the monocyclic or polycyclic (fused) ring system formed therefrom, is unsubstituted. However, in certain embodiments, $R^1$ and/or $R^2$, or the monocyclic or polycyclic (fused) ring system formed therefrom, is substituted with one or more $R^4$ substituents selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{41}$, —$N(R^{42})_2$, —$SR^{41}$, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{42})OR^{41}$, —$SC(=NR^{42})SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, —$SC(=S)N(R^{42})_2$, —$S(=O)R^{41}$, —$SO_2R^{41}$, —$NR^{42}SO_2R^{41}$, —$SO_2N(R^{42})_2$, —CN, —SCN, and —$NO_2$, wherein each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{42}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{42}$ groups are joined to form an optionally substituted heterocyclic ring.

In certain embodiments, $R^1$ and/or $R^2$, or the ring system formed therefrom, comprises at least one $R^4$ substituent, e.g., for example, one, two, three, four, or five $R^4$ groups. In certain embodiments, $R^1$ and/or $R^2$, or the ring system formed therefrom, comprises one $R^4$ substituent.

In certain embodiments, at least one $R^4$ is an electron-withdrawing group, e.g., a substituent which pulls electron density away from the parent molecule (e.g., a ring system) and/or stabilizes anions or electron rich structures. Exemplary $R^4$ electron-withdrawing groups include, but are not limited to, halogen, —$C(=O)R^{41}$, —$C(=O)OR^{41}$, —$C(=O)SR^{41}$, —$C(=O)N(R^{42})_2$, —$OC(=O)R^{41}$, —$OC(=O)OR^{41}$, —$OC(=O)SR^{41}$, —$OC(=O)N(R^{42})_2$, —$NR^{42}C(=O)R^{42}$, —$NR^{42}C(=O)OR^{41}$, —$NR^{42}C(=O)SR^{41}$, —$NR^{42}C(=O)N(R^{42})_2$, —$SC(=O)R^{41}$, —$SC(=O)OR^{41}$, —$SC(=O)SR^{41}$, —$SC(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$OC(=NR^{42})R^{41}$, —$OC(=NR^{42})OR^{41}$, —$OC(=NR^{42})SR^{41}$, —$OC(=NR^{42})N(R^{42})_2$, —$NR^{42}C(=NR^{42})R^{42}$, —$NR^{42}C(=NR^{42})OR^{41}$, —$NR^{42}C(=NR^{42})SR^{41}$, —$NR^{42}C(=NR^{42})N(R^{42})_2$, —$SC(=NR^{42})R^{41}$, —$SC(=NR^{42})OR^{41}$, —$SC(=NR^{42})SR^{41}$, —$SC(=NR^{42})N(R^{42})_2$, —$C(=S)R^{41}$, —$C(=S)OR^{41}$, —$C(=S)SR^{41}$, —$C(=S)N(R^{42})_2$, —$OC(=S)R^{41}$, —$OC(=S)OR^{41}$, —$OC(=S)SR^{41}$, —$OC(=S)N(R^{42})_2$, —$NR^{42}C(=S)R^{42}$, —$NR^{42}C(=S)OR^{41}$, —$NR^{42}C(=S)SR^{41}$, —$NR^{42}C(=S)N(R^{42})_2$, —$SC(=S)R^{41}$, —$SC(=S)OR^{41}$, —$SC(=S)SR^{41}$, and —$SC(=S)N(R^{42})_2$. In certain embodiments, at least one $R^4$ is selected from the group consisting of —$C(=O)R^{41}$, —$C(=O)OR^{41}$, —$C(=O)SR^{41}$, —$C(=O)N(R^{42})_2$, —$C(=NR^{42})R^{41}$, —$C(=NR^{42})OR^{41}$, —$C(=NR^{42})SR^{41}$, —$C(=NR^{42})N(R^{42})_2$, —$C(=S)R^{41}$, —$C(=S)OR^{41}$, —$C(=S)SR^{41}$, and —$C(=S)N(R^{42})_2$. In certain embodiments, at least one $R^4$ is selected from the group consisting of —$C(=O)R^{41}$, —$C(=O)OR^{41}$, —$C(=O)SR^{41}$, and —$C(=O)N(R^{42})_2$. In certain embodiments, at least one $R^4$ is selected from the group consisting of —$C(=NR^{42})R^{41}$, —$C(=NR^{42})OR^{41}$, —$C(=NR^{42})SR^{41}$, and —$C(=NR^{42})N(R^{42})_2$. In certain embodiments, at least one $R^4$ is selected from the group consisting of —$C(=S)R^{41}$, —$C(=S)OR^{41}$, —$C(=S)SR^{41}$, and —$C(=S)N(R^{42})_2$. In certain embodiments, at least one $R^4$ is selected from the group consisting of —$C(=O)R^{41}$, —$C(=O)OR^{41}$, —$C(=O)SR^{41}$, and —$C(=O)N(R^{42})_2$. In certain embodiments, at least one $R^4$ is selected from the group consisting of —$C(=O)R^{41}$, —$C(=O)OR^{41}$, and —$C(=O)N(R^{42})_2$. In certain embodiments, at least one $R^4$ is selected from the group consisting of —$C(=O)R^{41}$, —$C(=NR^{42})R^{41}$, and —$C(=S)R^{41}$. In certain embodiments, at least one $R^4$ is selected from the group consisting of —$C(=O)R^{41}$ and —$C(=O)OR^{41}$. In certain embodiments, at least one $R^4$ is —$C(=O)R^{41}$.

In certain embodiments of $R^4$, each occurrence of $R^{41}$ is independently hydrogen, optionally substituted $C_{1-6}$ alkyl, optionally substituted $C_6$ aryl, or optionally substituted 5-6 membered heteroaryl; and each occurrence of $R^{42}$ is independently hydrogen, optionally substituted $C_{1-6}$ alkyl, optionally substituted $C_6$ aryl, optionally substituted 5-6 membered heteroaryl, or an amino protecting group, or two $R^{A2}$ groups are joined to form an optionally substituted 5-6 membered heterocyclic ring. In certain embodiments of $R^A$, each occurrence of $R^{A1}$ is independently hydrogen or optionally substituted $C_1$ alkyl (e.g., —$CH_3$, —$CH_2F$, —$CHF_2$, —$CF_3$). In certain embodiments of $R^A$, each occurrence of $R^{A2}$ is independently hydrogen, optionally substituted $C_1$ alkyl, or an amino protecting group.

As generally defined above, $R^3$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, $R^3$ is optionally substituted alkyl, e.g., $C_{1-10}$ alkyl. In certain embodiments, $R^3$ is optionally substituted $C_{1-8}$ alkyl, optionally substituted $C_{1-6}$ alkyl, optionally substituted $C_{1-4}$ alkyl, optionally substituted $C_{1-2}$ alkyl, optionally substituted $C_{2-8}$ alkyl, optionally substituted $C_{2-6}$ alkyl, or optionally substituted $C_{2-4}$ alkyl.

In certain embodiments, $R^3$ is optionally substituted alkenyl, e.g., $C_{2-10}$ alkenyl. In certain embodiments, $R^3$ is optionally substituted $C_{2-8}$ alkenyl, optionally substituted $C_{2-6}$ alkenyl, optionally substituted $C_{2-4}$ alkenyl, or optionally substituted $C_{2-3}$ alkenyl.

In certain embodiments, $R^3$ is optionally substituted alkynyl, e.g., $C_{2-10}$ alkynyl. In certain embodiments, $R^3$ is optionally substituted $C_{2-8}$ alkynyl, optionally substituted $C_{2-6}$ alkynyl, optionally substituted $C_{2-4}$ alkynyl, or optionally substituted $C_{2-3}$ alkynyl.

In certain embodiments, $R^3$ is optionally substituted carbocyclyl, e.g., $C_{3-10}$ carbocyclyl. In certain embodiments, $R^3$ is optionally substituted $C_{3-8}$ carbocyclyl, optionally substituted $C_{4-8}$ carbocyclyl, optionally substituted $C_{5-8}$ carbocyclyl, optionally substituted $C_{5-7}$ carbocyclyl, or optionally substituted $C_{5-6}$ carbocyclyl.

In certain embodiments, $R^3$ is optionally substituted heterocyclyl, e.g., a 5- to 10-membered optionally substituted heterocyclyl. In certain embodiments, $R^3$ is a 5- to 8-membered optionally substituted heterocyclyl, a 5- to 7-membered optionally substituted heterocyclyl, or a 5- to 6-membered optionally substituted heterocyclyl.

In certain embodiments, $R^3$ is optionally substituted aryl or optionally substituted heteroaryl.

In certain embodiments, $R^3$ is optionally substituted aryl, e.g., $C_6$ aryl or $C_{1-10}$ aryl. In certain embodiments, $R^3$ is optionally substituted $C_6$ aryl (i.e., phenyl). In certain embodiments, $R^1$ is optionally substituted $C_{10}$ aryl (i.e., napthyl). In certain embodiments, $R^3$ is an optionally substituted aryl ring, e.g., an optionally substituted phenyl ring. In certain embodiments, $R^3$ is a substituted phenyl ring, e.g., a monosubstituted, disubstituted, trisubstituted, or tetrasubstituted phenyl ring. In certain embodiments, $R^3$ is a monosubstituted phenyl ring, e.g., substituted at the ortho, meta, or para position of the phenyl ring relative to the point of attachment. In certain embodiments, $R^3$ is a disubstituted phenyl ring, e.g., substituted at the 1,2-, the 1,3-, the 1,4-, the 2,3-, the 3,4-, or the 2,4-positions of the phenyl ring relative to the point of attachment. In certain embodiments, $R^3$ is a trisubstituted phenyl ring, e.g., substituted at the 1,2,3-, the 1,2,4-, or the 2,3,4-, positions of the phenyl ring relative to the point of attachment. In certain embodiments, $R^3$ is a tetrasubstituted phenyl ring. In certain embodiments, $R^3$ is optionally substituted heteroaryl, e.g., a 5- to 10-membered optionally substituted heteroaryl. In certain embodiments, $R^3$ is a 5-membered optionally substituted heteroaryl. In certain embodiments, $R^3$ is a 6-membered optionally substituted heteroaryl, e.g., optionally substituted pyridinyl.

In any of the above described embodiments, $R^3$ is defined as optionally substituted. In certain embodiments, $R^3$ is unsubstituted. However, in certain embodiments, $R^3$ is alkyl, alkenyl, alkynyl, carbocyclyl, heterocyclyl, aryl, or heteroaryl substituted with one or more $R^B$ substituents selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{B1}$, —$N(R^{B2})_2$, —$SR^{B1}$, —$C(=O)R^{B1}$, —$C(=O)OR^{B1}$, —$C(=O)SR^{B1}$, —$C(=O)N(R^{B2})_2$, —$OC(=O)R^{B1}$, —$OC(=O)OR^{B1}$, —$OC(=O)SR^{B1}$, —$OC(=O)N(R^{B2})_2$, —$NR^{B2}C(=O)R^{B2}$, —$NR^{B2}C(=O)OR^{B1}$, —$NR^{B2}C(=O)SR^{B1}$, —$NR^{B2}C(=O)N(R^{B2})_2$, —$SC(=O)R^{B1}$, —$SC(=O)OR^{B1}$, —$SC(=O)SR^{B1}$, —$SC(=O)N(R^{B2})_2$, —$C(=NR^{B2})R^{B1}$, —$C(=NR^{B2})OR^{B1}$, —$C(=NR^{B2})SR^{B1}$, —$C(=NR^{B2})N(R^{B2})_2$, —$OC(=NR^{B2})R^{B1}$, —$OC(=NR^{B2})OR^{B1}$, —$OC(=NR^{B2})SR^{B1}$, —$OC(=NR^{B2})N(R^{B2})_2$, —$NR^{B2}C(=NR^{B2})R^{B2}$, —$NR^{B2}C(=NR^{B2})OR^{B1}$, —$NR^{B2}C(=NR^{B2})SR^{B1}$, —$NR^{B2}C(=NR^{B2})N(R^{B2})_2$, —$SC(=NR^{B2})R^{B1}$, —$SC(=NR^{B2})OR^{B1}$, —$SC(=NR^{B2})SR^{B1}$, —$SC(=NR^{B2})N(R^{B2})_2$, —$C(=S)R^{B1}$, —$C(=S)OR^{B1}$, —$C(=S)SR^{B1}$, —$C(=S)N(R^{B2})_2$, —$OC(=S)R^{B1}$, —$OC(=S)OR^{B1}$, —$OC(=S)SR^{B1}$, —$OC(=S)N(R^{B2})_2$, —$NR^{B2}C(=S)R^{B2}$, —$NR^{B2}C(=S)OR^{B1}$, —$NR^{B2}C(=S)SR^{B1}$, —$NR^{B2}C(=S)N(R^{B2})_2$, —$SC(=S)R^{B1}$, —$SC(=S)OR^{B1}$, —$SC(=S)SR^{B1}$, —$SC(=S)N(R^{B2})_2$, —$S(=O)R^{B1}$, —$SO_2R^{B1}$, —$NR^{B2}SO_2R^{B1}$, —$SO_2N(R^{B2})_2$, —CN, —SCN, and —$NO_2$, wherein each occurrence of $R^{B1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{B2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{B2}$ groups are joined to form a heterocyclic ring.

In certain embodiments, $R^3$ comprises at least one $R^B$ substituent, e.g., one, two, three, four, or five $R^B$ groups. In certain embodiments, $R^3$ comprises one $R^B$ substituent. In certain embodiments, at least one $R^B$ is an electron-donating group, e.g., a substituent which adds electron density to the parent molecule (e.g., a ring system) and/or stabilizes cations or electron poor structures. Exemplary $R^B$ electron-donating groups include optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{B1}$, —$N(R^{B2})_2$, and —$SR^{B1}$. In certain embodiments, at least one $R^B$ substituent is selected from the group consisting of —$OR^{B1}$, —$N(R^{B2})_2$, and —$SR^{B1}$. In certain embodiments, at least one $R^B$ is —$OR^{B1}$. In certain embodiments, at least one $R^B$ is —$N(R^{B2})_2$. In certain embodiments, at least one $R^B$ is —$SR^{B1}$.

In certain embodiments of $R^B$, each occurrence of $R^{B1}$ is independently hydrogen, optionally substituted $C_{1-6}$ alkyl, optionally substituted $C_6$ aryl, or optionally substituted 5-6 membered heteroaryl; and each occurrence of $R^{B2}$ is independently hydrogen, optionally substituted $C_{1-6}$ alkyl, optionally substituted $C_6$ aryl, optionally substituted 5-6 membered heteroaryl, or an amino protecting group, or two $R^{B2}$ groups are joined to form an optionally substituted 5-6 membered heterocyclic ring. In certain embodiments of $R^B$, each occurrence of $R^{B1}$ is independently hydrogen or optionally substituted $C_1$ alkyl (e.g., —$CH_3$, —$CF_3$). In certain embodiments of $R^B$, each occurrence of $R^{B2}$ is independently hydrogen, optionally substituted $C_1$ alkyl (e.g., —$CH_3$, —$CF_3$), or an amino protecting group.

Various combinations of the above described embodiments of X, Y, $R^1$, $R^2$, $R^3$, $R^A$, and $R^B$ are further contemplated.

For example, in certain embodiments, when $R^1$ and $R^2$ are taken together to form a 5-membered oxazolidin-2-one ring fused to an optionally substituted aryl ring, a provided

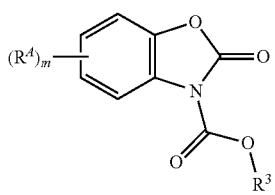
(II-A)

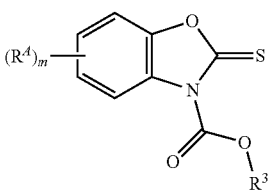
(III-A)

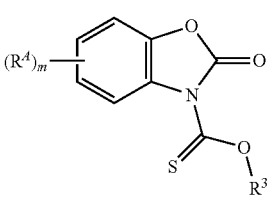
(IV-A)

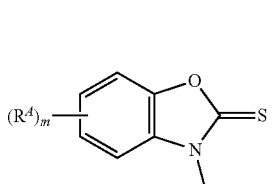
(V-A)

or a pharmaceutically acceptable salt thereof; wherein $R^3$ and $R^A$ are as defined herein, and m is 0 or an integer between 1 and 4, inclusive. In certain embodiments, m is 0. In certain embodiments, m is 1. In certain embodiments, m is 2. In certain embodiments, m is 3. In certain embodiments, m is 4. In certain embodiments, at least one $R^A$ is an electron-withdrawing group, as defined herein. In certain embodiments, at least one $R^A$ is —C(=O)$R^{A1}$. In certain embodiments, at least one $R^A$ is halogen. In certain embodiments, at least one $R^A$ is nitro. In certain embodiments, $R^3$ is optionally substituted aryl or optionally substituted heteroaryl. In certain embodiments, $R^3$ is aryl or heteroaryl substituted with at least one electron-donating group, as defined herein. In certain embodiments, $R^3$ is aryl or heteroaryl substituted with at least one group selected from the group consisting of —$OR^{B1}$, —$N(R^{B2})_2$, and —$SR^{B1}$.

In certain embodiments, when m is 1, a provided compound has any one of the following formulae:

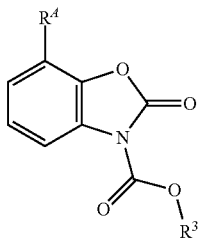
(II-A1)

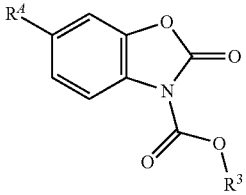
(II-A2)

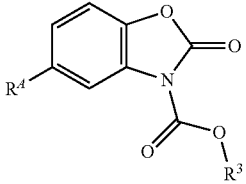
(II-A3)

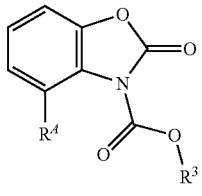
(II-A4)

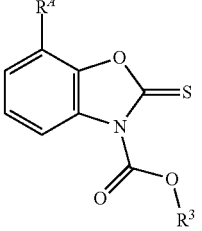
(III-A1)

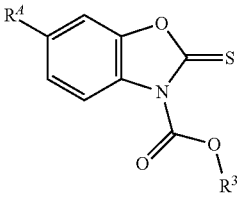
(III-A2)

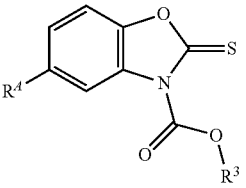
(III-A3)

(III-A4)
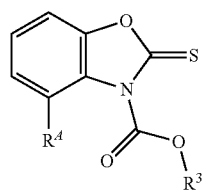

(IV-A1)
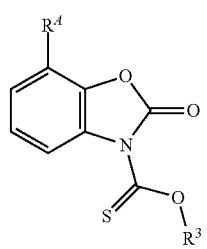

(IV-A2)
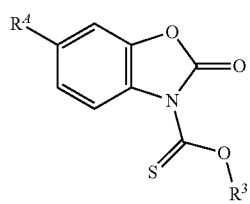

(IV-A3)
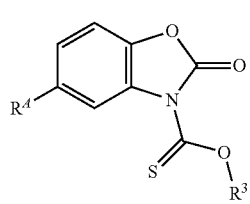

(IV-A4)
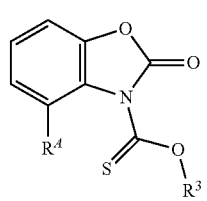

(V-A1)
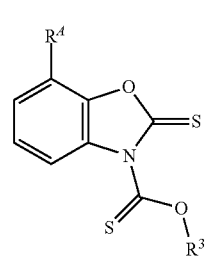

(V-A2)
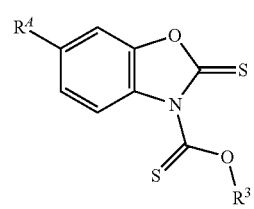

(V-A3)
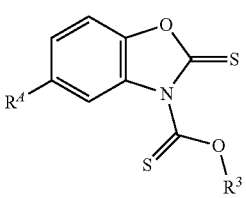

(V-A4)
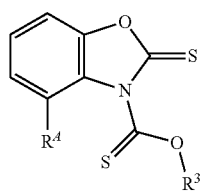

or a pharmaceutically acceptable salt thereof; wherein $R^3$ and $R^4$ are as defined herein. In certain embodiments, $R^4$ is an electron-withdrawing group, as defined herein. In certain embodiments, $R^4$ is —C(=O)$R^{A1}$. In certain embodiments, $R^3$ is optionally substituted aryl or optionally substituted heteroaryl. In certain embodiments, $R^3$ is unsubstituted aryl or unsubstituted heteroaryl. However, in certain embodiments, $R^3$ is a substituted aryl or substituted heteroaryl, e.g., substituted with at least one electron-donating group, as defined herein. In certain embodiments, $R^3$ is phenyl substituted with at least one group selected from the group consisting of —$OR^{B1}$, —$N(R^{B2})_2$, and —$SR^{B1}$.

In certain embodiments, when m is 2, a provided compound has any one of the formulae:

(II-A5)
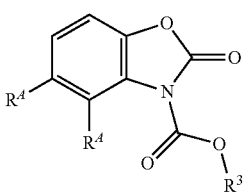

(II-A6)
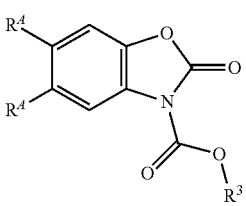

(II-A7)
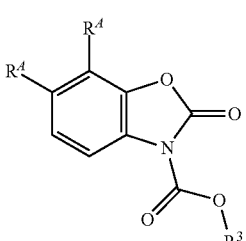

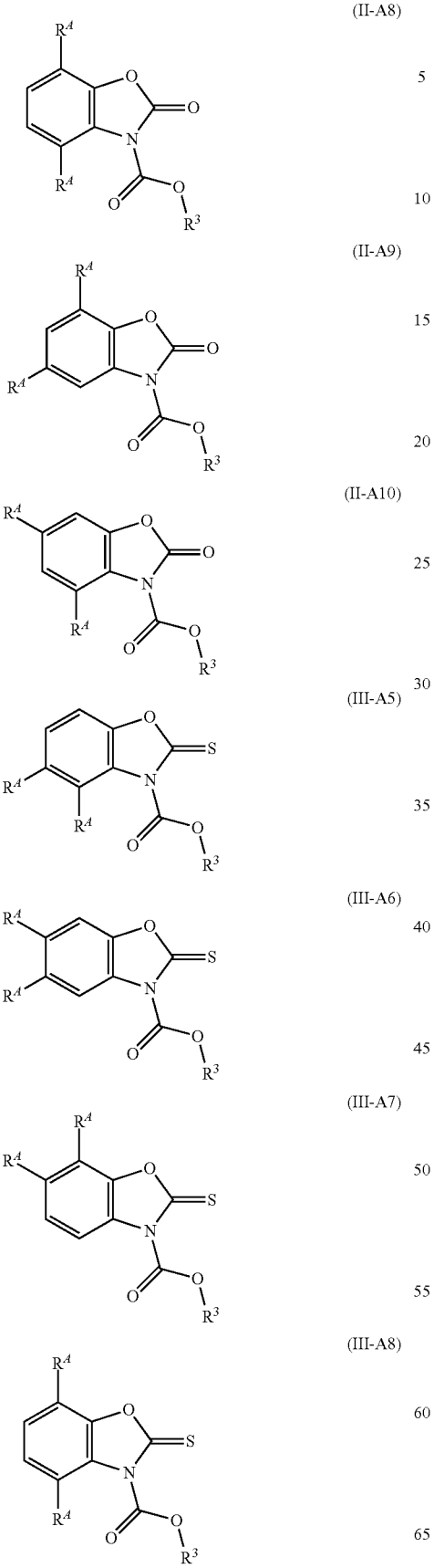
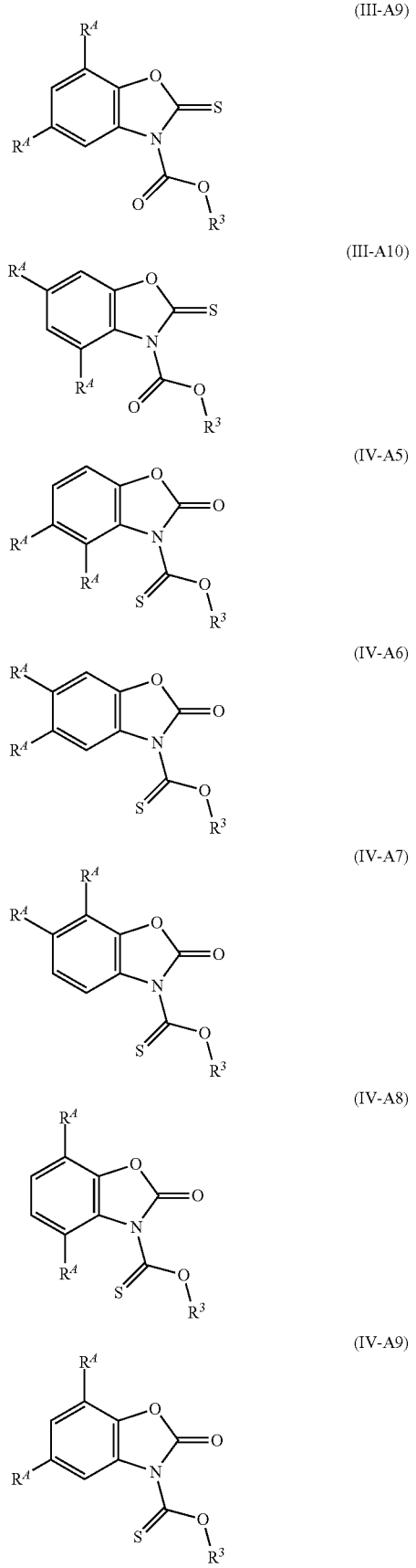

-continued

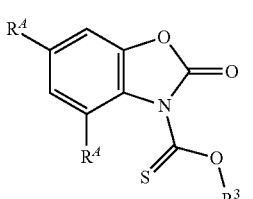
(IV-A-10)

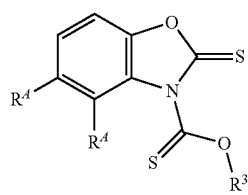
(V-A5)

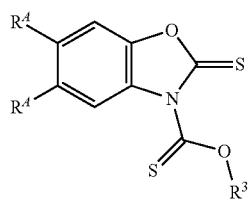
(V-A6)

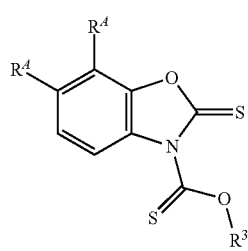
(V-A7)

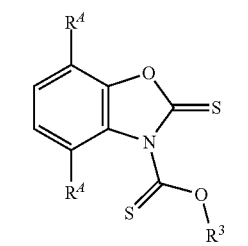
(V-A8)

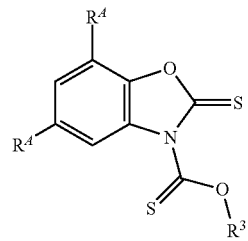
(V-A9)

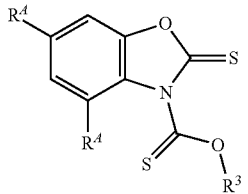
(V-A10)

or a pharmaceutically acceptable salt thereof; wherein $R^3$ and $R^4$ are as defined herein. In certain embodiments, at least one $R^4$ is an electron-withdrawing group, as defined herein. In certain embodiments, at least one $R^4$ is —C(=O)$R^{A1}$. In certain embodiments, at least one $R^4$ is halogen. In certain embodiments, at least one $R^4$ is nitro. In certain embodiments, $R^3$ is optionally substituted aryl or optionally substituted heteroaryl. In certain embodiments, $R^3$ is unsubstituted aryl or unsubstituted heteroaryl. However, in certain embodiments, $R^3$ is a substituted aryl or substituted heteroaryl, e.g., substituted with at least one electron-donating group, as defined herein. In certain embodiments, $R^3$ is phenyl substituted with at least one group selected from the group consisting of —$OR^{B1}$, —$N(R^{B2})_2$, and —$SR^{B1}$.

In certain embodiments, when m is 3, a provided compound has any one of the formulae:

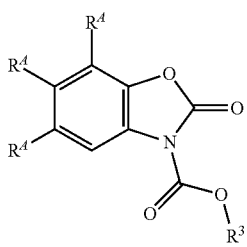
(II-A11)

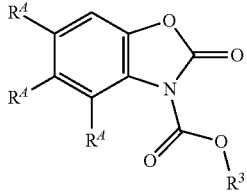
(II-A12)

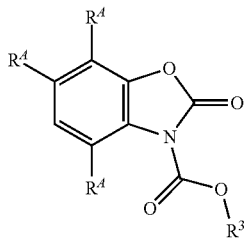
(II-A13)

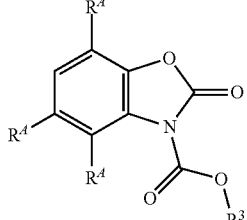
(II-A14)

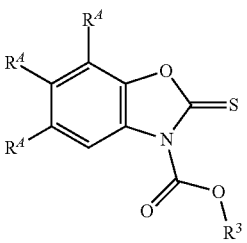
(III-A11)

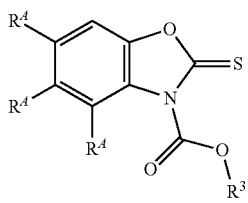 (III-A12)

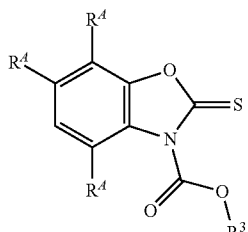 (III-A13)

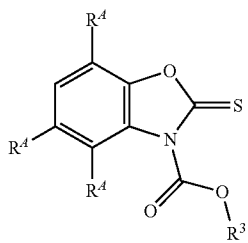 (III-A14)

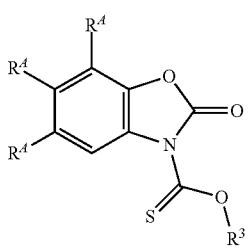 (IV-A11)

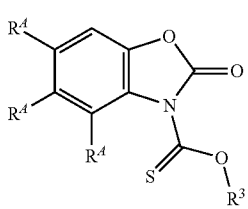 (IV-A12)

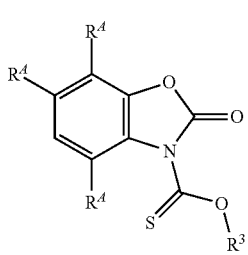 (IV-A13)

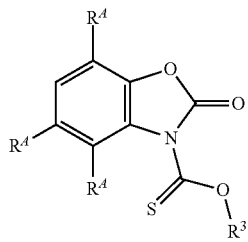 (IV-A14)

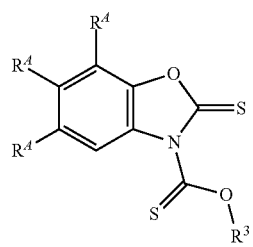 (V-A11)

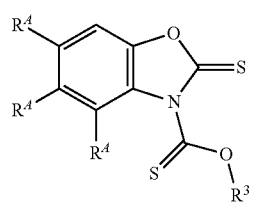 (V-A12)

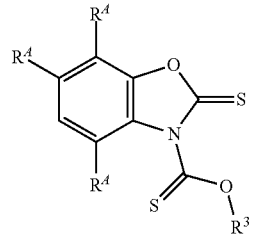 (V-A13)

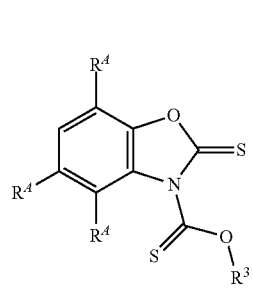 (V-A14)

or a pharmaceutically acceptable salt thereof; wherein $R^3$ and $R^A$ are as defined herein. In certain embodiments, at least one $R^A$ is an electron-withdrawing group, as defined herein. In certain embodiments, at least one $R^A$ is —C(=O)$R^{A1}$. In certain embodiments, at least one $R^A$ is halogen. In certain embodiments, at least one $R^A$ is nitro. In certain embodiments, $R^3$ is optionally substituted aryl or optionally substituted heteroaryl. In certain embodiments, $R^3$ is unsubstituted aryl or unsubstituted heteroaryl. However, in certain embodiments, $R^3$ is a substituted aryl or substituted heteroaryl, e.g., substituted with at least one electron-donating group, as defined herein. In certain embodiments, $R^3$ is phenyl substituted with at least one group selected from the group consisting of —$OR^{B1}$, —$N(R^{B2})_2$, and —$SR^{B1}$.

In certain embodiments, when m is 4, a provided compound has one of the following formulae:

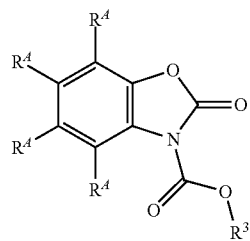
(II-A15)

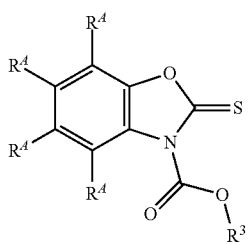
(III-A15)

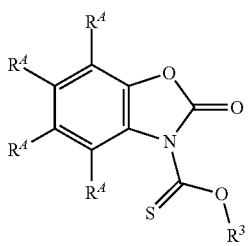
(IV-A15)

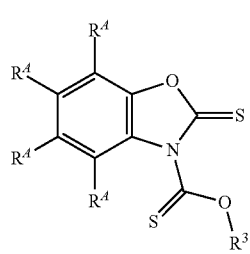
(V-A15)

or a pharmaceutically acceptable salt thereof; wherein $R^3$ and $R^A$ are as defined herein. In certain embodiments, at least one $R^A$ is an electron-withdrawing group, as defined herein. In certain embodiments, at least one $R^A$ is —C(=O)$R^{A1}$. In certain embodiments, at least one $R^A$ is halogen. In certain embodiments, at least one $R^A$ is nitro. In certain embodiments, $R^3$ is optionally substituted aryl or optionally substituted heteroaryl. In certain embodiments, $R^3$ is unsubstituted aryl or unsubstituted heteroaryl. However, in certain embodiments, $R^3$ is a substituted aryl or substituted heteroaryl, e.g., substituted with at least one electron-donating group, as defined herein. In certain embodiments, $R^3$ is phenyl substituted with at least one group selected from the group consisting of —$OR^{B1}$, —$N(R^{B2})_2$, and —$SR^{B1}$.

In certain embodiments, $R^A$ is an electron-withdrawing group ortho to the ring oxygen of the oxazolidin-2-one ring. In certain embodiments, $R^A$ is an electron-withdrawing group meta to the ring oxygen of the oxazolidin-2-one ring. In certain embodiments, $R^A$ is an electron-withdrawing group para to the ring oxygen of the oxazolidin-2-one ring.

In certain embodiments, $R^A$ is an electron-withdrawing group ortho to the ring nitrogen of the oxazolidin-2-one ring. In certain embodiments, $R^A$ is an electron-withdrawing group meta to the ring nitrogen of the oxazolidin-2-one ring. In certain embodiments, $R^A$ is an electron-withdrawing group para to the ring nitrogen of the oxazolidin-2-one ring.

In certain embodiments, when $R^3$ is optionally substituted aryl, a provided compound is of Formula (II-B), (III-B), (IV-B), or (V-B):

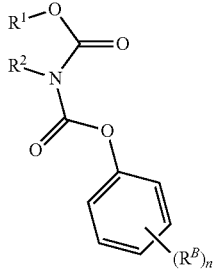
(II-B)

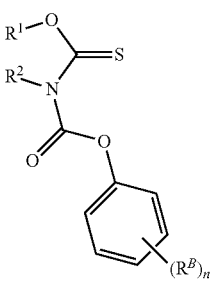
(III-B)

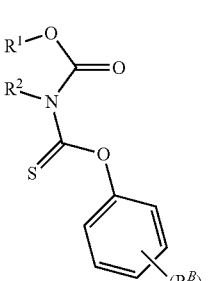
(IV-B)

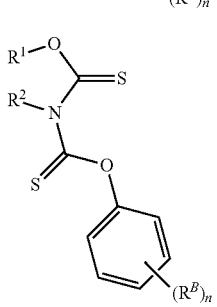
(V-B)

or a pharmaceutically acceptable salt thereof; wherein $R^1$, $R^2$, and $R^B$ are as defined herein, and n is 0 or an integer between 1 and 5, inclusive. In certain embodiments, n is 0. In certain embodiments, n is 1. In certain embodiments, n is 2. In certain embodiments, n is 3. In certain embodiments, n is 4. In certain embodiments, n is 5. In certain embodiments, at least one $R^B$ is an electron-donating group, as defined herein. In certain embodiments, at least one $R^B$ is selected from the group consisting of —$OR^{B1}$, —$N(R^{B2})_2$, and —$SR^{B1}$. In certain embodiments, at least one $R^B$ is —$OR^{B1}$. In certain embodiments, $R^1$ and $R^2$ are taken together to form a 5-membered oxazolidin-2-one ring fused to an optionally substituted aryl ring, e.g., optionally substituted phenyl. In certain embodiments, $R^1$ and $R^2$ are taken together to form a 5-membered oxazolidin-2-one ring fused to a phenyl ring substituted with at least one $R^A$ substituent, as defined herein. At least one $R^A$ is an electron-withdrawing group, as defined herein. In certain embodiments, at least one $R^A$ is —C(=O)$R^{A1}$. In certain embodiments, at least one $R^A$ is halogen. In certain embodiments, at least one $R^A$ is nitro.

In certain embodiments, when n is 1, a provided compound has any one of the following formulae:

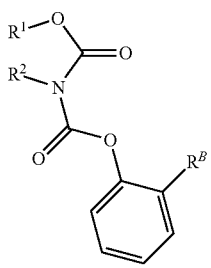
(II-B1)

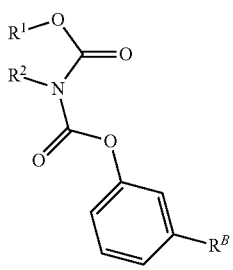
(II-B2)

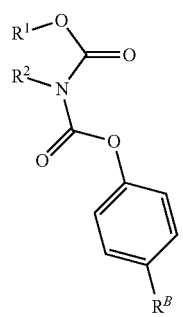
(II-B3)

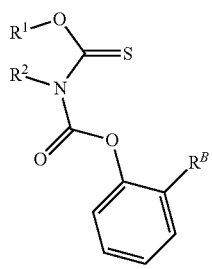
(III-B1)

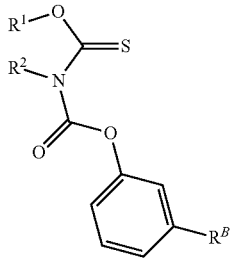
(III-B2)

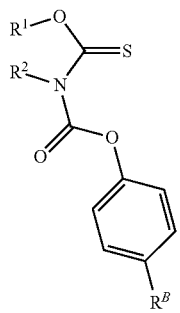
(III-B3)

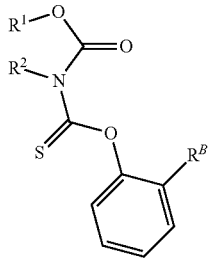
(IV-B1)

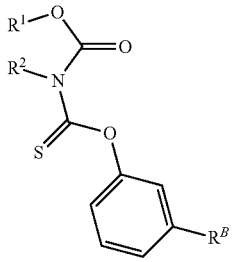
(IV-B2)

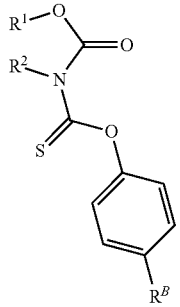
(IV-B3)

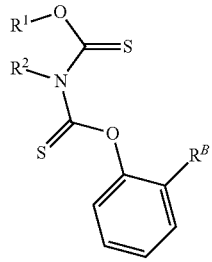
(V-B1)

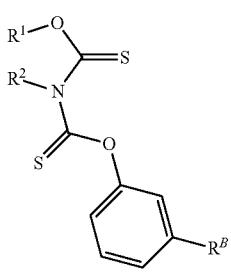
(V-B2)

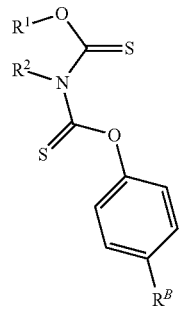
(V-B3)

or a pharmaceutically acceptable salt thereof; wherein $R^1$, $R^2$, and $R^B$ are as defined herein. In certain embodiments, $R^B$ is an electron-donating group, as defined herein. In certain embodiments, $R^B$ is selected from the group consisting of —$OR^{B1}$, —$N(R^{B2})_2$, and —$SR^{B1}$. In certain embodiments, $R^B$ is —$OR^{B1}$. In certain embodiments, $R^1$ and $R^2$ are taken together to form a 5-membered oxazolidin-2-one ring fused to an optionally substituted aryl ring, e.g., optionally substituted phenyl. In certain embodiments, $R^1$ and $R^2$ are taken together to form a 5-membered oxazolidin-2-one ring fused to a phenyl ring substituted with at least one $R^A$ substituent, as defined herein. At least one $R^A$ is an electron-withdrawing group, as defined herein. In certain embodiments, at least one $R^A$ is —C(=O)$R^{A1}$. In certain embodiments, at least one $R^A$ is halogen. In certain embodiments, at least one $R^A$ is nitro.

In certain embodiments, when n is 2, a provided compound has any one of the following formulae:

(II-B4)

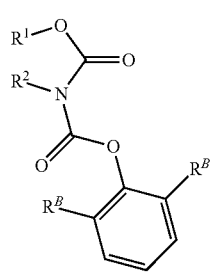

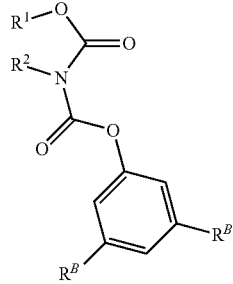
(II-B5)

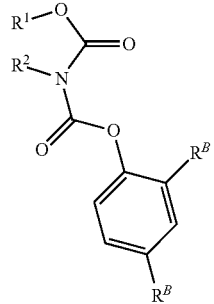
(II-B6)

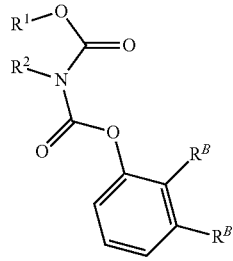
(II-B7)

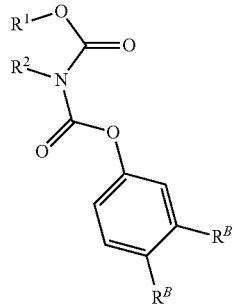
(II-B8)

(III-B4)

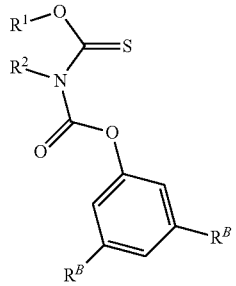 (III-B5)
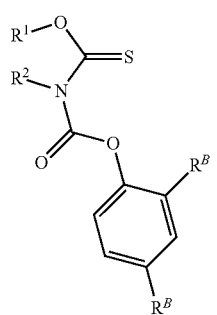 (III-B6)
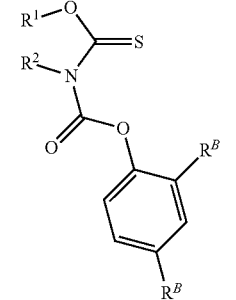 (III-B7)
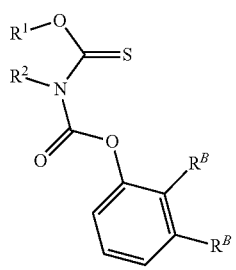 (III-B8)
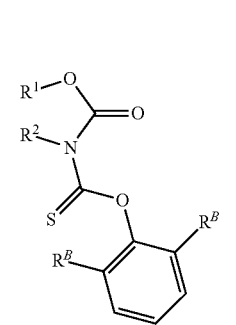 (IV-B4)
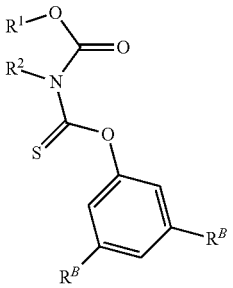 (IV-B5)
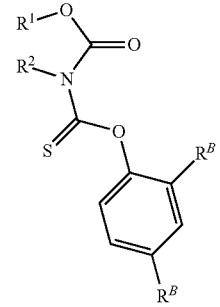 (IV-B6)
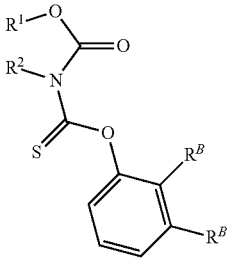 (IV-B7)
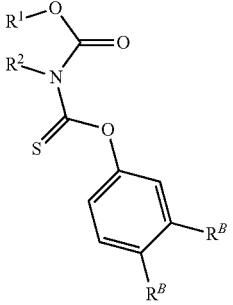 (IV-B8)
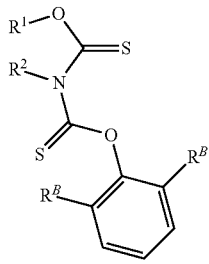 (V-B4)

(V-B5)
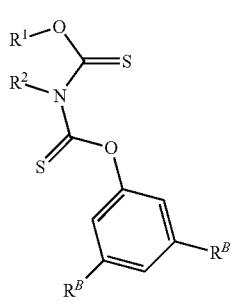

(V-B6)
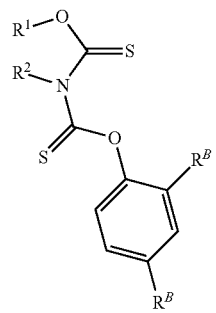

(V-B7)
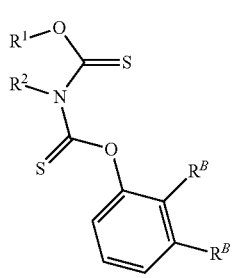

(V-B8)
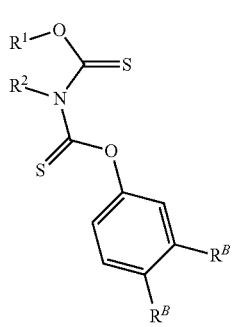

or a pharmaceutically acceptable salt thereof; wherein $R^1$, $R^2$, and $R^B$ are as defined herein. In certain embodiments, at least one $R^B$ is an electron-donating group, as defined herein. In certain embodiments, at least one $R^B$ is selected from the group consisting of —$OR^{B1}$, —$N(R^{B2})_2$, and —SR. In certain embodiments, at least one $R^B$ is —OR. In certain embodiments, $R^1$ and $R^2$ are taken together to form a 5-membered oxazolidin-2-one ring fused to an optionally substituted aryl ring, e.g., optionally substituted phenyl. In certain embodiments, $R^1$ and $R^2$ are taken together to form a 5-membered oxazolidin-2-one ring fused to a phenyl ring substituted with at least one $R^A$ substituent, as defined herein. At least one $R^A$ is an electron-withdrawing group, as defined herein. In certain embodiments, at least one $R^A$ is —C(=O)$R^{A1}$. In certain embodiments, at least one $R^A$ is halogen. In certain embodiments, at least one $R^A$ is nitro.

In certain embodiments, when n is 3, a provided compound has of any one of the following formulae:

(II-B9)
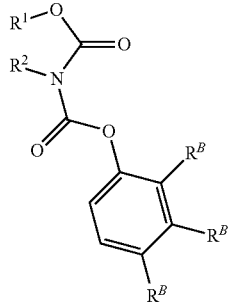

(II-B10)
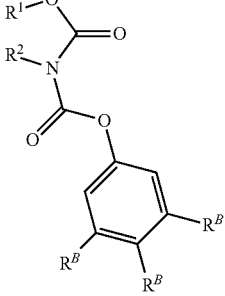

(II-B11)
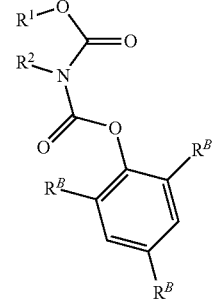

(II-B12)
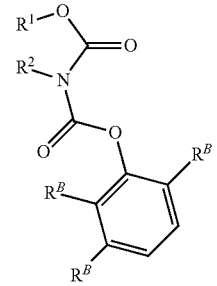

(II-B13)
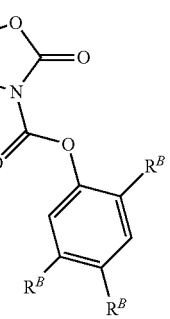

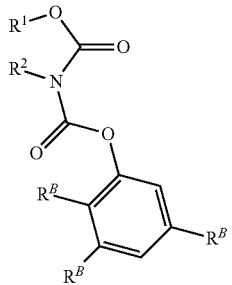 (II-B14)
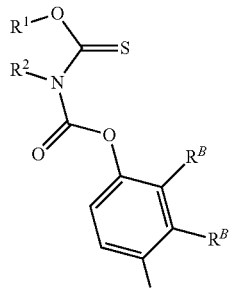 (III-B9)
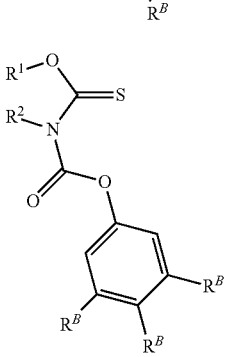 (III-B10)
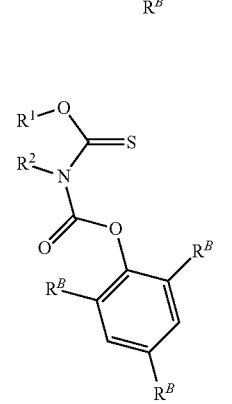 (III-B11)
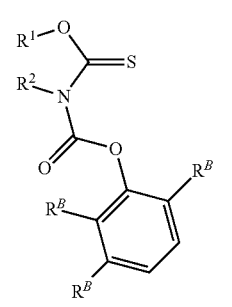 (III-B12)
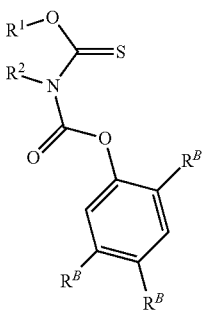 (III-B13)
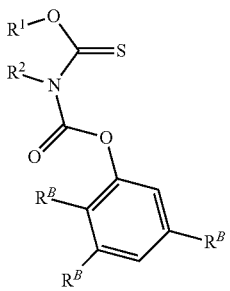 (III-B14)
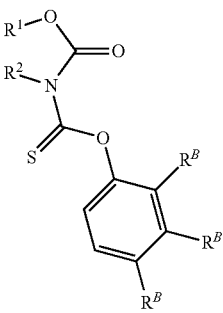 (IV-B9)
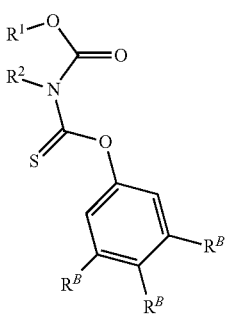 (IV-B10)
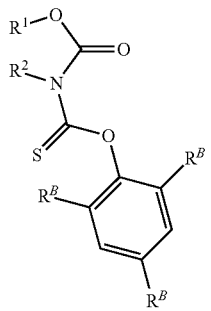 (IV-B11)

(IV-B12)
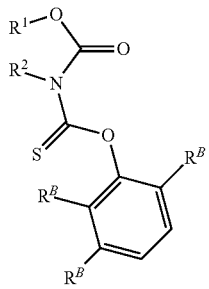

(IV-B13)
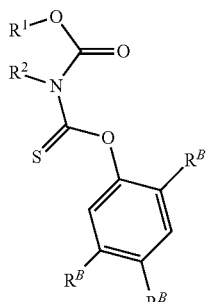

(IV-B14)
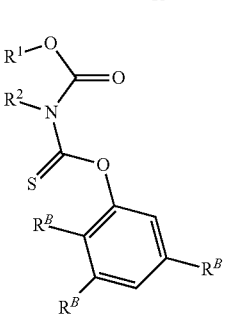

(V-B9)
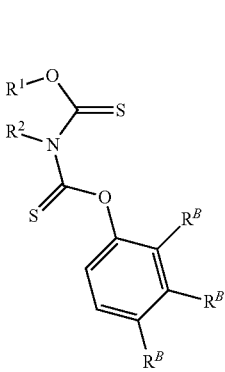

(V-B10)
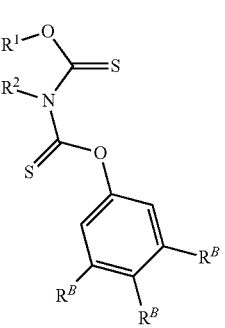

(V-B11)
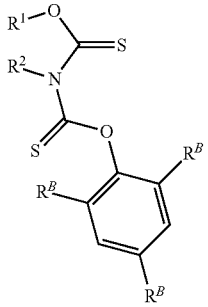

(V-B12)
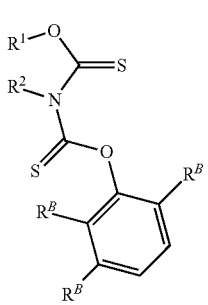

(V-B13)
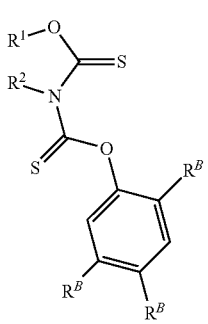

(V-B14)
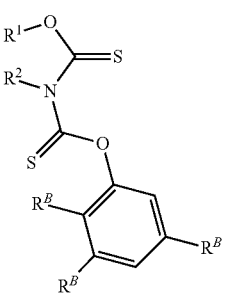

or a pharmaceutically acceptable salt thereof; wherein $R^1$, $R^2$, and $R^B$ are as defined herein. In certain embodiments, at least one $R^B$ is an electron-donating group. In certain embodiments, at least one $R^B$ is selected from the group consisting of —$OR^{B1}$, —$N(R^{B2})_2$, and —$SR^{B1}$. In certain embodiments, at least one $R^B$ is —$OR^{B1}$. In certain embodiments, $R^1$ and $R^2$ are taken together to form a 5-membered oxazolidin-2-one ring fused to an optionally substituted aryl ring, e.g., optionally substituted phenyl. In certain embodiments, $R^1$ and $R^2$ are taken together to form a 5-membered oxazolidin-2-one ring fused to a phenyl ring substituted with at least one $R^A$ substituent, as defined herein. At least one $R^A$ is an electron-withdrawing group, as defined herein. In certain embodiments, at least one $R^A$ is —C(=O)$R^{A1}$ In certain embodiments, at least one $R^A$ is halogen. In certain embodiments, at least one $R^A$ is nitro.

In certain embodiments, when n is 4, a provided compound is of one of the following formulae:

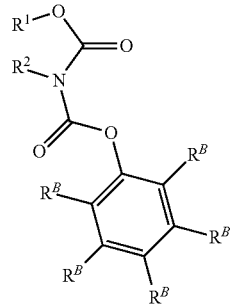
(II-B15)

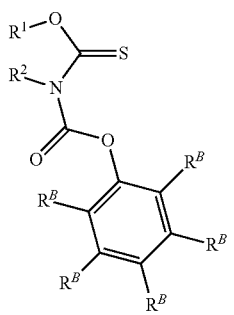
(III-B15)

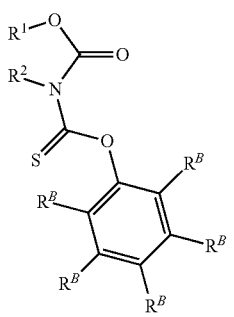
(IV-B15)

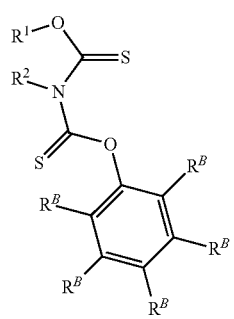
(V-B15)

or a pharmaceutically acceptable salt thereof; wherein $R^1$, $R^2$, and $R^B$ are as defined herein. In certain embodiments, at least one $R^B$ is an electron-donating group. In certain embodiments, at least one $R^B$ is selected from the group consisting of —$OR^{B1}$, —$N(R^{B2})_2$, and —$SR^{B1}$. In certain embodiments, at least one $R^B$ is —$OR^{B1}$. In certain embodiments, $R^1$ and $R^2$ are taken together to form a 5-membered oxazolidin-2-one ring fused to an optionally substituted aryl ring, e.g., optionally substituted phenyl. In certain embodiments, $R^1$ and $R^2$ are taken together to form a 5-membered oxazolidin-2-one ring fused to a phenyl ring substituted with at least one $R^A$ substituent, as defined herein. At least one $R^A$ is an electron-withdrawing group, as defined herein. In certain embodiments, at least one $R^A$ is —$C(=O)R^{A1}$. In certain embodiments, at least one $R^A$ is halogen. In certain embodiments, at least one $R^A$ is nitro.

In certain embodiments, $R^B$ is an ortho electron-donating group. In certain embodiments, $R^B$ is a meta electron-donating group. In certain embodiments, $R^B$ is a para electron-donating group.

In certain embodiments, when $R^1$ and $R^2$ are taken together to form a 5-membered oxazolidin-2-one ring fused to an optionally substituted aryl ring, and $R^3$ is an optionally substituted aryl, a provided compound is of Formula (II-C), (III-C), (IV-C), or (V-C):

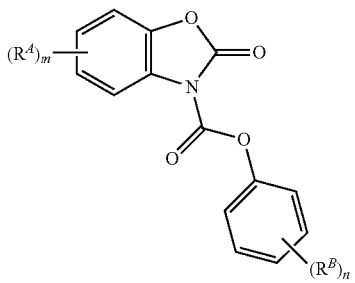
(II-C)

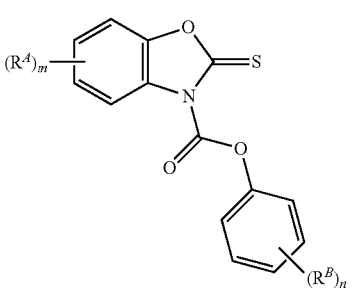
(III-C)

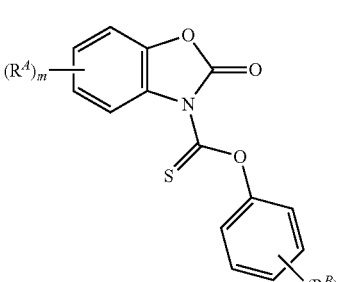
(IV-C)

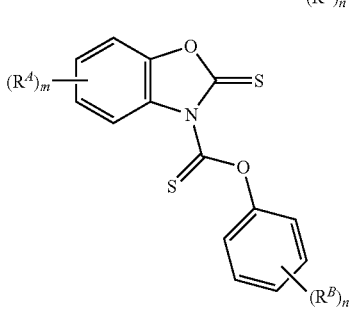
(V-C)

or a pharmaceutically acceptable salt thereof; wherein $R^A$, $R^B$, m, and n are as defined herein. In certain embodiments, at least one $R^B$ is an electron-donating group, as defined herein. In certain embodiments, at least one $R^B$ is selected from the group consisting of —$OR^{B1}$, —$N(R^{B2})_2$, and —SR.

In certain embodiments, at least one $R^B$ is —OR. In certain embodiments, at least one $R^A$ is an electron-withdrawing group, as defined herein. In certain embodiments, at least one $R^A$ is —C(=O)$R^{A1}$. In certain embodiments, at least one $R^A$ is halogen. In certain embodiments, at least one $R^A$ is nitro. In certain embodiments, m is 1. In certain embodiments, n is 1. In certain embodiments, m is 0, and n is 1. In certain embodiments, m is 1, and n is 0. In certain embodiments, m is 1, and n is 1.

In certain embodiments, when m is 1, a provided compound is of any one of the following formulae:

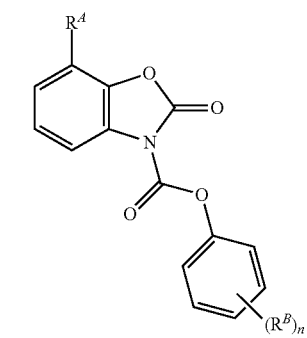
(II-C1)

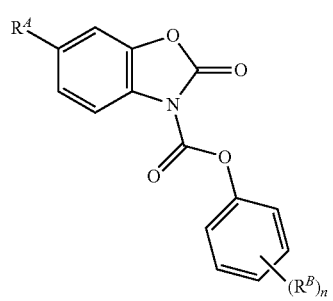
(II-C2)

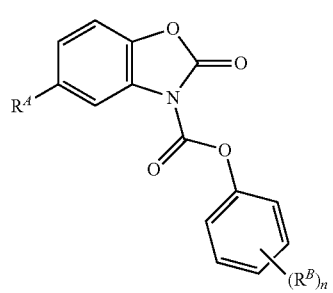
(II-C3)

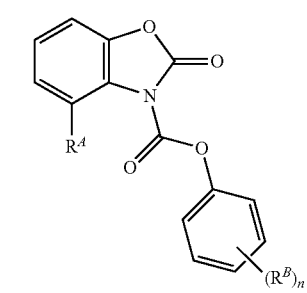
(II-C4)

-continued

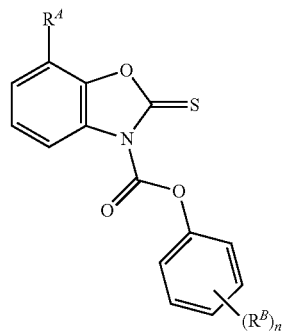
(III-C1)

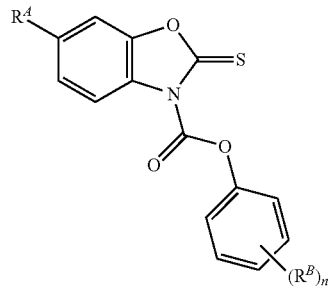
(III-C2)

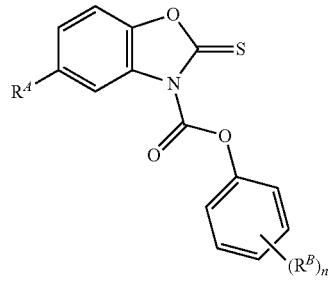
(III-C3)

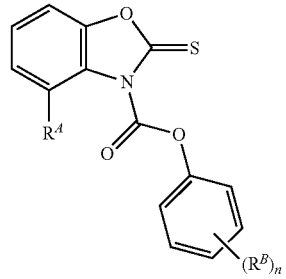
(III-C4)

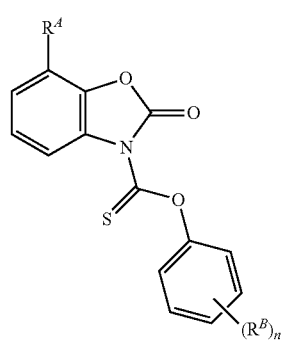
(IV-C1)

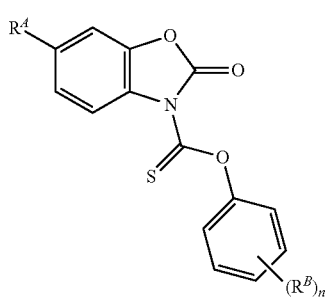
(IV-C2)

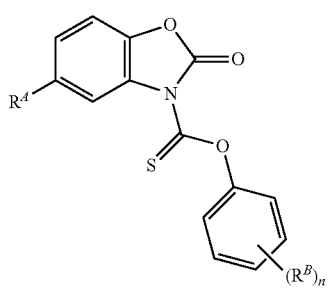
(IV-C3)

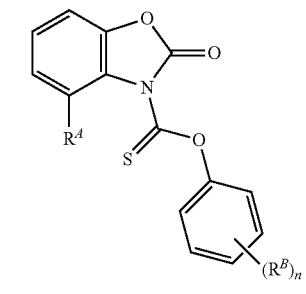
(IV-C4)

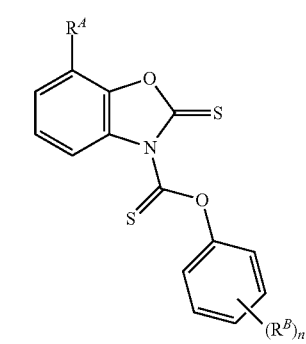
(V-C1)

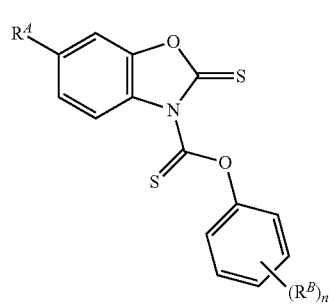
(V-C2)

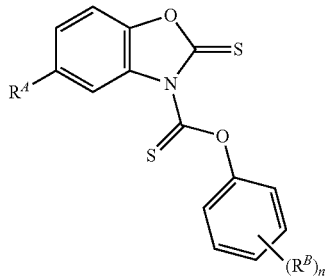
(V-C3)

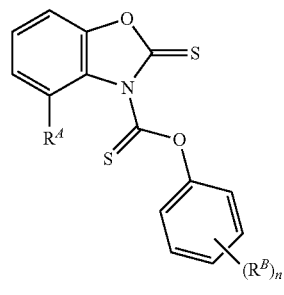
(V-C4)

or a pharmaceutically acceptable salt thereof; wherein $R^A$, $R^B$, and n are as defined herein. In certain embodiments, at least one $R^B$ is an electron-donating group, as defined herein. In certain embodiments, at least one $R^B$ is selected from the group consisting of —$OR^{B1}$, —$N(R^{B2})_2$, and —$SR^{B1}$. In certain embodiments, at least one $R^B$ is —OR. In certain embodiments, $R^A$ is an electron-withdrawing group, as defined herein. In certain embodiments, $R^A$ is —C(=O)$R^{A1}$. In certain embodiments, at least one $R^A$ is halogen. In certain embodiments, at least one $R^A$ is nitro. In certain embodiments, n is 1.

In certain embodiments, when n is 1, a provided compound has of any one of the following formulae:

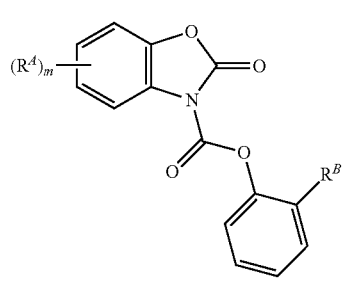
(II-C5)

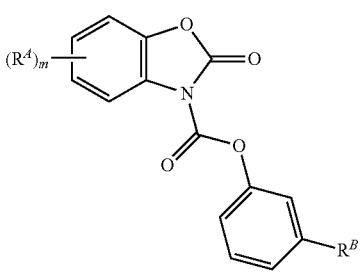
(II-C6)

(II-C7)
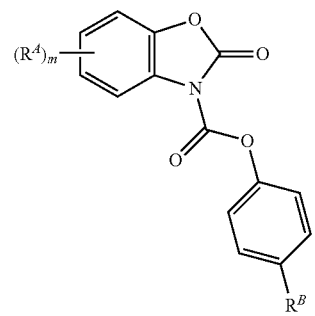

(III-C5)
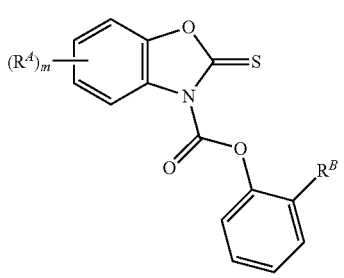

(III-C6)
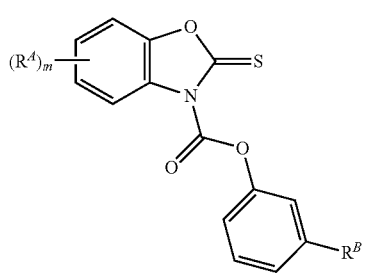

(III-C7)
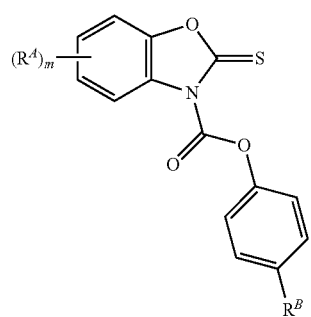

(IV-C5)
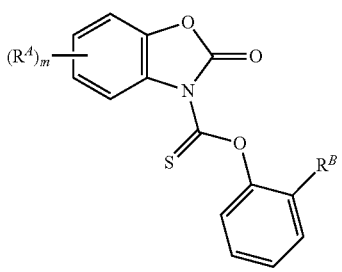

(IV-C6)
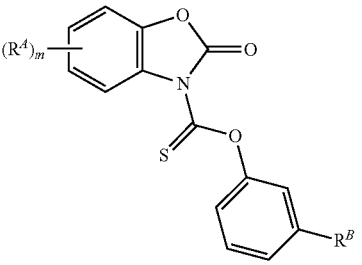

(IV-C7)
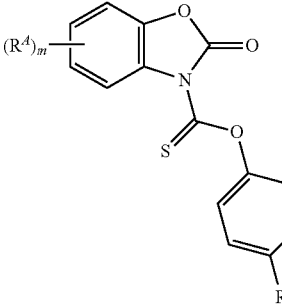

(V-C5)
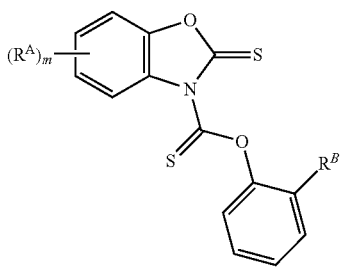

(V-C6)
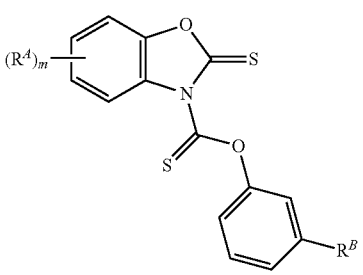

(V-C7)
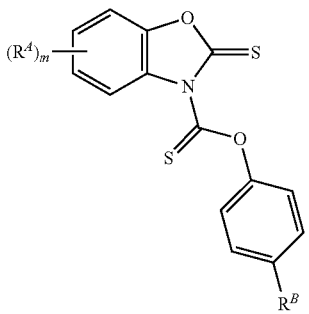

or a pharmaceutically acceptable salt thereof; wherein $R^A$, $R^B$, and m are as defined herein. In certain embodiments, $R^B$ is an electron-donating group, as defined herein. In certain embodiments, $R^B$ is selected from the group consisting of $-OR^{B1}$, $-N(R^{B2})_2$, and $-SR^{B1}$. In certain embodiments, $R^B$ is $-OR^{B1}$. In certain embodiments, at least one $R^A$ is an electron-withdrawing group, as defined herein. In certain embodiments, at least one $R^A$ is —C(=O)$R^{A1}$ In certain embodiments, at least one $R^A$ is halogen. In certain embodiments, at least one $R^A$ is nitro. In certain embodiments, m is 1.
In certain embodiments, when m is 1 and n is 1, a provided compound has of any one of the following formulae:
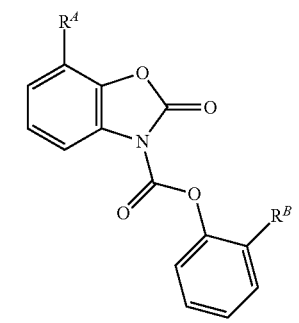
(II-C8)
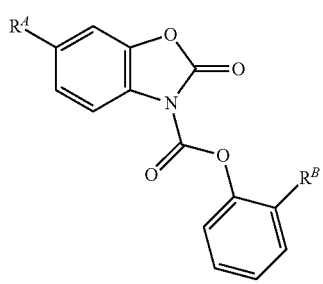
(II-C9)
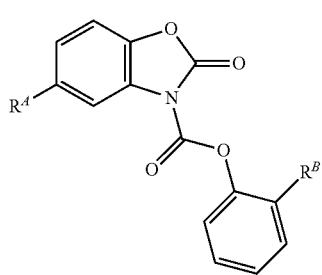
(II-C10)
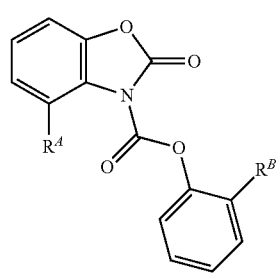
(II-C11)
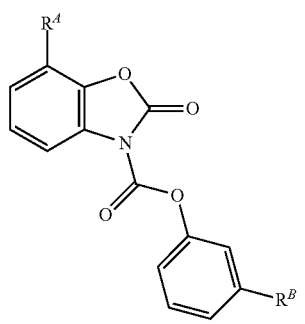
(II-C12)
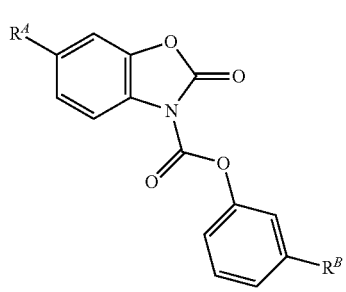
(II-C13)
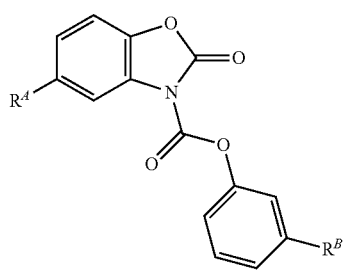
(II-C14)
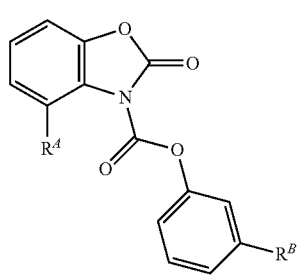
(II-C15)
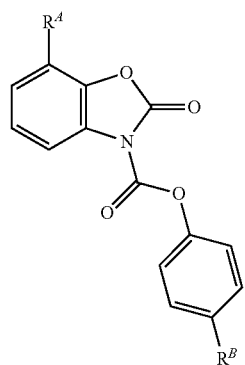
(II-C16)

-continued
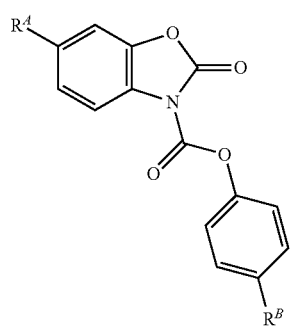 (II-C17)
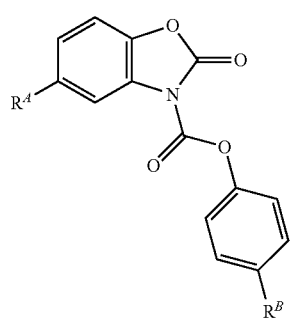 (II-C18)
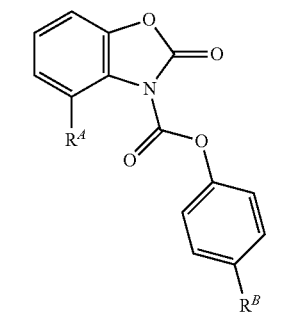 (II-C19)
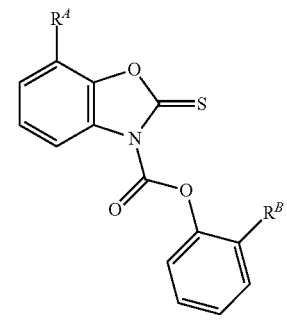 (III-C8)
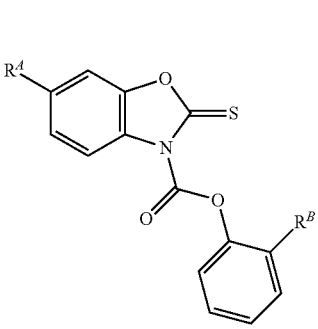 (III-C9)
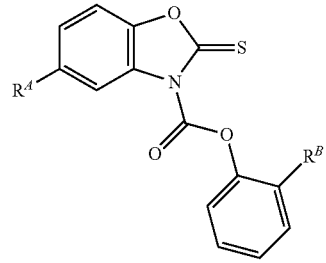 (III-C10)
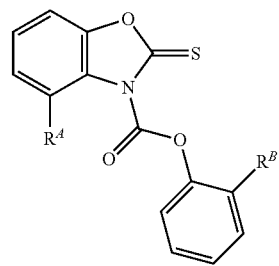 (III-C11)
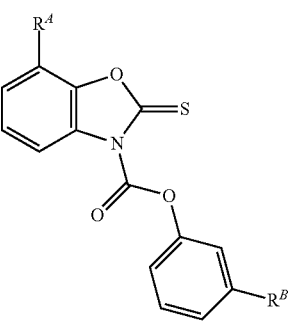 (III-C12)
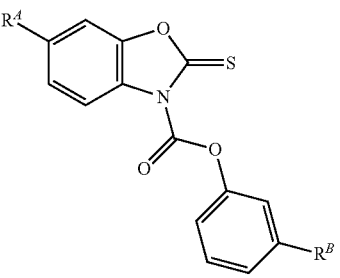 (III-C13)
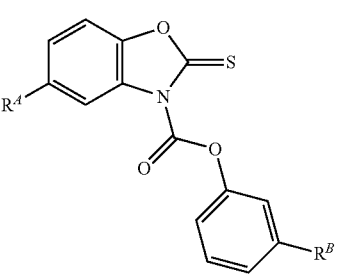 (III-C14)

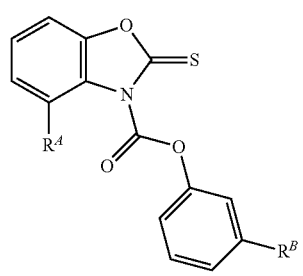
(III-C15)
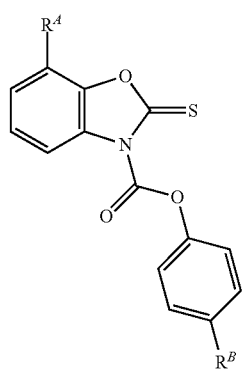
(III-C16)
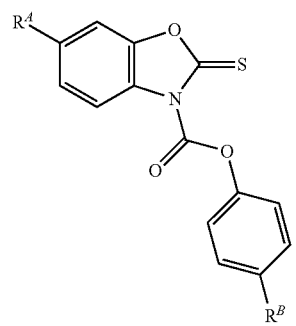
(III-C17)
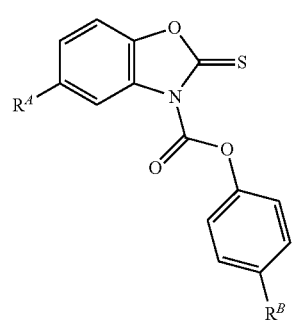
(III-C18)
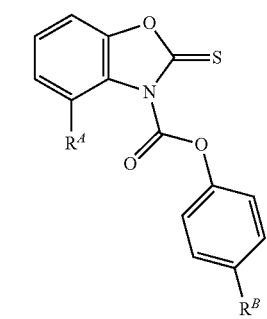
(III-C19)
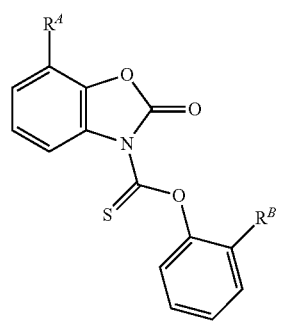
(IV-C8)
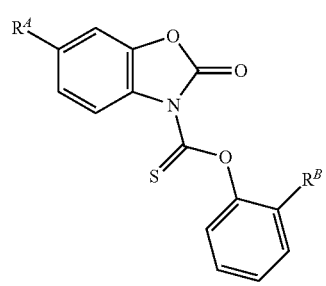
(IV-C9)
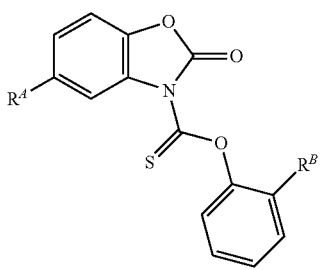
(IV-C10)
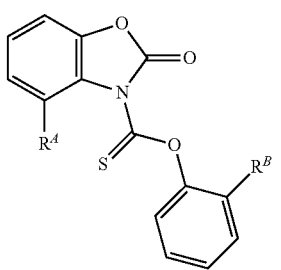
(IV-C11)
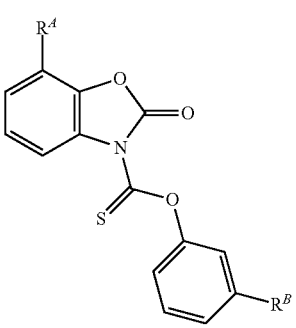
(IV-C12)

-continued
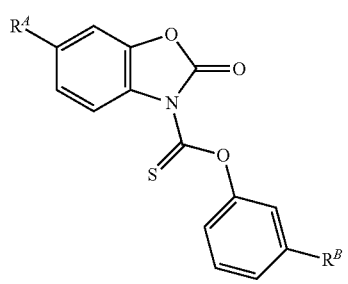 (IV-C13)
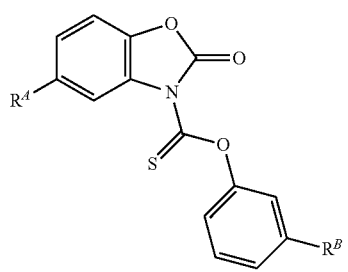 (IV-C14)
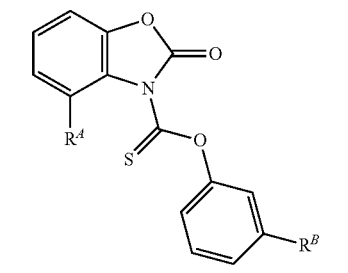 (IV-C15)
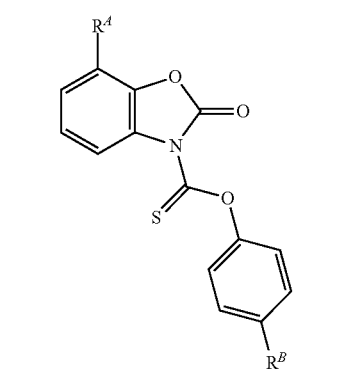 (IV-C16)
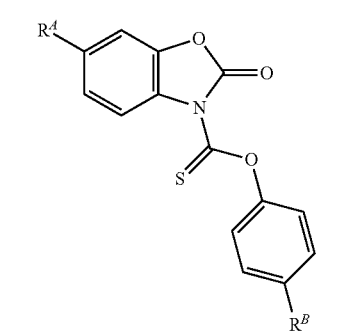 (IV-C17)
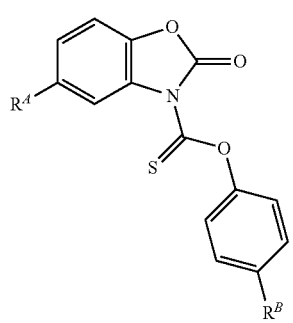 (IV-C18)
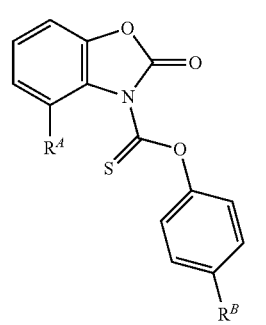 (IV-C19)
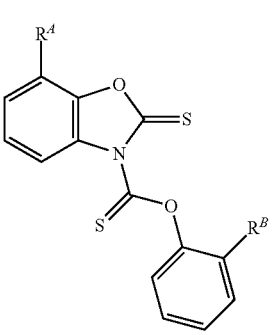 (V-C8)
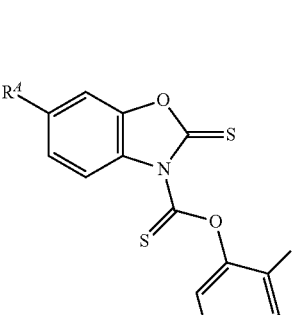 (V-C9)
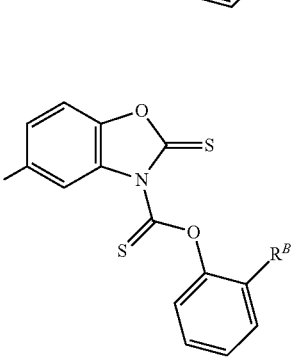 (V-C10)

(V-C11)
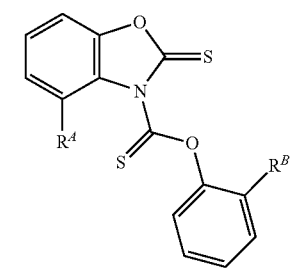

(V-C12)
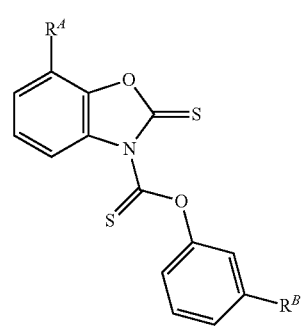

(V-C13)
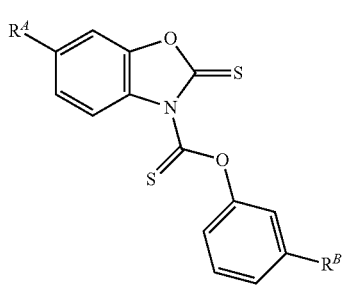

(V-C14)
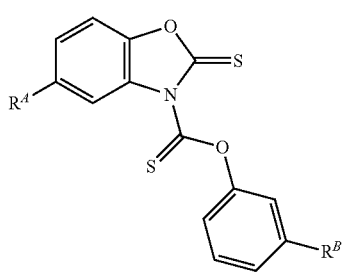

(V-C15)
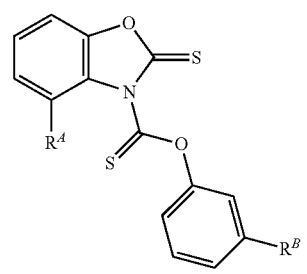

(V-C16)
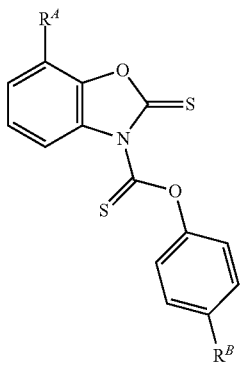

(V-C17)
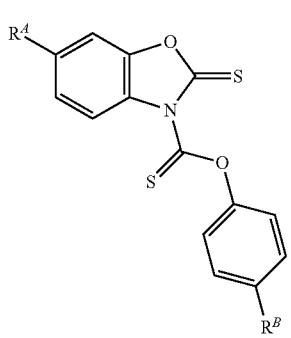

(V-C18)
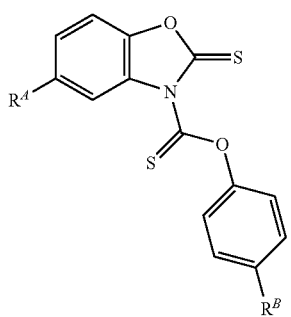

(V-C19)
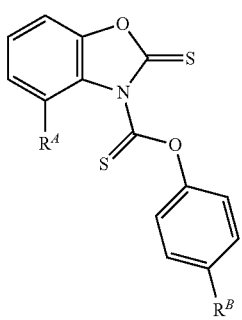

or a pharmaceutically acceptable salt thereof; wherein $R^A$ and $R^B$ are as defined herein. In certain embodiments, $R^B$ is an electron-donating group, as defined herein. In certain embodiments, $R^B$ is selected from the group consisting of —$OR^{B1}$, —$N(R^{B2})_2$, and —$SR^{B1}$. In certain embodiments, $R^B$ is —$OR^{B1}$. In certain embodiments, $R^A$ is an electron-withdrawing group, as defined herein. In certain embodiments, $R^A$ is —C(=O)$R^{A1}$.

In certain embodiments, a provided compound has one of the following formulae:

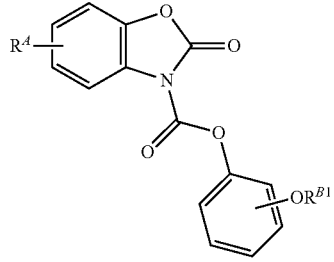
(II-C20)

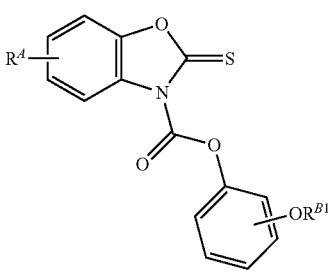
(III-C20)

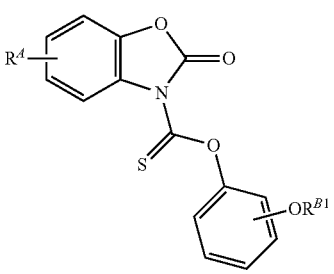
(IV-C20)

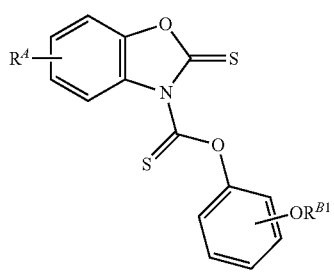
(V-C20)

or a pharmaceutically acceptable salt thereof; wherein $R^A$ and $R^{B1}$ are as defined herein. In certain embodiments, $R^A$ is an electron-withdrawing group, as defined herein. In certain embodiments, $R^A$ is —C(=O)$R^{A1}$.

In certain embodiments, a provided compound has one of the following formulae:

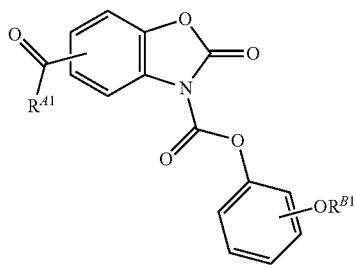
(II-C21)

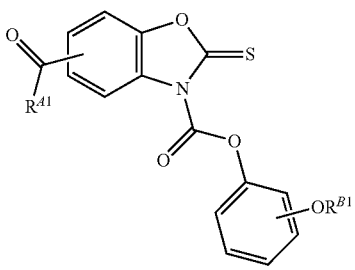
(III-C21)

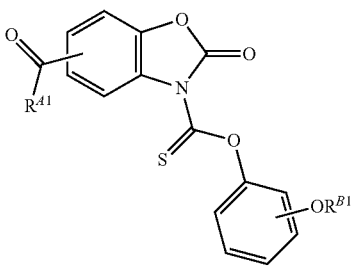
(IV-C21)

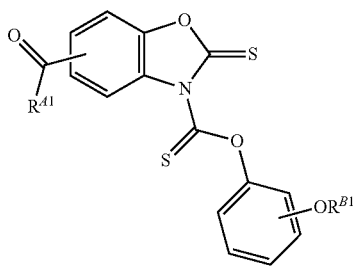
(V-C21)

or a pharmaceutically acceptable salt thereof; wherein $R^{A1}$ and $R^B$ are as defined herein.

In certain embodiments, a provided compound has one of the following formulae:

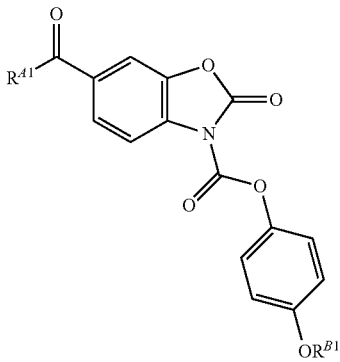
(II-C22)

-continued
(III-C22)
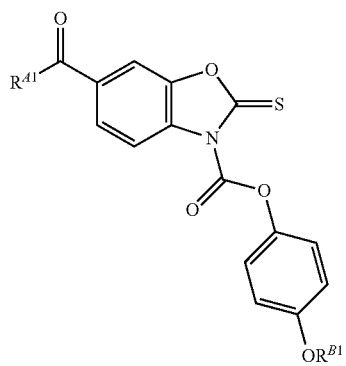
(IV-C22)
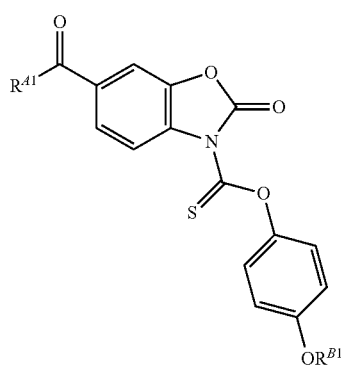
(V-C22)
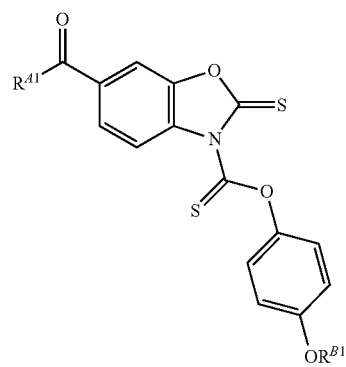
or a pharmaceutically acceptable salt thereof; wherein $R^{41}$ and $R^{B1}$ are as defined herein.
In certain embodiments, a provided compound is of the formula:
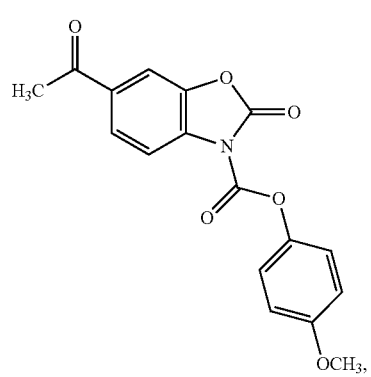
-continued
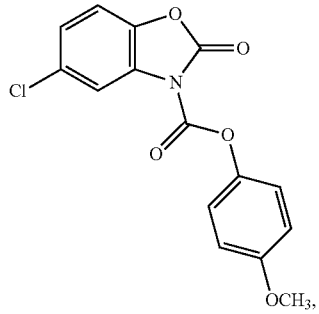
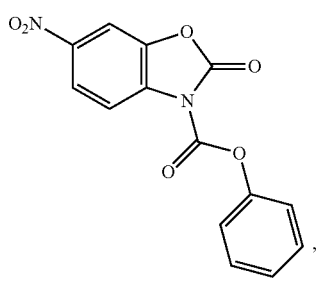
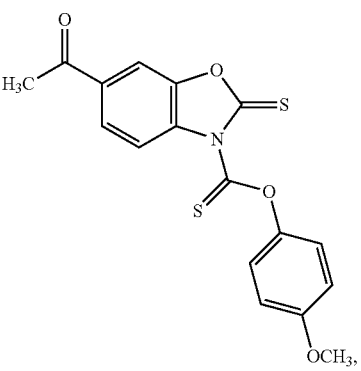
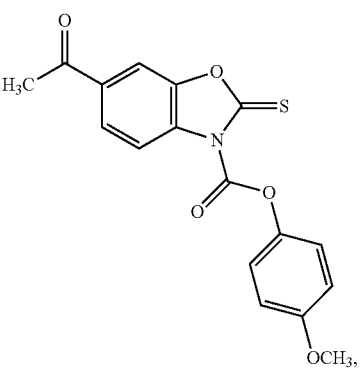
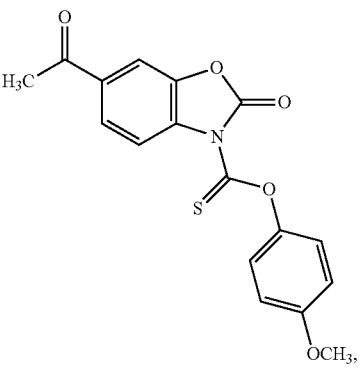

79
-continued
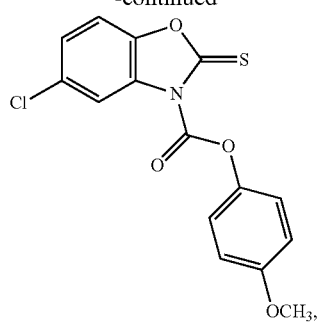
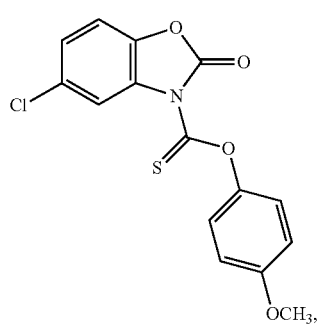
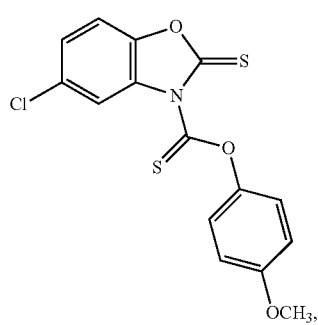
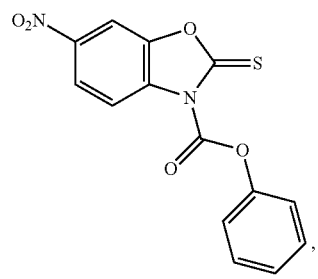
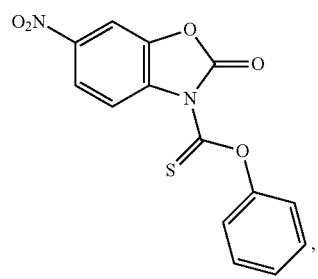
80
-continued
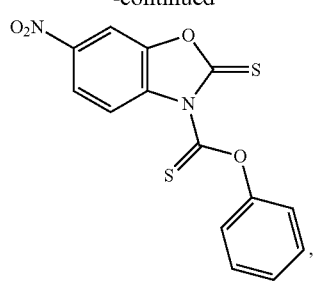
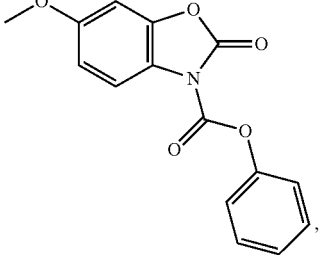
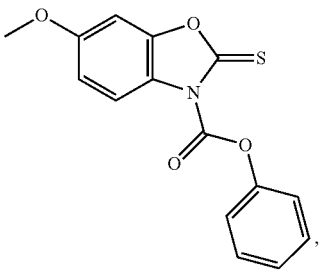
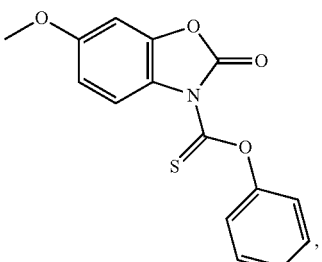
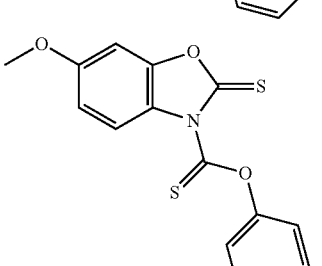
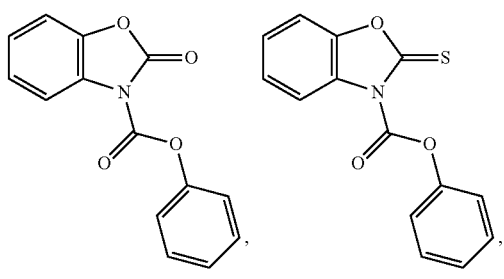

81
-continued

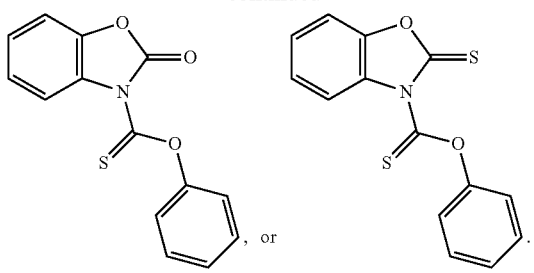
, or

In certain embodiments, a provided compound is of the formula:

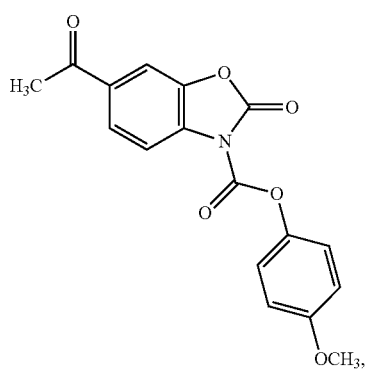

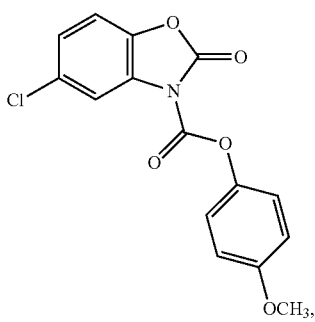

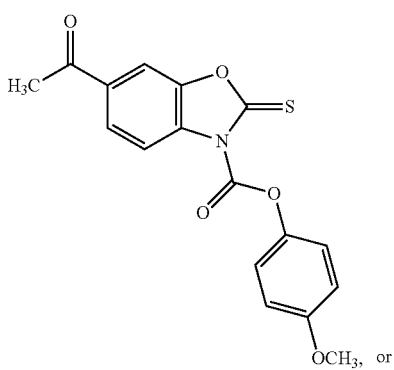
, or

82
-continued

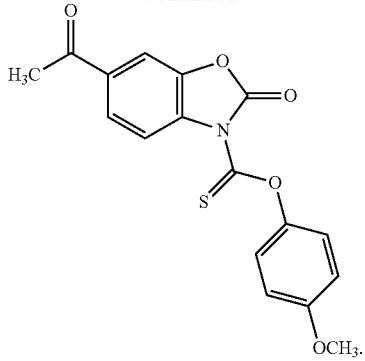

Pharmaceutical Compositions and Administration

The present invention provides pharmaceutical compositions comprising a compound of the present invention, e.g., a compound of Formula (I), or a pharmaceutically acceptable salt thereof, as described herein, and optionally a pharmaceutically acceptable excipient. In certain embodiments, the compound of the present invention, or a pharmaceutically acceptable salt thereof, is provided in an effective amount in the pharmaceutical composition. In certain embodiments, the effective amount is a therapeutically effective amount. In certain embodiments, the effective amount is a prophylactically effective amount.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, anti-cancer agents, anti-diabetic agents, anti-inflammatory agents, immunosuppressant agents, and a pain-relieving agent. Therapeutically active agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

In certain embodiments, the additional therapeutic agent is an anti-cancer agent. Anti-cancer agents encompass biotherapeutic anti-cancer agents, chemotherapeutic agents, and anti-cancer therapy such as radiation. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1,2,4,6, or 12), immune cell growth factors (e.g., GM-CSF) and antibodies (e.g., HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g., tamoxifen, raloxifene, and megestrol), LHRH agonists (e.g., goscrclin and leuprolide), anti-androgens (e.g., flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g. dacarbazine, temozolomide), platinum containing compounds (e.g., cisplatin, carboplatin, oxaliplatin), vinca alkaloids (e.g., vincristine, vinblastine, vindesine, and vinorelbine), taxoids (e.g., paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), antimetabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g. lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g. bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, caminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, caminomycin, aminopterin, and hexamethyl melamine.

In certain embodiments, the additional therapeutically active agent is a pain-relieving agent. Exemplary pain relieving agents include, but are not limited to, analgesics such as non-narcotic analgesics (e.g., salicylates such as aspirin, ibuprofen (MOTRIN®, ADVIL®), ketoprofen (ORUDIS®), naproxen (NAPROSYN®), acetaminophen, indomethacin) or narcotic analgesics (e.g., opioid analgesics such as tramadol, fentenyl, sufentanil, morphine, hydromorphone, codeine, oxycodone, and buprenorphine); non-steroidal anti-inflammatory agents (NSAIDs) [e.g., aspirin, acetaminophen, COX-2 inhibitors]; steroids or anti-rheumatic agents; migraine preparations such as beta adrenergic blocking agents, ergot derivatives; tricyclic antidepressants (e.g., amitryptyline, desipramine, imipramine); anti-epileptics (e.g., clonaxepam, valproic acid, phenobarbital, phenyloin, tiagaine, gabapentin, carbamazepine, topiramate, sodium valproate); $α_2$ agonists; selective serotonin reuptake inhibitors (SSRIs), selective norepinepherine uptake inhibitors; benzodiazepines; mexiletine (MEXITIL); flecamide (TAMBOCOR); NMDA receptor antagonists [e.g., ketamine, detromethorphan, methadone]; and topical agents (e.g., capsaicin (Zostrix), EMLA cream, lidocaine, prilocalne).

In other embodiments, the additional therapeutically active agent is an anti-inflammatory agent. Exemplary anti-inflammatory agents include, but are not limited to, aspirin; ibuprofen; ketoprofen; naproxen; etodolac (LODINE®); COX-2 inhibitors such as celecoxib (CELEBREX®), rofecoxib (VIOXX®), valdecoxib (BEXTRA®), parecoxib, etoricoxib (MK663), deracoxib, 2-(4-ethoxy-phenyl)-3-(4-methanesulfonyl-phenyl)-pyrazolo[1,5-b]pyridazine, 4-(2-oxo-3-phenyl-2,3-dihydrooxazol-4-yl)benzenesulfonamide, darbufelone, flosulide, 4-(4-cyclohexyl-2-methyl-5-oxazolyl)-2-fluorobenzenesulfonamide), meloxicam, nimesulide, 1-Methylsulfonyl-4-(1,1-dimethyl-4-(4-fluorophenyl)cyclopenta-2,4-dien-3-yl)benzene, 4-(1,5-Dihydro-6-fluoro- 7-methoxy-3-(trifluoromethyl)-(2)-benzothiopyrano(4,3-c) pyrazol-1-yl)benzenesulfonamide, 4,4-dimethyl-2-phenyl-3-(4-methylsulfonyl)phenyl)cyclo-butenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzo-furanyl)-4-cyclopropyl butan-1-one, or their physiologically acceptable salts, esters or solvates; sulindac (CLINORIL®); diclofenac (VOLTAREN®); piroxicam (FELDENE®); diflunisal (DOLOBID®), nabumetone (RELAFEN®), oxaprozin (DAYPRO®), indomethacin (INDOCIN®); or steroids such as PEDIAPED® prednisolone sodium phosphate oral solution, SOLU-MEDROL® methylprednisolone sodium succinate for injection, PRELONE® brand prednisolone syrup. Further examples of anti-inflammatory agents include naproxen, which is commercially available in the form of EC-NAPROSYN® delayed release tablets, NAPROSYN®, ANAPROX® and ANAPROX® DS tablets and NAPROSYN® suspension from Roche Labs, CELEBREX® brand of celecoxib tablets, VIOXX® brand of rofecoxib, CELESTONE® brand of betamethasone, CUPRAMINE® brand penicillamine capsules, DEPEN® brand titratable penicillamine tablets, DEPO-MEDROL brand of methylprednisolone acetate injectable suspension, ARAVA™ leflunomide tablets, AZULFIDIINE EN-tabs® brand of sulfasalazine delayed release tablets, FELDENE® brand piroxicam capsules, CATAFLAM® diclofenac potassium tablets, VOLTAREN® diclofenac sodium delayed release tablets, VOLTAREN®-XR diclofenac sodium extended release tablets, or ENBREL® etanerecept products.

In other embodiments, the additional therapeutically active agent is an anti-diabetic agent. Exemplary anti-diabetic agents include, but are not limited to, glyburide, glipizide, glimepiride, metformin, sitagliptin, pioglitazone, rosiglitazone, repaglinide, nateglinide, acarbose, miglitol, MICRONASE®, DIABETA®, MICRONASE®, GLYNASE®, GLUCOTROL®, AMARYL®, GLUCOPHAGE®, JANUVIA®, ACTOS®, AVANDIA®, PRANDIN®, STARLIX®, PRECOSE®, GLYSET®, METAGLIP®, GLUCOVANCE®, ACTOPLUS MET®, AVANDARYL®, AVANDAMET®, and JANUMET®.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Methods of Use and Treatment

Compounds and compositions described herein are generally useful for the inhibition of the activity of glycosyltransferases, e.g., O-GlcNAc transferase (OGT) or a mutant or variant thereof. OGT has been implicated in a variety of conditions, including but not limited to, diabetes and complications thereof, proliferative diseases (e.g., cancers, benign neoplasms, diabetic retinopathy, and smooth muscle cell proliferation (e.g., vascular proliferative disorders, atherosclerosis, and restenosis)), neurodegenerative diseases, autoimmune diseases, and inflammatory diseases. See, e.g., Golks et al., *EMBO Reports* (2008) 9:748-753; Liu et al., *Proc. Natl. Acad. Sci. USA* (2004) 101: 10804-10809; Jones, *Circulation Research* (2005) 96: 925-926; Golks et al., *EMBO J.* (2007) 26: 4369-4379; Ohn et al., *Nature Cell Biol*. (2008) 10: 1224-1231. Thus, in one aspect, provided is a method of treating an O-linked N-acetylglucosamine (O-GlcNAc) transferase (OGT)-associated condition, the method comprising administering an effective amount of a compound of the present invention, or a pharmaceutically acceptable salt thereof, to a subject in need thereof. In certain embodiments, the effective amount is a therapeutically effective amount. In certain embodiments, the effective amount is a prophylactically effective amount.

Compounds and compositions described herein are also generally useful for the inhibition of kinases or mutants or variants thereof. Kinases been implicated in a variety of conditions, including but not limited to, proliferative diseases, smooth muscle cell proliferation (e.g., vascular proliferative disorders, atherosclerosis, and restenosis), neurodegenerative diseases, autoimmune diseases, and inflammatory diseases. Thus, in one aspect, provided is a method of treating a kinase-associated condition, the method comprising administering an effective amount of a compound of the present invention, or a pharmaceutically acceptable salt thereof, to a subject in need thereof.

In certain embodiments, the condition being treated with a compound of the invention is diabetes (e.g., diabetes mellitus Type 1, diabetes mellitus Type 2). In certain embodiments, provided is a method of treating diabetes in a subject at risk of having diabetes or a diabetic subject, the method comprising administering an effective amount of a compound of the present invention, or a pharmaceutical salt thereof. In certain embodiments, the effective amount is a therapeutically effective amount. In certain embodiments, the effective amount is a prophylactically effective amount. In certain embodiments, the diabetes is Type I diabetes. In certain embodiments, the diabetes is Type II diabetes. As used herein, a subject who is "at risk of having diabetes" encompasses subjects who have a predisposition (e.g., genetic or otherwise) to develop Type I diabetes, and subjects who exhibit warning signs for Type II diabetes, e.g., diagnosed with "pre-diabetes" or "impaired glucose tolerance" wherein the subject has blood glucose levels higher than normal but not yet high enough to be diagnosed as diabetic. In certain embodiments, the method further comprises treatment of a complication of diabetes in a subject at risk of having diabetes or a diabetic subject, e.g., treatment of insulin resistance, vascular disease, skin ulcers, circulatory damage, cardiac dysfunction, diabetic nephropathy, diabetic retinopathy, microvascular disease, macrovascular disease, and/or diabetic neuropathy.

In certain embodiments, the condition being treated is a proliferative disease, e.g., cancer. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma);

esophageal cancer (e.g., adenocarcinoma of the esophagus, Barrett's adenocarinoma); Ewing sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer [e.g., squamous cell carcinoma (SCC), keratoacanthoma (KA), melanoma, basal cell carcinoma (BCC)]; small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

In certain embodiments, the condition is a neurodegenerative disease. Exemplary neurodegenerative diseases include, but are not limited to, Alzheimer's disease, Huntington's disease, progressive supranuclear palsy, corticobasal degeneration, frontotemporal lobar degeneration, Pick's disease, Parkinson's disease, Lewy body disease, and amyotropic lateral sclerosis (ALS).

In certain embodiments, the condition being treated is an autoimmune disease. Exemplary autoimmune diseases include, but are not limited to, rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic arthritis, juvenile arthritis, asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), Still's disease, myasthenia gravis, Hashimoto's thyroiditis, Ord's thyroiditis, Grave's disease, acute disseminated encephalomyelitis, Addison's disease, opsoclonus-myoclonus syndrome, antiphospholipid antibody syndrome, autoimmune hepatitis, celiac disease, Goodpasture's syndrome, optic neuritis, scleroderma, primary biliary cirrhosis, Reiter's syndrome, warm autoimmune hemolytic anemia, alopecia universalis, chronic fatigue, dysautonomia, neuromyotonia, vulvodynia and disorders ameliorated by a gastroprokinetic agent (e.g., ileus, postoperative ileus and ileus during sepsis; gastroesophageal reflux disease (GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In certain embodiments, the condition being treated is an inflammatory disease. The term "inflammatory disease" refers to those conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory diseases include, but are not limited to inflammation associated with acne, asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis, and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, dry eye syndrome, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis), inflammatory bowel syndrome (IBS), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis, prostatistis, appendicitis, Blau syndrome, blepharitis, bronchiolitis, cervicitis, cholangitis, cholecystitis, chronic recurrent multifocal osteomyelitis (CRMO), cryopyrin associated periodic syndrome (CAPS), dacryoadenitis, dermatomyositis, dry eye syndrome, encephalitis, endocarditis, endometritis, enterocolitis, epicondylitis, epididymitis, familial cold-induced autoinflammatory syndrome, familial Mediterranean fever (FMF), fasciitis, fibrositis, hepatitis, hidradenitis suppurativa, laryngitis, mastitis, meningitis, mevalonate kinase deficiency (MKD), Muckle-Well syndrome, myelitis myocarditis, myositis, nephritis, oophoritis, orchitis, osteitis, inflammatory osteolysis, otitis, pancreatitis, parotitis, pericarditis, peritonitis, pharyngitis, pleuritis, phlebitis, pneumonitis, pneumonia, proctitis, pulmonary fibrosis, pyelonephritis, pyoderma gangrenosum and acne syndrome (PAPA), pyogenic sterile arthritis, rhinitis, salpingitis, sinusitis, stomatitis, synovitis, TNF receptor associated periodic syndrome (TRAPS), tonsillitis, undifferentiated arthropathy, uveitis, vaginitis and vulvitis. In certain embodiments, the inflammatory condition is an acute inflammatory condition (e.g., inflammation resulting from infection). In certain embodiments, the inflammatory condition is a chronic inflammatory condition (e.g., conditions resulting from asthma, arthritis and inflammatory bowel disease). The compounds may also be useful in treating inflammation associated with trauma and non-inflammatory myalgia. The compounds may also be useful in treating inflammation associated with cancer.

In certain embodiments, the present invention provides methods for treating or lessening the severity of arthropathies and osteopathological diseases including, but not limited to, rheumatoid arthritis, osteoarthrtis, gout, polyarthritis, and psoriatic arthritis.

In certain embodiments, the present invention provides methods for treating or lessening the severity of acute and chronic inflammatory diseases including, but not limited to, ulcerative colitis, inflammatory bowel disease, Crohn's disease, dry eye syndrome, allergic rhinitis, allergic dermatitis, cystic fibrosis, chronic obstructive bronchitis, and asthma.

In certain embodiments, the invention provides methods for treating or lessening the severity of hyperproliferative diseases including, but not limited to, psoriasis or smooth muscle cell proliferation including vascular proliferative disorders, atherosclerosis, and restenosis.

In certain embodiments, the invention provides methods for treating or lessening the severity of endometriosis, uterine fibroids, endometrial hyperplasia, and benign prostate hyperplasia.

In some embodiments, the invention provides a method for treating or lessening the severity of one or more diseases and conditions, wherein the disease or condition is selected from immune-related conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, the invention provides methods for treating tumorogenesis.

The Polo-like kinases (PLK) belong to a family of serine/threonine kinases that are highly conserved across the species, ranging from yeast to man (reviewed in Lowery et al., *Oncogene* 2005, 24:248-259). The PLK kinases have multiple roles in cell cycle, including control of entry into and progression through mitosis.

PLK1 is the best characterized of the PLK family members. PLK1 is widely expressed and is most abundant in tissues with a high mitotic index. Protein levels of PLK1 rise and peak in mitosis (Hamanaka, et al., *J Biol Chem* 1995, 270:21086-21091). The reported substrates of PLK1 are all molecules that are known to regulate entry and progression through mitosis, and include CDC25C, cyclin B, p53, APC, BRCA2 and the proteasome. PLK1 is upregulated in multiple cancer types and the expression levels correlate with severity of disease (Macmillan, et al., *Ann Surg Oncol* 2001, 8:729-740). PLK1 is an oncogene and can transform NIH-3T3 cells (Smith, et al., *Biochem Biophys Res Commun* 1997, 234:397-405). Depletion or inhibition of PLK1 by siRNA, antisense, microinjection of antibodies, or transfection of a dominant negative construct of PLK1 into cells, reduces proliferation and viability of tumor cells in vitro (Guan, et al., *Cancer Res* 2005, 65:2698-2704; Liu, et al., *Proc Natl Acad Sci USA* 2003, 100:5789-5794; Fan, et al., *World J Gastroenterol* 2005, 11:4596-4599; Lane, et al., *J Cell Biol* 1996, 135:1701-1713). Tumor cells that have been depleted of PLK1 have activated spindle checkpoints and defects in spindle formation, chromosome alignment and separation and cytokinesis. Loss in viability has been reported to be the result of an induction of apoptosis. In contrast, normal cells have been reported to maintain viability on depletion of PLK1. In vivo knock down of PLK1 by siRNA or the use of dominant negative constructs leads to growth inhibition or regression of tumors in xenograft models.

PLK2 is mainly expressed during the G1 phase of the cell cycle and is localized to the centrosome in interphase cells. PLK2 knockout mice develop normally, are fertile and have normal survival rates, but are around 20% smaller than wild type mice. Cells from knockout animals progress through the cell cycle more slowly than in normal mice (Ma, et al., *Mol Cell Biol* 2003, 23:6936-6943). Depletion of PLK2 by siRNA or transfection of kinase inactive mutants into cells blocks centriole duplication. Downregulation of PLK2 also sensitizes tumor cells to taxol and promotes mitotic catastrophe, in part by suppression of the p53 response (Burns et al., *Mol Cell Biol* 2003, 23:5556-5571).

PLK3 is expressed throughout the cell cycle and increases from G1 to mitosis. Expression is upregulated in highly proliferating ovarian tumors and breast cancer and is associated with a worse prognosis (Weichert, et al., *Br J Cancer* 2004, 90:815-821; Weichert, et al., *Virchows Arch* 2005, 446:442-450). In addition to regulation of mitosis, PLK3 is believed to be involved in Golgi fragmentation during the cell cycle and in the DNA-damage response. Inhibition of PLK3 by dominant negative expression is reported to promote p53-independent apoptosis after DNA damage and suppresses colony formation by tumor cells (Li, et al., *J Biol Chem* 2005, 280:16843-16850).

PLK4 is structurally more diverse from the other PLK family members. Depletion of this kinase causes apoptosis in cancer cells (Li, et al., *Neoplasia* 2005, 7:312-323). PLK4 knockout mice arrest at E7.5 with a high fraction of cells in mitosis and partly segregated chromosomes (Hudson, et al., *Current Biology* 2001, 11:441-446).

In some embodiments, compounds of the present invention inhibit PLK. Thus, in certain embodiments, the present invention provides a method of treated a PLK-associated condition (e.g., a PLK1-, PLK2-, PLK3-, and/or PLK4-associated condition), the method comprising administering an effective amount of a compound of the present invention, or a pharmaceutically acceptable salt thereof, to a subject in need thereof. In certain embodiments, compounds of the present invention inhibit PLK1. Thus, in certain embodiments, the present invention provides a method of treating a PLK1-associated condition, the method comprising administering an effective amount of a compound of the present invention, or a pharmaceutically acceptable salt thereof, to a subject in need thereof. In certain embodiments, a PLK1-associated condition is a proliferative disorder (e.g., cancer). In certain embodiments, compounds of the present invention are used to treat solid tumors arising from various tissue types, including, but not limited to, cancers of the bone, breast, respiratory tract, brain reproductive organs, digestive tract, urinary tract (e.g., bladder), eye, liver, skin, head, neck, thyroid, parathyroid, and metastatic forms thereof.

The serine/threonine kinase family also includes the mitogen-activated protein (MAP) kinases. Mitogen Activated Protein Kinases (MAPKs) are members of signal transduction pathways that change cell physiology in response to external stimuli by activating a variety of downstream signaling genes products. These gene products control diverse cellular functions such as the production of proinflammatory cytokines involved in establishing and maintaining specific human diseases. The MAPKs are activated by phosphorylation on specific residues within the activation loop sequence by specific upstream MAPK kinases (MKKs) in response to a cellular activation signal. In turn, the MAPKs activate a variety of downstream gene products. There are four major classes of MAPKs: 1) the archetypal extracellular regulated kinases (ERKs), 2) the c-jun N-terminal kinases (JNKs), 3) the p38 MAPKs and finally, 4) the ERK5 or BigMAPKs. The MAPK pathways are involved in alterations in cell physiology resulting from cell stimulation. They control various cell processes such as: cell death, cell cycle machinery, gene transcription and protein translation.

Kinases of the p38 MAPK family (also known as p38, SAPK2a, RK, MPK2, Mxi2 and CSBP), most notably the p38alpha and p38beta isoforms, can activate a wide variety of regulatory proteins. In this manner, p38 can diversify downstream signaling leading to a wide variety of cellular outcomes. Central to the signal transduction process initiated by p38 activation is MAPKAPK2. Most of the physiological outcomes of MAPKAPK2 have been established using mice genetically deficient in MAPKAPK2. A significant phenotype of the MAPKAPK2-deficient mice is that proinflammatory cytokine production is inhibited following stimulation of splenocytes with lipopolysaccharide (LPS). Specifically, the production of tumor necrosis factor-α (TNF-α), interleukin-1β (IL-1β), IL-6, and interferon-γ (IFN-γ) is blocked. This phenotype cannot be rescued by the expression of a kinase dead MAPKAPK2 mutant, indicating that the kinase function of MAPKAPK2 is required for proinflammatory cytokine production. Thus, an inhibitor of MAPKAPK2 kinase activity has the potential to exhibit the same inhibitory effects on the production of proinflammatory cytokines.

MAPKAPK2 activates a number of substrates, including the mRNA binding protein, tristetraproline (TTP). TTP expression is induced by proinflammatory stimuli such as lipopolysaccharide (LPS) or tumor necrosis factor-α (TNF-α). TTP binds to the AU-rich element within the 3'-untranslated region of the TNF-α transcript resulting in a decrease in TNF-α mRNA stability. TTP1-deficient mice exhibit many defects including arthritis and systemic lupus erythematosis-like symptoms presumably resulting from an increase in circulating TNF-α levels.

Elevated levels of proinflammatory cytokines are associated with a number of diseases such as toxic shock syndrome, rheumatoid arthritis, osteoarthritis, diabetes and inflammatory bowel disease. In these diseases, chronic elevation of inflammation exacerbates or causes much of the pathophysiology observed. For example, rheumatoid synovial tissue becomes invaded with inflammatory cells that result in destruction to cartilage and bone. Studies suggest that inflammatory changes mediated by cytokines may be involved in endothelial cell pathogenesis including restenosis after percutaneous transluminal coronary angioplasty (PTCA). An important and accepted therapeutic approach for potential drug intervention in these diseases is the reduction of pro-inflammatory cytokines such as TNF-α and IL-1β. Several biological agents directed against these proinflammatory cytokines (anti-TNF antibodies, a soluble TNF receptor and an IL-1 receptor antagonist) have been FDA approved for the treatment of rheumatoid arthritis, Crohn's disease and psoriatic arthritis.

Proinflammatory cytokines such as TNF-α and IL-6 are also important mediators of septic shock and associated cardiopulmonary dysfunction, acute respiratory distress syndrome (ARDS) and multiple organ failure. In a study of patients presenting with sepsis, a correlation was found between TNF-α and IL-6 levels and septic complications. TNF-α has also been implicated in cachexia and muscle degradation associated with HIV infection. Obesity is associated with an increase incidence of infection, diabetes and cardiovascular disease. Abnormalities in TNF-α expression have been noted for each of the above conditions. It has been proposed that elevated levels of TNF-alpha are involved in other eating related disorders such as anorexia and bulimia nervosa. Pathophysiological parallels are drawn between anorexia nervosa and cancer cachexia. An inhibitor of TNF-α production, HU-211, has been shown to improve the outcome of closed brain injury in an experimental model. Atherosclerosis is known to have an inflammatory component and cytokines such as IL-I and TNF have been suggested to promote the disease. In an animal model an IL-I receptor antagonist was shown to inhibit fatty streak formation.

TNF-α levels are elevated in airways of patients with chronic obstructive pulmonary disease and it may contribute to the pathogenesis of this disease. Circulating TNF-α may also contribute to weight loss associated with this disease. Elevated TNF-α levels have also been found to be associated with congestive heart failure and the level has been correlated with severity of the disease. In addition, TNF-α has been implicated in reperfusion injury in lung, kidney, and the nervous system. TNF-α is also a potent osteoclastogenic agent and is involved in bone resorption and diseases involving bone resorption. It has also been found highly expressed in chondrocytes of patients with traumatic arthritis. TNF-α has also been shown to play a key role in the development of glomerulonephritis.

The proinflammatory cytokine IL-6 has been implicated with the acute phase response. IL-6 is a growth factor in a number in oncological diseases including multiple myeloma and related plasma cell dyscrasias. It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis. IL-6 also plays a significant role in osteoporosis. In murine models it has been shown to effect bone resorption and to induce osteoclast activity. Marked cytokine differences, such as IL-6 levels, exist in vivo between osteoclasts of normal bone and bone from patients with Paget's disease. A number of cytokines have been shown to be involved in cancer cachexia. The severity of key parameters of cachexia can be reduced by treatment with anti IL-6 antibodies or with IL-6 receptor antagonists. Several infectious diseases, such as influenza, indicate IL-6 and IFN alpha as key factors in both symptom formation and in host defense. Overexpression of IL-6 has been implicated in the pathology of a number of diseases including multiple myeloma, rheumatoid arthritis, Castleman's disease, psoriasis, post-menopausal osteoporosis and juvenile idiopathic arthritis. Compounds that interfered with the production of cytokines including IL-6, and TNF were effective in blocking a passive cutaneous anaphylaxis in mice. More recently, a humanized antibody directed against the IL-6 receptor, demonstrated efficacy in a randomized double-blind pilot human clinical study by significantly reducing the Crohn's disease activity index.

IFN-γ has been implicated in a number of diseases. It has been associated with increased collagen deposition that is a central histopathological feature of graft-versus-host disease. Following kidney transplantation, a patient was diagnosed with acute myelogenous leukemia. Retrospective analysis of peripheral blood cytokines revealed elevated levels of GM-CSF and IFN-γ. These elevated levels coincided with a rise in peripheral blood white cell count. The development of insulin-dependent diabetes (Type 1) can be correlated with the accumulation in pancreatic islet cells of T-cells producing IFN-γ. IFN-γ along with TNF, IL-2 and IL-6 lead to the activation of most peripheral T-cells prior to the development of lesions in the central nervous system for diseases such as multiple sclerosis (MS) and AIDS dementia complex. Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-I and IFN-gamma. These cytokines are thought to be involved in promoting apoptosis or programmed cell death of the surrounding vascular smooth muscle cells resulting in the atherosclerotic lesions. Allergic subjects produce mRNA specific for IFN-gamma following challenge with Vespula venom. The expression of a number of cytokines, including IFN-gamma has been shown to increase following a delayed type hypersensitivity reaction thus indicating a role for IFN-gamma in atopic dermatitis. Histopathologic and immunohistologic studies were performed in cases of fatal cerebral malaria. Evidence for elevated IFN-gamma amongst other cytokines was observed indicating a role in this disease. The importance of free radical species in the pathogenesis of various infectious diseases has been established. The nitric oxide synthesis pathway is activated in response to infection with certain viruses via the induction of proinflammatory cytokines such as IFN-gamma. Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN-gamma, TNF and IL-2. IFN-gamma can selectively inhibit cytokine induced bone resorption. It appears to do this via the intermediacy of nitric oxide (NO) which is an important regulatory molecule in bone remodeling. NO may be involved as a mediator of bone disease for such diseases as: rheumatoid arthritis, tumor associated osteolysis and postmenopausal osteoporosis. Studies with gene deficient mice have demonstrated that the IL-12 dependent production of IFN-gamma is critical in the control of early parasitic growth. Although this process is independent of nitric oxide the control of chronic infection does appear to be NO dependent. NO is an important vasodilator and convincing evidence exists for its role in cardiovascular shock. IFN-gamma is required for progression of chronic intestinal inflammation in such diseases as Crohn's disease and inflammatory bowel disease (IBD) presumably through the intermediacy of CD4+ lymphocytes probably of the THl phenotype. An elevated level of serum IgE is associated with various atopic diseases such as bronchial asthma and atopic dermatitis. The level of IFN-γ was negatively correlated with serum IgE suggesting a role for IFN-γ in atopic patients.

The proinflammatory cytokine, IL-1β, is partially controlled by MAPKAPK2. Hence, inhibition of MAPKAPK2 may impact IL-1β dependent processes. IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis. In a phase III human clinical trial IL-1ra reduced the mortality rate in patients with septic shock syndrome. Several other diseases affected by IL-1 include adult onset Still's disease, macrophage auto-activation syndromes, Muckle-Wells syndrome, familial cold autoinflammatory syndrome, and neonatal onset multisystem inflammatory disease. Patients with Muckle-Wells syndrome exhibiting systemic inflammation were treated with anakinra (IL-1ra), leukocytosis serum amyloid A, C-reactive protein, and local inflammatory arthritis were reduced with a few days demonstrating that systemic inflammation is IL-1 mediated. Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis. Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage. The promotion of beta-cell destruction leading to insulin dependent diabetes mellitus shows dependence on IL-I. Some of this damage may be mediated through other effectors such as prostaglandins and thromboxanes. IL-I can effect this process by controlling the level of both cyclooxygenase II and inducible nitric oxide synthetase expression.

Inhibitors of cytokine production are expected to block inducible cyclooxygenase (COX-2) expression. COX-2 expression has been shown to be increased by cytokines and it is believed to be the isoform of cyclooxygenase responsible for inflammation. Accordingly, inhibitors of MAPKAPK2 reducing the production of cytokines such as IL-1, would be expected to exhibit efficacy against those disorders currently treated with COX inhibitors such as the familiar NSAIDs. These disorders include acute and chronic pain as well as symptoms of inflammation and cardiovascular disease.

Elevation of several cytokines has been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD.

Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1. A role for IL-1 in the pathogenesis of human immunodeficiency virus (HIV) has been identified. IL-1ra showed a clear relationship to acute inflammatory events as well as to the different disease stages in the pathophysiology of HIV infection. IL-1 and TNF are both involved in periodontal disease. The destructive process associated with periodontal disease may be due to a disregulation of both IL-1 and TNF.

IL-1 has also been shown to induce uveitis in rats which could be inhibited with IL-1 blockers. Cytokines including IL-1, TNF and GM-CSF have been shown to stimulate proliferation of acute myelogenous leukemia blasts. IL-1 was shown to be essential for the development of both irritant and allergic contact dermatitis. Epicutaneous sensitization can be prevented by the administration of an anti-IL-1 monoclonal antibody before epicutaneous application of an allergen. Data obtained from IL-1 knock out mice indicates the critical involvement in fever for this cytokine. A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses. The production of these inflammatory cytokines rapidly follows trauma or pathogenic organism invasion.

In some embodiments, compounds of the present invention inhibit MAPKAPK2. Thus, in certain embodiments, the present invention provides a method of treated a MAPKAPK2-associated condition, the method comprising administering an effective amount of a compound of the present invention, or a pharmaceutically acceptable salt thereof, to a subject in need thereof. In certain embodiments, a MAPKAPK2-associated condition is a condition associated with TNF-α production. In certain embodiments, compounds of the present invention are useful for treating one or more of the following diseases: rheumatoid arthritis, psoriasis, Crohn's disease, dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalopathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. In addition, compounds dislosed herein may be useful for treating acute and chronic inflammation in the lung caused by inhalation of smoke such as cigarette smoke. TNF-α inhibitors may also be useful for the treatment of endometriosis, see EP 1022027 A1, as well as rheumatoid arthritis, psoriasis, ankylosing spondylitis, and psoriatic arthritis. The p38MAP kinase pathway plays an role in *B. burgdorferi*-elicited infammation and may be useful in treating inflammation induced by the Lyme disease agent.

Glycogen synthase kinase 3 (GSK3) is a serine/threonine protein kinase composed of two isoforms (a and J), which are encoded by distinct genes but are highly homologous within the catalytic domain. GSK3 is highly expressed in the central and peripheral nervous system. GSK3 phosphorylates several substrates including tau, β-catenin, glycogen synthase, pyruvate dehydrogenase and elongation initiation factor 2b (eIF2b). Insulin and growth factors activate protein kinase B, which phosphorylates GSK3 on serine 9 residue and inactivates it (Kannoji et al, *Expert Opin. Ther. Targets* 2008, 12, 1443-1455).

AD is characterized by cognitive decline, cholinergic dysfunction and neuronal death, neurofibrillary tangles and senile plaques consisting of amyloid-β deposits. The sequence of these events in AD is unclear, but is believed to be related. Glycogen synthase kinase 3β (GSK3β), or Tau phosphorylating kinase, selectively phosphorylates the microtubule associated protein Tau in neurons at sites that are hyperphosphorylated in AD brains. Hyperphosphorylated tau has lower affinity for microtubules and accumulates as paired helical filaments, which are the main components that constitute neurofibrillary tangles and neuropil threads in AD brains. This results in depolymerization of microtubules, which leads to death of axons and neuritic dystrophy. (Hooper et al, *J. Neurochem*. 2008, 104(6), 1433-1439). Neurofibrillary tangles are consistently found in diseases such as AD, amyotrophic lateral sclerosis, parkinsonism-dementia of Gaum, corticobasal degeneration, dementia pugilistica and head trauma, Down's syndrome, postencephalitic parkinsonism, progressive supranuclear palsy, Niemann-Pick's Disease and Pick's Disease. Addition of amyloid-β to primary hippocampal cultures results in hyperphosphorylation of tau and a paired helical filaments-like state via induction of GSK3β activity, followed by disruption of axonal transport and neuronal death (Imahori and Uchida, *J. Biochem*. 1997, 121, 179-188), while GSK3α has been postulated to regulate the production of amyloid-β itself (Phiel et al. *Nature*, 2003, 423, 435-439). GSK3β preferentially labels neurofibrillary tangles and has been shown to be active in pre-tangle neurons in AD brains. GSK3 protein levels are also increased by 50% in brain tissue from AD patients. Furthermore, GSK3β phosphorylates pyruvate dehydrogenase, a key enzyme in the glycolytic pathway and prevents the conversion of pyruvate to acetyl-Co-A (Hoshi et al, PNAS1996, 93: 2719-2723). Acetyl-Co-A is critical for the synthesis of acetylcholine, a neurotransmitter with cognitive functions. Accumulation of amyloid-β is an early event in AD. GSK transgenic mice show increased levels of amyloid-β in brain. Also, PDAPP (APpV717F) transgenic mice fed with lithium show decreased amyloid-β levels in hippocampus and decreased amyloid plaque area (Su et al, Biochemistry 2004, 43, 6899-6908). Likewise, GSK3 inhibition has been shown to decrease amyloid deposition and plaque-associated astrocytic proliferation, lower tau phosphorylation, protect against neuronal cell death, and prevent memory deficincies in a double APPsw-tauvrw mouse model (Sereno et al, Neurobiology of Disease, 2009, 35, 359-367). Furthermore, GSK3 has been implicated in synaptic plasticity and memory function (Peineau et al, *Neuron* 2007, 53, 703-717; Kimura et al, *PloS ONE* 2008, 3, e3540), known to be impaired in AD patients. GSK3 inhibition may have beneficial effects in progression as well as the cognitive deficits associated with Alzheimer's disease and other above-referred to diseases.

Growth factor mediated activation of the PI3K/Akt pathway has been shown to play a key role in neuronal survival. The activation of this pathway results in GSK3 inhibition. GSK3β activity is increased in cellular and animal models of neurodegeneration such as cerebral ischemia or after growth factor deprivation (Bhat et al., *PNAS* 2000, 97, 11074-11079). Several compounds with known GSK3β inhibitory effect has been shown to reduce infarct volume in ischemic stroke model rats. A recent publication (Koh et al, *BBRC* 2008, 371, 894-899) demonstrated that GSK-3 inhibition decreased the total infarction volume and improved neurobehavioral functions by reducing ischemic cell death, inflammation, brain edema, and glucose levels, in a focal cerebral ischemia model. Thus GSK3β inhibitors could be useful in attenuating the course of acute neurodegenerative diseases.

Bipolar disorders are characterized by manic episodes and depressive episodes. Lithium has been used to treat bipolar disorder based on its mood stabilizing effects. The disadvantage of lithium is the narrow therapeutic window and the danger of overdosing that can lead to lithium intoxication. The discovery that lithium inhibits GSK3 at therapeutic concentrations has raised the possibility that this enzyme represents a key target of lithium's action in the brain (Stambolic et al., *Curr. Biol*. 1996, 68, 1664-1668; Klein and Melton; *PNAS*1996, 93, 8455-8459; Gould et al, *Neuropsychopharmacology*, 2005, 30, 1223-1237). GSK3 inhibitor has been shown to reduce immobilization time in forced swim test, a model to assess on depressive behavior (O'Brien et al., *J Neurosci* 2004, 24, 6791-6798). GSK3 has been associated with a polymorphism found in bipolar II disorder (Szczepankiewicz et al, *Neuropsychobiology*, 2006, 53, 51-56). Inhibition of GSK3β may therefore be of therapeutic relevance in the treatment of bipolar disorder as well as in AD patients that have affective disorders.

Accumulating evidence implicates abnormal activity of GSK3 in mood disorders and schizophrenia. GSK3 is involved in signal transduction cascades of multiple cellular processes, particularly during neural development. (Kozlovsky et al, *Am. J. Psychiatry*, 2000, 157, 831-833) found that GSK3β levels were 41% lower in the schizophrenic patients than in comparison subjects. This study indicates that schizophrenia involves neurodevelopmental pathology and that abnormal GSK3 regulation could play a role in schizophrenia. Furthermore, reduced β-catenin levels have been reported in patients exhibiting schizophrenia (Cotter et al, *Neuroreport* 1998, 9, 1379-1383). Atypical antipsychotic such as olanzapine, clozapine, quetiapine and ziprasidone, inhibits GSK3 by increasing ser9 phosphorylation suggesting that antipsychotics may exert their beneficial effects via GSK3 inhibition (Li X. et al., *Int. J. of Neuropsychopharmacol*, 2007, 10, 7-19).

Type 2 diabetes mellitus is characterized by insulin resistance and β-cell failure. Insulin stimulates glycogen synthesis in skeletal muscles via dephosphorylation and thus activation of glycogen synthase and therefore increased glucose disposal. Under resting conditions, GSK3 phosphorylates and inactivates glycogen synthase via dephosphorylation. GSK3 is also over-expressed in muscles from Type II diabetic patients (Nikoulina et al, *Diabetes* 2000 February; 49(2), 263-71). Inhibition of GSK3 increases the activity of glycogen synthase thereby decreasing glucose levels by its conversion to glycogen. In animal models of diabetes, GSK3 inhibitors lowered plasma glucose levels up to 50% (Cline et al, *Diabetes*, 2002, 51: 2903-2910; Ring et al, *Diabetes* 2003, 52, 588-595). Moreover, results obtained by using haploinsufficient GSK3β mice on a diabetic background indicated that reduced GSK3β activity also protects from 3-cell failure (Tanabe et al, *PloS Biology*, 2008, 6(2), 307-318. GSK3 inhibition may therefore be of therapeutic relevance in the treatment of Type I and Type II diabetes to enhance insulin sensitivity and reduce 3-cell failure and therefore also relevant therapy to reduce diabetic complications like diabetic neuropathy.

GSK3 phosphorylates and degrades β-catenin. β-Catenin is an effector of the pathway for keratonin synthesis. β-Catenin stabilization may be lead to increase hair development. Mice expressing a stabilized β-catenin by mutation of sites phosphorylated by GSK3 undergo a process resembling de novo hair morphogenesis (Gat et al, *Cell*, 1998, 95, 605-14)). The new follicles formed sebaceous glands and dermal papilla, normally established only in embryogenesis. Thus, GSK3 inhibition may offer treatment for a variety of indications that lead to alopecia.

The discovery that GSK3 inhibitors provide anti-inflammatory effects has raised the possibility of using GSK3 inhibitors for therapeutic intervention in inflammatory diseases. (Martin et al, *Nat. Immunol.* 2005, 6, 777-784; Jope et al, *Neurochem. Res.* 2007, 32, 577-595). Inflammation is a common feature of a broad range of conditions including Alzheimer's Disease and mood disorders. A recent publication (Kitazawa et al, *Ann. Neurol.* 2008, 64, 15-24) indicates that GSK3β may play a role in inclusion body myositis (IBM).

GSK3 is over expressed in ovarian, breast and prostate cancer cells and recent data suggests that GSK3β may have a role in contributing to cell proliferation and survival pathways in several solid tumor types. GSK3 plays an important role in several signal transduction systems which influence cell proliferation and survival such as WNT, PI3 kinase and NFκB. GSK3 deficient MEFs indicate a crucial role in cell survival mediated NFκB pathway (Ougolkov et al., *Future Oncol.* 2006 Feb., 2(1), 91-100.). Thus, GSK3 inhibitors may inhibit growth and survival of solid tumors, including pancreatic, colon and prostate cancer. Growth control of multiple myeloma cells has been demonstrated through inhibition of GSK3 (Zhou et al., 2008 *Leuk. Lymphoma*, 48, 1946-1953). A recent publication (Wang et al, *Nature* 2008, 455, 1205-1209) demonstrated that GSK3 inhibition was efficacious in a murine model of MLL leukemia. Thus, GSK3 inhibitors may also inhibit growth and survival of hematological tumors, including multiple myeloma.

GSK3 inhibitors may also be used for therapeutic treatment of glaucoma. Elevated intraocular pressure (IOP) is the most significant risk factor for the development of glaucoma, and current glaucoma therapy focuses on reducing IOP, either by reducing aqueous humor production or by facilitating aqueous humor outflow. Recently published expression profiling experiments (Wang et al, *J. Clin. Invest.* 2008, 118, 1056-1064) have revealed that the soluble WNT antagonist sFRP-1 is overexpressed in ocular cells from glaucoma patients relative to control subjects. A functional link between WNT signaling pathways and glaucoma was provided through experiments in which addition of recombinant sFRP-1 to ex vivo-cultured human eye anterior segments resulted in a decrease in aqueous humor outflow; in addition, in vivo experiments in mice demonstrated that over expression of sFRP-1 in ocular tissues resulted in increases in intraocular pressure, an effect that was antagonized by a small-molecule GSK3 inhibitor. Taken together, the results reported by Wang et al. (2008) suggest that activation of WNT signaling via inhibition of GSK3 may represent a novel therapeutic approach for lowering intraocular pressure in glaucoma.

A recent publication (WO2008/057933) indicates that GSK3β inhibitors may play a role in the treatment of pain, particularly neuropathic pain, by modulation of glycogenolysis or glycolysis pathways.

Genetic studies have established a link between bone mass in humans and Wnt signaling (Gong et al, *Am. J. Hum. Genet* 1996, 59, 146-51, Little et al, *N. Engl. J. Med.*, 2002, 347, 943-4). Genetic and pharmacological manipulations of Wnt signaling in mice have since then confirmed the central role of this pathway in regulating bone formation. Of the pathways activated by Wnts, it is signaling through the canonical (i.e., Wnt/β-catenin) pathway that increases bone mass through a number of mechanisms including renewal of stem cells, stimulation of pre-osteoblast replication, induction of osteoblastogenesis, and inhibition of osteoblast and osteocyte apoptosis. Therefore, enhancing Wnt pathway signaling with GSK3 inhibitors alone or in combination with a suitable device could be used for the treatment of bone-related disorders, or other conditions which involve a need for new and increased bone formation for example osteoperosis (genetic, iatrogenic or generated through aging/hormone imbalance), fracture repair as a result of injury or surgery, chronic-inflammatory diseases that result in bone loss such as for example rheumatoid arthritis, cancers that lead to bone lesions, such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease.

Stem-cell expansion and differentiation are required for self-renewal and maintenance of tissue homeostasis and repair. The β-catenin-mediated canonical Wnt signaling pathway has been shown to be involved in controlling stem differentiation (Pinto et al., *Exp. Cell Res.*, 2005, 306, 357-63). A physiological Wnt response may be essential for the regeration of damaged tissues. GSK3 inhibitors by enhancing Wnt signaling may be useful to modulate stem cell function to enhance tissue generation ex vivo or in vivo in diseases associated with tissue damage or reduced tissue repair.

In some embodiments, compounds of the present invention inhibit GSK3P. Thus, in certain embodiments, the present invention provides a method of treated a GSK3β-associated condition, the method comprising administering an effective amount of a compound of the present invention, or a pharmaceutically acceptable salt thereof, to a subject in need thereof. GSK3 is highly expressed in the central and peripheral nervous system and in other tissues. Thus, in certain embodiments, provided compounds are effective for treating cognitive disorder(s) or indications with deficit(s) in cognition such as dementia, including pre-senile dementia (early onset Alzheimer's Disease), senile dementia (dementia of the Alzheimer's type), Alzheimer's Disease (AD), familial Alzheimer's disease, early Alzheimer's disease, mild to moderate dementia of the Alzheimer's type, delay of disease progression of Alzheimer's Disease, neurodegeneration associated with Alzheimer's disease, mild cognitive impairment (MCI), amnestic mild cognitive impairment (aMCI), age-associated memory impairment (AAMI), Lewy body dementia, vascular dementia (VD, HIV-dementia, AIDS dementia complex, AIDS-neurological complications, frontotemporal dementia (FTD), frontotemporal dementia Parkinson's type (FTDP), dementia pugilistica, dementia due to infectious agents or metabolic disturbances, dementia of degenerative origin, dementia-multi-infarct, memory loss, cognition in Parkinson's disease, cognition in multiple sclerosis, cognition deficits associated with chemotherapy, cognitive deficit in Schizophrenia (CDS), schizoaffective disorders including schizophrenia, age-related cognitive decline (ARCD), cognitive impairment no dementia (CIND), cognitive deficit arising from stroke or brain ischemia, congenital and/or development disorders, progressive supranuclear palsy (PSP), amyotrophic lateral sclerosis (ALS), corticobasal degeneration (CBD), traumatic brain injury (TBI), postencephalatic parkinsonism, Pick's disease, Niemann-Pick's disease, Down's syndrome, Huntington's disease, Creuztfeld-Jacob's disease, prion diseases, multiple sclerosis (MS), motor neuron diseases (MND), Parkinson's disease (PD), β-amyloid angiopathy, cerebral amyloid angiopathy, trinucleotide repeat fisorders, spinal muscular atrophy, Friedreich's ataxia, neuromyelitis optica, multiple system atrophy, transmissible spongiform encephalopathies, attention deficit disorder (ADD), attention deficit hyperactivity disorder (ADHD), bipolar disorder (BD) including acute mania, bipolar depression, bipolar maintenance, major depressive disorders (MDD) including depression, major depression, mood stabilization, dysthymia, agnosia, aphasia, apraxia, or apathy. In certain embodiments, a provided compound is used to treat Alzheimer's Disease, especially used in the delay of the disease progression of Alzheimer's Disease.

In certain embodiments, a provided compound is used for treatment of disorders selected from the group consisting of attention deficit disorder (ADD), attention deficit hyperactivity disorder (ADHD) and affective disorders, wherein the affective disorders are Bipolar Disorder including acute mania, bipolar depression, bipolar maintenance, major depressive disorders (MDD) including depression, major depression, mood stabilization, schizoaffective disorders including schizophrenia, and dysthymia.

In certain embodiments, a provided compound is used for treatment of Type I diabetes, Type II diabetes, diabetic neuropathy, pain including neuropathic pain, nociceptive pain, chronic pain, pain associated with cancer, pain associated with rheumatic disease, alopecia, glaucoma, inflammatory diseases, including inclusion body myositis (IBM), or pemphigus vulgaris.

In certain embodiments, a provided compound is useful for treatment of benign or malignant tumours including non-solid tumours such as leukaemia including MLL leukemia, myeloma including multiple myeloma, or lymphoma, and solid tumours, for example bile duct, bone, bladder, brain/CNS, breast, colorectal, endometrial, gastric, head, neck, hepatic, lung particularly, non-small-cell lung, neuronal, oesophageal, ovarian, pancreatic, prostate, renal, skin, testicular, thyroid, uterine and vulval cancers.

In certain embodiments, a provided compound is useful for treatment of bone related effects of specific cancers for example breast, prostate, lung cancer, multiple myeloma, osteosarcoma, Ewing's sarcoma, chondrosarcoma, chordoma, malignant fibrous histiocytoma of bone, fibrosarcoma of bone, cancer induced bone disease and iatrogenic bone disease.

In certain embodiments, a provided compound is useful for treatment of osteoporosis (genetic, iatrogenic or generated through aging/hormone imbalance), fracture repair as a result of injury or surgery, chronic-inflammatory diseases that result in bone loss such as for example rheumatoid arthritis, cancers that lead to bone lesions, such as for example cancers of the breast, prostate and lung, multiple myeloma, osteosarcoma, Ewing's sarcoma, chondrosarcoma, chordoma, malignant fibrous histiocytoma of the bone, fibrosarcoma of the bone, cancer induced bone disease, iatrogenic bone disease, benign bone disease and Paget's disease, for promoting bone formation, increasing bone mineral density, reducing the rate of fracture and/or increasing the rate of fracture healing, increasing cancellous bone formation and/or new bone formation.

The present invention further provides a method of inhibiting an enzyme, the method comprising contacting a compound of the present invention, or a pharmaceutically acceptable salt thereof, with an enzyme in an amount sufficient to inhibit the enzyme's activity. In some embodiments, the present invention provides a method of inhibiting O-GlcNac transferase, the method comprising contacting a compound of the present invention, or a pharmaceutically acceptable salt thereof, with O-GlcNAc transferase in an amount sufficient to inhibit the activity of O-GlcNAc transferase. The O-GlcNAc transferase may be purified or crude, and may be present in a cell, tissue, or subject. Thus, such methods encompasses both inhibition of in vitro and in vivo OGT activity. In certain embodiments, the method is an in vitro method, e.g., such as an assay method useful as a research tool. Research tools contemplated may be assays in assessing a particular compound's inhibitory activity against OGT or OGT pathway, e.g., in the SAR study of the molecular scaffold.

In some embodiments, the present invention provides a method of inhibiting a kinase, the method comprising contacting a compound of the present invention, or a pharmaceutically acceptable salt thereof, with a kinase in an amount sufficient to inhibit kinase activity. Exemplary kinases are described herein. In some embodiments, the present invention provides a method of inhibiting PLK1, PLK2, PLK3, and/or PLK4, the method comprising contacting a compound of the present invention, or a pharmaceutically acceptable salt thereof, with PLK1, PLK2, PLK3, and/or PLK4 in an amount sufficient to inhibit kinase activity. In some embodiments, the present invention provides a method of inhibiting MAPKAPK2, the method comprising contacting a compound of the present invention, or a pharmaceutically acceptable salt thereof, with MAPKAPK2 in an amount sufficient to inhibit kinase activity. In some embodiments, the present invention provides a method of inhibiting GSK-3β, the method comprising contacting a compound of the present invention, or a pharmaceutically acceptable salt thereof, with GSK-3β in an amount sufficient to inhibit kinase activity. The kinase may be purified or crude, and may be present in a cell, tissue, or subject. Thus, such methods encompasses both inhibition of in vitro and in vivo kinase activity. In certain embodiments, the method is an in vitro method, e.g., such as an assay method useful as a research tool. Research tools contemplated may be assays in assessing a particular compound's inhibitory activity against a kinase or kinase pathway, e.g., in the SAR study of the molecular scaffold.

In certain embodiments, a compound of the invention is selective for a particular target. In certain embodiments, a provided compound is a selective OGT inhibitor. In certain embodiments, a provided compound is a selective kinase inhibitor. In certain embodiments, a provided compound is selective for PLK1. In certain embodiments, a provided compound is a selective GSK3β inhibitor. In certain embodiments, a provided compound is a selective MAPKAPK2 inhibitor. In certain embodiments, a selective kinase inhibitor is at least 2 times, 5 times, 10 times, 20 times, 50 times, 100 times, 200 times, 500 times, or 1000 times more active against a particular kinase of interest than other representative (off-target) kinases in an in vitro assay.

The present invention further provides a method of covalently modifying a protein, the method comprising reacting a compound of the present invention, or a pharmaceutically acceptable salt thereof, with a protein, to provide a covalently modified protein. In some embodiments, the present invention provides a method of covalently modifying O-linked N-acetylglucosamine (O-GlcNAc) transferase, the method comprising reacting a compound of the present invention, or a pharmaceutically acceptable salt thereof, with O-GlcNAc transferase, to provide a covalently modified O-GlcNAc transferase. In other embodiments, the present invention provides a method of covalently modifying a kinase (e.g., PLK1), the method comprising reacting a compound of the present invention, or a pharmaceutically acceptable salt thereof, with a kinase, to provide a covalently modified kinase. Covalent modification refers to the synthetic functionalization of one or more amino acid residues of an enzyme (e.g., O-GlcNAc transferase). For example, in certain embodiments, O-linked N-acetylglucosamine (O-GlcNAc) transferase is covalently modified at a cysteine residue, e.g., covalent modification of the side chain —SH group. In certain embodiments, the O-linked N-acetylglucosamine (O-GlcNAc) transferase is covalently modified at a lysine residue, e.g., covalent modification of the side chain —NH$_2$ group. In certain embodiments, the O-linked N-acetylglucosamine (O-GlcNAc) transferase is covalently modified at a lysine and a cysteine residue. In other embodiments, a kinase is covalently modified by a compound of the present invention at a lysine residue, or a cysteine residue, or both a lysine and a cysteine residue. In certain embodiments, the lysine and cysteine residue of the covalently modified O-linked N-acetylglucosamine (O-GlcNAc) transferase are cross-linked via a carbamothioate linkage:

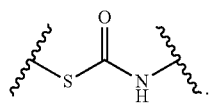

EXAMPLES

In order that the invention described herein may be more fully understood, the following examples are set forth. It should be understood that these examples are for illustrative purposes only and are not to be construed as limiting this invention in any manner.

Example 1

Benzoxazolinone (BZX) Compounds Irreversibly Inactivate OGT

Figure 1:
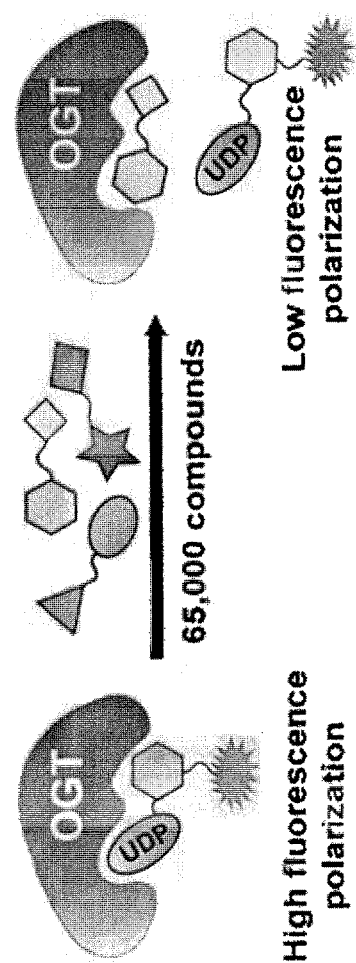
FIG. 1 depicts a schematic of a high-throughput fluorescence-based displacement screen used to identify a benzoxazolinone (BZX) inhibitor of OGT, see, e.g., Gross et al., J. Am. Chem. Soc. (2005) 127:14588-14589. The UDP-GlcNAc substrate analog shown represents fluorescein-labeled UDP-GlcNAc.
Figure 2:
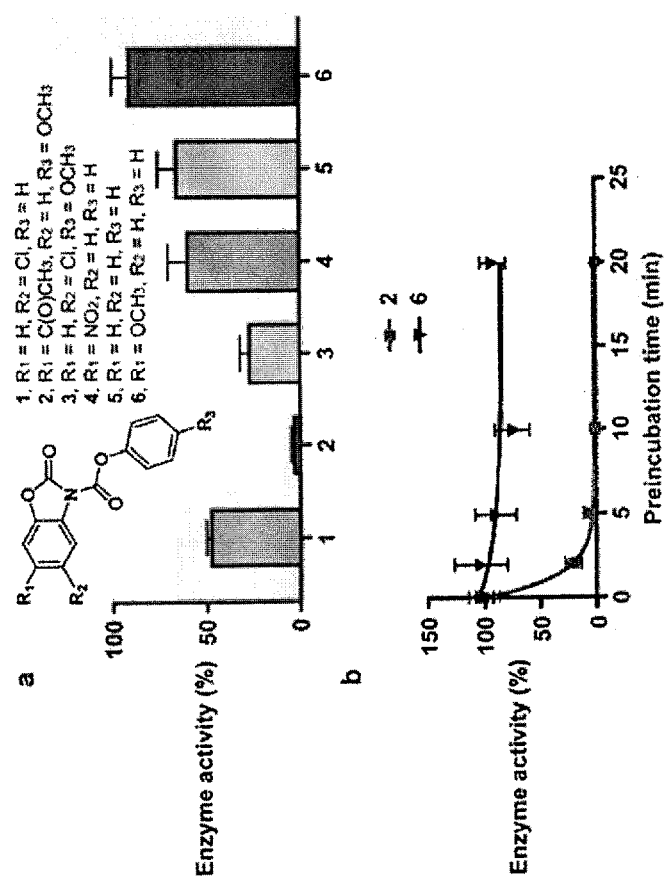
FIG. 2 depicts the inactivation of OGT by BZX compounds.

Compound (1) was identified in a high-throughput screen of 65,000 compounds (FIG. 1). See, e.g., Gross et al., *J. Am. Chem. Soc.* (2005) 127:14588-14589. It contains a dicarbamate moiety that links two aromatic groups. This compound features a conjugated chemical structure and both carbamate carbonyls are potentially reactive. See, e.g., Alexander et al., *Chem. Biol.* (2005) 12:1179-1187. Indeed, preincubation of OGT with compound (1) caused an irreversible loss of enzyme activity, consistent with covalent modification of the enzyme. A small panel of related compounds was made from commercially available building blocks in order to identify structural features that might improve potency. Time-dependent inactivation studies were carried out in which OGT was preincubated with a three-fold excess of each compound for 5 min, and the mixture was then diluted 100-fold into buffer containing UDP-$^{14}$C-GlcNAc and the well-characterized peptide substrate, CKII. See, e.g., Kreppel et al., *J. Biol. Chem.* (1999) 274:32015-32022). Enzyme activity was measured using a previously developed peptide capture assay. See, e.g., Gross et al., *J. Am. Chem. Soc.* (2005) 127:14588-14589. Several inhibitors showed an irreversible reduction in enzymatic activity (FIG. 2a). The best compound, (2), contains a ketone on the BZX core and a p-methoxy group on the phenyl ring.

An inactivation time course shows that compound (2) fully inactivated OGT at a 1.5:1 of inhibitor:enzyme ratio (FIG. 2b). In contrast, compound (6) exhibited no inhibition, implying that enzyme inactivation by BZX compounds is not due to non-specific effects. We also tested OGT inactivation by compound (2) in the presence of UDP-GlcNAc in the preincubation mixture (FIG. 7). UDP-GlcNAc reduced the rate of inactivation, suggesting that binding of this substrate competes with inhibitor binding. This result is consistent with discovery of the BZX inhibitors in a glycosyl donor displacement assay. See, e.g., Gross et al., *J. Am. Chem. Soc.* (2005) 127:14588-14589. The apparent IC$_{50}$ of compound (2) was 1.6±1.1 µM. It is a more potent inhibitor of OGT activity than compound (1) in cell lysates, and it also inhibits O-GlcNAcylation in cells (FIG. 8).

Example 2

Two Covalent Adducts Identified Using Intact Protein Mass Spectrometry

To identify possible covalent adducts, we analyzed intact protein mass spectra of hOGT$_{4.5}$ after a five-minute incubation with compound (2) at a 1:1 ratio. The hOGT$_{4.5}$ construct has the same catalytic activity towards peptide substrates as the full length enzyme, but its N-terminal domain is truncated (Lazarus et al., *Nature* (2011) 469:564-567). The smaller mass of this construct is advantageous for MS analysis. Following incubation, the enzyme mixture was analyzed using LC-ESI-Q-TOF-MS. Two covalent adducts were detected (FIG. 3a). The major adduct had a mass increase of +26 Da, consistent with the incorporation of C═O and the loss of two protons. The minor adduct had a mass increase of +176 Da, and a possible structure for this adduct is shown (FIG. 3a).

Example 3

Covalent Modifications Map to an Essential Catalytic Lysine Residue

To identify the side chains that react with compound (2), we analyzed tryptic digests of OGT in the presence and absence of the inhibitor using LC-ESI-MS/MS. The data files were searched against the SwissProt database using the MS/MS ion search feature of the Mascot search engine. There was a notable difference in the patterns of the digests for the control and inhibitor-treated proteins. A triply charged 34 residue peptide (S$_{823}$QYGLPEDAIVYYCNFNQLY KIDPSTLQMWANILK$_{856}$) was observed in digests of incubated protein, which was not seen in the control sample. Based on the b and y ions generated from CID fragmentation, both the +26 and +176 modifications were assigned to the same active site residue, K842, which plays an essential role in catalysis (see below). K842 is a trypsin cleavage site and its modification blocks proteolysis, explaining the appearance of a new, longer peptide fragment in the treated protein. For the +176 modification, good fragmentation was observed throughout the 34 amino acid peptide. For the +26 modification, no fragment ions were detected between C835-Y841, although fragmentation was good on both sides. Peptide fragmentation may have been affected by the type of modification (see below).

The intact protein mass spectra of WT enzyme and a K842A mutant following incubation with compound (2) were compared. Neither the +26 nor the +176 modification was observed in the alanine mutant (FIG. 3b); however, we observed a new +150 Da mass peak, and a structure consistent with this adduct is shown. This modification mapped to C835 based on analysis of tryptic digests. Like K842, C835 is located in the active site of OGT.

Example 4

Proposed Mechanism for the Generation of the Major Covalent Adduct

A +26 modification implies incorporation of a C=O from (2), which requires a double displacement by two active site nucleophiles. There are two general mechanisms by which such a modification could arise, one involving attack on the cyclic carbonyl and the other due to attack on the acyclic carbonyl (FIG. 4). Although the reaction pathways to product could be complex, these mechanisms would produce different possible leaving groups. Therefore, we analyzed the leaving groups generated by incubation of compound (2) with OGT at a 1:1 ratio. The incubated enzyme mixture was tested via LC-MS with $UV_{287nm}$ detection. After incubation with OGT, the compound (2) parent peak (20 min) disappeared, and two new peaks at 12 and 13 min were observed (FIG. 4). Their elution times and exact masses were identical to authentic standards of 4-methoxyphenol and 6-acetyl-2-benzoxazolinone, respectively. The calculated concentration ratio of these two leaving groups is 1:1 based on their integrated UV area normalized to the extinction coefficients at 287 nm. This is consistent with the double displacement mechanism shown in FIG. 4, in which the origin of the incorporated C=O is the carbonyl of the acyclic carbamate. It was noted that +150 adducts on cysteine thiols are frequently observed when the inhibitor is used in significant excess, implying that the BZX core is a preferred leaving group following the first attack on the acyclic carbonyl.

Example 5

Characterization of Active Site Mutants to Identify the Crosslinking Partner

A double displacement mechanism for formation of the +26 mass adduct implies that another active site nucleophile in addition to K842 reacts with compound (2). We speculated that mutation of the crosslinking partner would result in accumulation of a +150 adduct on K842, corresponding to a single displacement on the acyclic carbonyl. To identify the crosslinking partner, we individually mutated all residues containing a nucleophilic side chain within 10 Å of K842 in the active site of OGT, which included Y841, C911, T914, C917, T921, and T922. From analysis of the intact protein MS for each mutant after incubation with compound (2) at a 1:1 ratio, three different outcomes were observed: 1) the mutation had no effect compared with WT enzyme, e.g., Y841A (FIG. 10a); 2) the mutation appeared to shift the ratio of the +26 and +176 modifications, e.g., T921A and T922A (FIG. 10b); or 3) the mutation resulted in the appearance of a new +150 mass peak in addition to altering the distribution of +26 and +176 modifications, e.g., C917A (FIG. 10c). The threonine mutations (T921A and T922A) that shifted the ratio of the two modifications flank the diphosphate binding site. Since only C917 resulted in significant accumulation of a +150 adduct on K842, it was concluded that this side chain is the major crosslinking partner. It was also noted that C917A mutant did not fully abolish the +26 modification, implying that other active site nucleophiles may react in its absence. In contrast, both major (+26; double displacement adduct) and minor (+176; single displacement adduct) modifications disappeared upon mutation of lysine 842 to alanine, suggesting the amino group of K842 initiates crosslink formation.

Example 6

Crystal Structure Shows the Active-Site Crosslink

A C=O crosslink bridging two active site residues is an unprecedented mechanism of inhibition. Therefore, it was sought to crystallize the inhibitor-treated $hOGT_{4.5}$. The enzyme was incubated with compound (2) to generate crosslinked protein and then crystallized in the presence of UDP and CKII under the same conditions as we reported previously for the OGT-UDP-CKII complex. See, e.g., Lazarus et al., Nature (2011) 469:564-567. We obtained trapezoidal crystals that diffracted to 1.875 Å in the same space group. The refined structure is similar to the one without inhibitor treatment, and UDP and the CKII peptide are bound in similar conformations, but there is a notable difference in the active site. In the inhibitor structure, the 2Fo-Fc omit map shows significant electron density connecting K842 and C917 (FIG. 5a), which was not observed in the native structure (FIG. 5b). In addition, to form the C=O crosslink, the side chain C—N bond of K842 has rotated 120° towards the C917 thiol, moving it away from the β-phosphate (FIG. 5c). This crystal structure shows a remarkable view of a C=O crosslink between two active site residues and also provides concrete evidence for the double displacement mechanism.

Example 7

The Dicarbamate is a Neutral Diphosphate Mimic

Since the benzoxazolinone (BZX) inhibitors are reactive, it is not possible to obtain crystallographic information with an intact inhibitor bound. Glide computational modeling software was used to dock the pre-reactive compound (2) to OGT. See, e.g., Friesner et al., J. Med. Chem. (2004) 47:1739-1749; Halgren et al., J. Med. Chem. (2004) 47:1750-1759; Friesner et al., J. Med. Chem. (2006) 49:6177-6196. Docking was carried out using protein coordinates from the OGT-UDP-CKII structure (PDB 3PE4) after removal of ligands. Computational experiments were conducted independently with 50 different starting poses of the inhibitor. The top-scoring ligand pose from each experiment was superimposed on the nucleotide substrate. The dicarbamate of inhibitor aligns with the substrate diphosphate in all fifty cases (FIG. 11). There are some differences in the details of the docked structures. For example, in the majority of cases the BZX group is located in the UDP binding pocket, but in a few the orientation of the molecule is flipped and it is located in the GlcNAc binding pocket. Nevertheless, the dicarbamate is located in the same place, with the lysine 842 amine positioned between the two carbonyls. A representative pose highlights the overlap between the dicarbamate and diphosphate binding site (FIG. 6). The docking models are consistent with inhibitor labeling of K842 as well as the MS data showing that mutation of residues T921 and T922, which form part of the diphosphate binding site, perturb the +26 and +176 product ratios (FIG. 10b). It was therefore concluded that the dicarbamate element functions as a neutral diphosphate mimic.

Discussion

To discover new types of inhibitors, a high-throughput glycosyl donor displacement screen was developed for OGT in which dicarbamate compound (1) was identified. See, e.g., Gross et al., *J. Am. Chem. Soc.* (2005) 127:14588-14589. Time-dependent inactivation studies showed that compound (1) covalently modifies OGT by reacting in the active site. However, MS analyses of intact protein treated with compound (1) were consistent with more than one site of labeling (FIG. 12), and peptide mapping studies showed reaction with surface cysteine residues. Therefore, a small panel of compounds was made, including a set with substituents having different electron-donating properties in the para position of the phenyl ring. Compound (2), which contains a p-methoxy substituent, fully inactivated OGT within 5 min at a near 1:1 ratio. Hence, unlike compound (1), most of compound (2) reaches the active site without being inactivated by unproductive side reactions. Excess compound (2) still results in non-specific labeling of surface residues.

It has been shown that compound (2) forms a major OGT adduct with a +26 Da mass increase, implying a C=O crosslink. Such an adduct would arise from a double displacement by two active site nucleophiles on one dicarbamate carbonyl. Using a combination of MS analysis, mutational studies, and X-ray crystallography, the inventors of the subject invention have confirmed a double displacement mechanism and have identified K842 and C917 as the side chains that participate in formation of the crosslink. The data suggest that productive reaction primarily occurs via attack on the acyclic carbonyl, although occasional reaction at the cyclic carbonyl cannot be excluded. Compound (2) is the first inhibitor described to have a mechanism of action that involves crosslinking active site residues of an enzyme.

The glycosyl donor displacement screen that led to the discovery of compound (2) was designed to identify possible diphosphate isosteres. Indeed, it has been shown that the rigid five-heteroatom core of compound (2) is a mimic of the OGT glycosyl donor diphosphate. The five heteroatoms are positioned in the same location in a similar conformation as the bound diphosphate. Furthermore, computational docking studies show that the dicarbamate carbonyls bind such that K842 is located between them and less than 3 Å away. This model is consistent with identification of this active site lysine as the major nucleophile labeled by the inhibitor. K842 is an essential side chain for catalysis. Previous X-ray crystal structures of hOGT$_{4.5}$ show that the K842 amino group contacts the β-phosphate of the substrate, suggesting that it facilitates movement of the UDP leaving group away from the glycopeptide bond as the glycosyl transfer reaction proceeds. It is invariant in OGT homologs and the K842A mutant has no detectable enzymatic activity (FIG. 13). See, e.g., Martinez-Fleites et al., *Nat. Struct. Mol. Biol.* (2008) 15:764-765. Hence, a family of compounds has been identified that covalently label the same residue that anchors the substrate diphosphate. The uncharged dicarbamate motif is cell permeable since compound (2) inhibits global O-GlcNAcylation in cells. However, the concentrations required for cellular activity are significantly higher than the concentrations used for in vitro inhibition. This is likely due to compound inactivation before it reaches its target.

General Method in the Synthesis of BZX Compounds

A solution of the benzoxalolinone (3.0 mol) in THF (10 ml) with distilled triethylamine (3.0 mmol) was dissolved in 10 mL of dry tetrahydrofuran (THF). The solution was cooled at 4° C. in an ice bath. The chloroformate (3.0 mol) in 20 mL was added dropwise over a period of 5 min. The reaction mixture was stirred for 12 h at rt. The solution was then filtered, and the filtrate was evaporated to dryness. The resultant solid was triturated with dry diethyl ether and was recrystallized from chloroform to yield the desired product.

Characterization of BZX Compounds Synthesized Via the General Method

Characterization of compound 2:

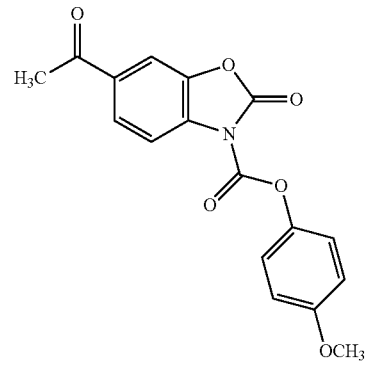 [SMILES: COc1ccc(OC(=O)n2c(=O)oc3cc(C(C)=O)ccc32)cc1]

$^1$H NMR (CDCl$_3$, 400 MHz): δ 7.93 (s, 2H), 7.86 (s, 1H), 7.23 (d, J=9.00 Hz, 2H), 6.97 (d, J=9.00 Hz, 2H), 3.84 (s, 3H), 2.64 (s, 3H); $^{13}$C NMR (CDCl$_3$, 100 MHz): δ 195.86, 158.14, 148.35, 148.07, 143.21, 142.15, 134.70, 130.89, 125.86, 121.91, 114.74, 114.56, 109.81, 55.66, 26.57; ESI-MS (m/z): [M+H]$^+$ calcd. for C$_{17}$H$_{14}$NO$_6$, 328.08. found 328.08.

Characterization of compound 3:

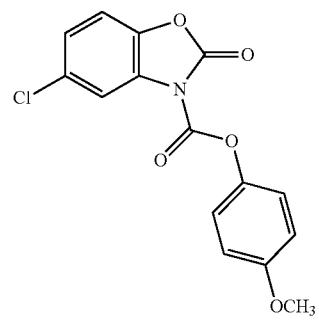 [SMILES: COc1ccc(OC(=O)n2c(=O)oc3ccc(Cl)cc32)cc1]

$^1$H NMR (CDCl$_3$, 400 MHz): δ 7.87 (d, J=1.96 Hz, 1H), 7.26-7.30 (m, 1H), 7.17-7.24 (m, 3H), 6.93-6.99 (m, 2H), 3.84 (s, 3H); $^{13}$C NMR (CDCl$_3$, 100 MHz): δ 158.12, 148.35, 147.98, 143.20, 140.44, 130.36, 127.87, 125.42, 121.95, 115.45, 114.72, 111.05, 55.66; ESI-MS (m/z): [M+H]$^+$ calcd. for C$_{15}$H$_{11}$ClNO$_5$, 320.03. found 320.03.

Characterization of compound 4:

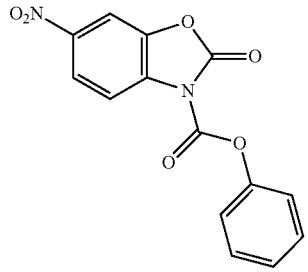 [SMILES: O=C(Oc1ccccc1)n1c(=O)oc2cc([N+](=O)[O-])ccc21]

$^1$H NMR (DMSO-d$_6$, 400 MHz): δ 8.40 (d, J=2.35 Hz, 1H), 8.26 (dd, J=2.35, 9.00 Hz, 1H), 7.94 (d, J=9.00 Hz, 1H), 7.48-7.58 (m, 2H), 7.34-7.42 (m, 3H); $^{13}$C NMR (DMSO-d$_6$, 100 MHz): δ 150.02, 148.62, 147.61, 144.74, 141.90, 133.39, 130.40, 127.48, 121.86, 121.39, 115.22, 106.58; ESI-MS (m/z): [M+H]$^+$ calcd. for C$_{14}$H$_9$N$_2$O$_6$, 301.05. found 301.05.

Characterization of compound 5:

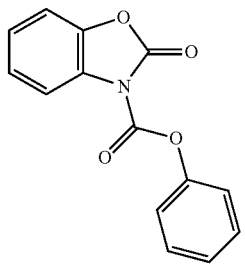 [SMILES: O=C(Oc1ccccc1)n1c(=O)oc2ccccc21]

$^1$H NMR (CDCl$_3$, 400 MHz): δ 7.81-7.89 (m, 1H), 7.42-7.52 (m, 2H), 7.27 (br. s., 6H); $^{13}$C NMR (CDCl$_3$, 100 MHz): δ 149.82, 148.72, 147.95, 142.03, 129.76, 127.09, 126.93, 125.43, 124.79, 121.20, 114.90, 110.22; ESI-MS (m/z): [M+H]$^+$ calcd. for C$_{14}$H$_{10}$NO$_4$, 256.06. found 256.06.

Characterization of compound 6:

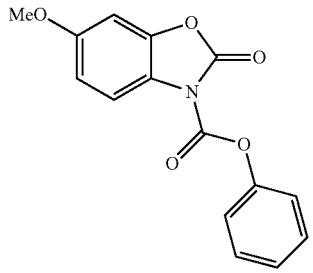 [SMILES: COc1ccc2c(c1)oc(=O)n2C(=O)Oc1ccccc1]

$^1$H NMR (CDCl$_3$, 400 MHz): δ 7.71 (d, J=8.61 Hz, 1H), 7.41-7.53 (m, 2H), 7.28-7.38 (m, 3H), 6.85 (d, J=2.35 Hz, 1H), 6.80 (dd, J=2.35, 8.61 Hz, 1H), 3.84 (s, 3H); $^{13}$C NMR (CDCl$_3$, 100 MHz): δ 157.85, 149.84, 149.01, 147.96, 142.81, 129.73, 126.87, 121.23, 120.37, 115.31, 110.07, 97.17, 55.93; ESI-MS (m/z): [M+H]$^+$ calcd. for C$_{15}$H$_{12}$NO$_5$, 286.07. found 286.07.

Synthesis of Thiocarbamate Compounds

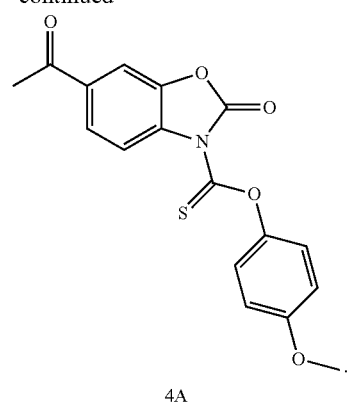

4A

Step 1

A solution of phenol (1A) (124 mg, 1 mmol) in 5% NaOH (5 mL) was added to a solution of thiophosgene (76 uL, 1 mmol) in chloroform (4 mL). The reaction was stirred for 5 h at 0° C. and the reaction was quenched with aqueous NH$_4$Cl. The mixture was washed with diluted HCl and water. The organic layer was dried over Na$_2$SO$_4$, filtrated, and concentrated in vacuo. The residue was purified by flash column chromatography (EtOAc/hexane) to give product (2A) (150 mg).

Step 2

A solution of phenol (2A) (101 mg, 0.5 mmol) and (3A) (88 mg, 0.5 mmol) in THF (5 mL) was added Et$_3$N (136 uL, 1 mmol). The reaction was stirred at 0-10° C. until the reaction went to completion. The mixture was concentrated in vacuo and purified by prep-HPLC to give final product (4A) as a gray solid (55 mg). $^1$H NMR (400 MHz, DMSO-d$_6$): δ 8.12 (d, J=8.22 Hz, 1H), 7.99 (d, J=1.17 Hz, 1H), 7.94 (dd, J=1.57, 8.61 Hz, 1H), 7.20 (d, J=9.00 Hz, 2H), 7.06 (d, J=9.00 Hz, 2H), 3.79 (s, 3H), 2.61 (s, 3H); $^{13}$C NMR (100 MHz, DMSO-d$_6$): δ 196.81, 183,24, 158.25, 149.11, 145.98, 141.48, 134.56, 131.86, 125.57, 123.47, 115.98, 115.33, 110.12, 56.00, 27.25; ESI-MS (m/z): [M+H]$^+$ calcd. for C$_{17}$H$_{14}$NO$_5$S, 344.06. found 344.06.

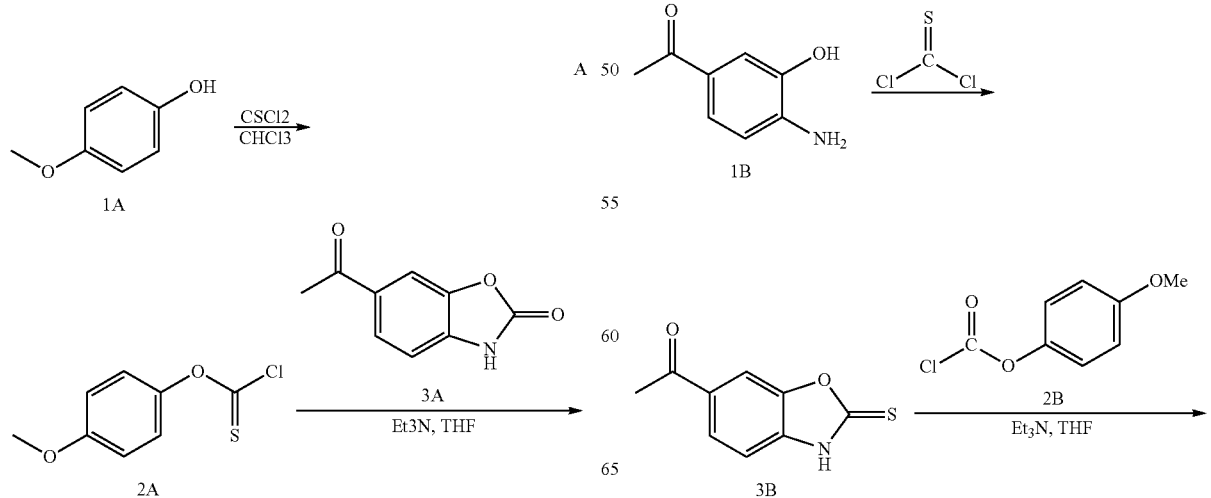

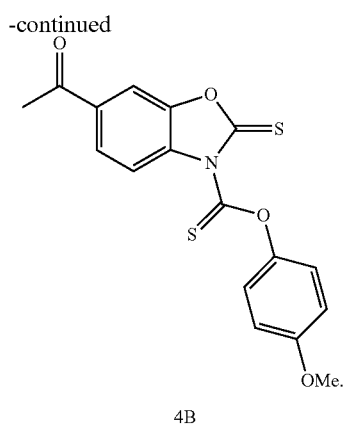

4B

Compound (4B) was synthesized in a manner similar to that of compound (4A), using compound (1B) in place of (1A), compound (2B) in place of (2A), and compound (3B) derived from compound (1B) and thiophosgene in place of (3A). Characterization of compound 4B: $^1$H NMR (400 MHz, DMSO-$d_6$): δ 8.14 (s, 1H), 8.04 (dd, J=1.17, 8.61 Hz, 1H), 7.90 (d, J=8.61 Hz, 1H), 7.38 (d, J=9.00 Hz, 2H), 7.07 (d, J=9.00 Hz, 2H), 3.80 (s, 3H), 2.64 (s, 3H); $^{13}$C NMR (100 MHz, DMSO-$d_6$): δ 196.88, 177.23, 158.16, 148.31, 146.35, 143.48, 135.02, 132.95, 126.55, 122.84, 115.89, 115.19, 110.12, 56.02, 27.36; ESI-MS (m/z): [M+H]$^+$ calcd. for $C_{17}H_{14}NO_5S$, 344.06. found 344.06.

Protein Purification.

The expression and purification of the hOGT$_{4.5}$ construct (spanning residues 313-1031 based on the numbering of the full length human protein) were performed following previously described protocols. See, e.g., Lazarus et al., *Nature* (2011) 469:564-567. The desired mutations were introduced by using the Stratagene QuikChange II XL Site-Directed Mutagenesis Kit and DNA from plasmid of hOGT$_{4.5}$ as template in combination with the mutagenic primers listed in Table 1 (nucleotide substitutions are underlined). The mutants were purified similarly as WT protein.

Time-Dependent Inactivation of OGT with BZX Compounds.

Each BZX compound (7.5 μM) was preincubated with 5 μM OGT in reaction buffer (125 mM NaCl, 1 mM EDTA, 20 mM potassium phosphate, pH 7.4, and 500 μM tris(hydroxypropyl)phosphine (THP)) at room temperature for different amount of time, then diluted 100-fold, mixed with substrates (6 μM UDP-$^{14}$C-GlcNAc and 500 μM CKII peptide (KK-KYPGGSTPVSSANMM)) and allowed to react for another 2 h. Enzyme activity was tested with the peptide capture assay as previously reported. See, e.g., Gross et al., *J. Am. Chem. Soc.* (2005) 127:14588-14589. The final volume of each reaction was 20 μl, and the experiments were conducted in triplicate. The activities of OGT mutants were also tested in triplicate as previously reported. See, e.g., Gross supra.

IC50 Assay of Thiocarbamate to OGT.

Enzyme activity was tested with the peptide-capture assay in the presence of different concentrations of each compound as previously reported (*J. Am. Chem. Soc.* 2005, 127, 14588-14589).

IC$_{50}$ Values
Compound 2: 2 μM
Compound 3: 18 μM
Compound 4: 60 μM
Compound 5: >100 μM
Compound 6: ~100 μM
Compound 4A: 14 μM
Compound 4B: ~100 μM Intact Protein Mass Spectrometry.

Each of the BZX compounds (10 μM) was incubated with OGT (10 μM) at room temperature for 5 min in the reaction buffer containing PBS (pH 7.5) and 100 μM THP, in a final volume of 20 μl. After incubation, 50 μl of PBS (pH 7.5) was added to each reaction, and the total 70 μl of mixture was passed through a PD SpinTrap G-25 column (GE Healthcare, pre-equilibrated with PBS, pH 7.5) to remove the non-enzymatic fraction. Eluted sample (40 μl each) was injected in an Agilent 6520 Q-TOF LC-MS. The mobile phase flow rate was set at 0.4 ml/min through a C4 column

TABLE 1

| Primer | Sequence (5' to 3') | SEQ ID NO |
|---|---|---|
| Y841A forward | ctgcaacttcaaccagctggccaaaatcgacccgtctacc | SEQ ID NO 1 |
| Y841A reverse | ggtagacgggtcgattttggccagctggttgaagttgcag | SEQ ID NO 2 |
| K842A forward | caacttcaaccagctgtacgcaatcgacccgtctaccctg | SEQ ID NO 3 |
| K842A reverse | cagggtagacgggtcgattgcgtacagctggttgaagttg | SEQ ID NO 4 |
| C917A forward | ggacaccccgctggccaacggtcacacc | SEQ ID NO 5 |
| C917A reverse | ggtgtgaccgttggccagcggggtgtcc | SEQ ID NO 6 |
| T921A forward | tgtgcaacggtcacgccaccggtatggac | SEQ ID NO 7 |
| T921A reverse | gtccataccggtggcgtgaccgttgcaca | SEQ ID NO 8 |
| T922A forward | gcaacggtcacaccgccggtatggacgtt | SEQ ID NO 9 |
| T922A reverse | aacgtccataccggcggtgtgaccgttgc | SEQ ID NO 10 |

(Grace, Vydac 214MS C4 5 u, 100×2.1 mm) which was initially equilibrated with solvent A (0.1% aqueous formic acid). The proteins were eluted using a linear gradient of 0 to 95% solvent B (90% acetonitrile and 0.1% aqueous formic acid) over 25 min. Mass spectrometric analyses were carried out in positive ion mode with an ESI source. The MS spectra were deconvoluted using Agilent MassHunter Bio-Confirm B.02.00 software with the maximum entropy algorithm.

Trypsin Digestion and Peptide Mass Spectrometry.

The reaction mixture containing OGT (15 μM), (2) (200 μM), $NH_4HCO_3$ (25 mM, pH 7.8), and THP (100 μM) in a final volume of 23 μl was incubated for 30 min at room temperature. To avoid complications with over alkylation, cysteines were not "capped," and the formation of disulfides was prevented by the presence of THP. Trypsin was added to a final OGT:trypsin concentration ratio of 6:1 (w/w) and the reaction was incubated for 4 h at 37° C. The peptides were separated using an Agilent 6520 LC/QTOF system equipped with a Phenomenex Gemini-NX C18 column (5 μm, 110 Å, 50×2.00 mm, pre-equilibrated with 0.1% aqueous formic acid) at a flow rate of 0.4 ml/min with a linear gradient of 0 to 60% buffer B (90% acetonitrile and 0.1% aqueous formic acid) over 50 min. Mass spectra were acquired from m/z 300-3200 for 0.25 s, followed by MS/MS scans from m/z 50-3200 of the eight most intense species from the preceding MS scan for 0.25 s each in positive ion mode with collision energy fixed at 35 V. All spectra were processed with Mascot Distiller (Matrix Sciences) to generate the peak lists. Database searches were performed with Mascot Server 2.3 (Matrix Sciences). Error tolerant search was performed following the standard search to maximize the matches. The significance threshold was set p<0.05, and the false discovery rate based on a decoy database was below 2%.

Crystallization and Crystal Structure Determination.

Native OGT-UDP-CKII peptide crystals were grown as described previously, see, e.g., Lazarus et al., *Nature* (2011) 469:564-567: crystals were obtained by mixing 2 μl OGT-UDP-CKII complex (7 mg/ml) with 1 μl reservoir containing 1.6 M $Li_2SO_4$ and 0.1M Bis Tris Propane, pH 7.0. Next, OGT (7 mg/ml) was incubated with (2) (200 μM final concentration, from a 40 mM DMSO stock solution) for 1 day at 4° C. Next, UDP and CKII peptide were added to the inhibitor-modified protein, and drops were set up as for the native. After several hours, seeds were made of the native crystals using the Seed Bead Kit (Hampton) and added to the inhibitor drops. After 2 days, small crystals appeared. This first generation of the crystals was used as seeds to set up the second generation of crystals similarly. These crystals were then frozen in a cryprotectant consisting of 1.72 M $Li_2SO_4$, 0.05 M Bis Tris Propane, pH 7.0, and 28% xylitol.

Compound (2) inhibitor crystals were grown with the hanging drop method with $hOGT_{4.5}$, seeded from native OGT-UDP-CKII crystals. The space group of OGT-(compound 2)-UDP-CKII complex was I121, the same as the original OGT-UDP-CKII complex (PDB 3PE4). The data set was indexed and integrated with iMosflm and then scaled using Scala to a resolution of 1.875 Å. See, e.g., Leslie *Joint CCP4+ESF-EAMCB Newsletter on Protein Crystallography* (1992) 26; Evans, *Acta Crystallogr. D. Biol. Crystallogr.* (2006) 62:72-82. The $R_{free}$ test set array was copied and extended from the dataset for the 3PE4 coordinates. The refinement process was initiated with 3PE4 coordinates, which was further adjusted by rigid body refinement. After several rounds of refinement in Phenix and modeling in Coot, the crosslink was modeled into the 2Fo-Fc composite omit map. See, e.g., Adams et al., *Acta Crystallogr. D. Biol. Crystallogr.* (2010) 66:213-221; Emsley et al., *Acta Crystallogr. D. Biol. Crystallogr.* (2010) 66:486-501. The complete model was then further refined in Phenix. Chemical restraints for the crosslink were computed using the PRO-DRG2 Server. See, e.g., Schuttelkopf et al., *Acta Crystallogr. D. Biol. Crystallogr.* (2004) 60:1355-1363. These restraints were added as link edits and the model was then refined using Phenix with manual adjustments in Coot. The final $R_{work}$ and $R_{free}$ were of 22.53% and 24.22%, respectively.

Molecular Docking

All molecular docking was done in Schridinger Suite 2010. The protein receptor was prepared in Protein Preparation Wizard using the $hOGT_{4.5}$ crystal structure containing UDP and CKII peptide (PDB 3PE4): all water molecules and ligands were removed and hydrogen atoms were added. The docking grid was calculated in Glide v5.6. See, e.g., Friesner et al., *J. Med. Chem.* (2004) 47:1739-1749; Halgren et al., *J. Med. Chem.* (2004) 47:1750-1759. The rectangular docking grid (20 Å×20 Å×24 Å) was centered using the UDP α-phosphate. Ligands (UDP, UDP-GlcNAc, and BZX compounds) were prepared using Ligprep 2.0 and Epik tools in Glide, at pH 7.0±2.0. Ligands and $hOGT_{4.5}$ were parameterized with the OPLS-2005 force field. All ligands were docked in Glide XP mode. See, e.g., Friesner et al., *J. Med. Chem.* (2006) 49:6177-6196. Molecular docking was conducted independently with 50 different starting poses of each compound. Ligand poses were analyzed in Maestro and Pymol. See, e.g., DeLano, *The Pymol molecular graphics system*, Delano Scientific, San Carlos, Calif., 2002.

Western Blot of BZX-Treated Human Breast Cancer Cells MCF-10A ErbB2 cells were obtained from Joan Brugge's lab at Harvard Medical School (Boston, Mass.). Cells were maintained in DMEM/F12 (Invitrogen) supplemented with 5% horse serum (Invitrogen), 20 ng/ml EGF (Peprotech), 10 μg/ml insulin (Sigma), 100 ng/ml cholera toxin (Sigma), 500 μg/ml hydrocortisone (Sigma), 50 U/ml penicillin and 50 μg/ml streptomycin (Invitrogen). When cells were grown to 70% confluence, old growth medium was removed. Cells were rinsed twice with PBS, and were grown in glucose starvation medium (DMEM-no glucose; Invitrogen) supplemented with 1% horse serum, 50 U/ml penicillin and 50 μg/ml streptomycin) in the absence (control) and presence of (2) (200 μM) for 4 h. PUGNAc (100 μM, Sigma) and glucosamine (2 mM, EMD) were added to the cells and incubated for another 3 h. Cell lysates from 2–5×10⁶ cells were prepared in M-PER mammalian protein extraction reagent (Pierce) supplemented with protease inhibitor cocktail (Sigma). Lysates were cleared by centrifugation at 16,000 g for 10 min at 4° C. and analyzed by SDS-PAGE. Proteins were transferred to a nitrocellulose membrane (Bio-Rad Laboratories) and O-GlcNAcylation was detected with anti-O-GlcNAc antibody (CTD 110.6, Sigma, used at 1:5,000) and a secondary anti-mouse IgM-HRP antibody (Pierce, used at 1:20,000).

Western Blot of BZX Inhibitor Treated Cell Lysates

MCF-100A ErbB2 cells were maintained in DMEM/F12 (Invitrogen) supplemented with 5% horse serum (Invitrogen), 20 ng/ml EGF (Peprotech), 10 μg/ml insulin (Sigma), 100 ng/ml cholera toxin (Sigma), 500 μg/ml hydrocortisone (Sigma), 50 U/ml penicillin, and 50 μg/ml streptomycin (Invitrogen) to reach 70% confluence. The cells were then grown for another 9 hours in glucose starvation medium (DMEM-no glucose (Invitrogen) supplemented with 1% horse serum, 50 U/ml penicillin and 50 μg/ml streptomycin) before harvest. The cell lysates, prepared as described above, were divided into four tubes with each tube containing the same amount of protein. Nothing was added to tube I; OGT (2 µM) and DMSO (1%) were added into tube II; OGT (2 µM) and (2) (200 µM) were added to tube III; OGT (2 µM) and 1 (200 µM) were added to tube IV. The four samples were incubated at room temperature for 30 min before adding UDP-GlcNAc (1 mM) and incubated for another 2 hours. After incubation, all samples were analyzed with SDS-PAGE and a Western blot was carried out using the anti-O-GlcNAc antibody as described above.

Kinase Screen

Kinase profiling was conducted using Invitrogen Z'-LYTE screening protocol and assay conditions found at www.invitrogen.com. Compound (2) inhibited PLK1 completely at 5 µM.

In some embodiments, other compounds of Formula (I) may inhibit PLK1 and/or other kinases. In some embodiments, provided compounds do not inhibit one, more than one, or any of the following kinases: ABL1, ADRBK1 (GRK2), Aurora A, CDK5/p25, CSK, EEF2K, EPHA1, FER, FGR, FLT3 D835Y, GRK4, HIPK2, IKBKE (IKK epsilon), MAPK12 (p38 gamma), MAPKAPK5 (PRAK), MARK2, MET M1250T, MST1R(RON), NEK6, PHKG2, PRKD1 (PKC mu), PRKX, RET, RPS6KA2 (RSK3), SGKL (SGK3), SRPK2.

TABLE 2

Kinase profiling of Compound (2)

| Kinase Tested | % Inhibition Point 1 | % Inhibition Point 2 | mean |
|---|---|---|---|
| ABL1 | −147 | −234 | −190 |
| ADRBK1 (GRK2) | 2 | 5 | 4 |
| AURKA (Aurora A) | −146 | −146 | −146 |
| CDK5/p25 | −322 | −286 | −304 |
| CSK | −42 | −60 | −51 |
| EEF2K | −64 | −61 | −63 |
| EPHA1 | −62 | −107 | −85 |
| FER | −261 | −240 | −251 |
| FGR | 21 | 21 | 21 |
| FLT3 D835Y | −41 | −43 | −42 |
| GRK4 | 77 | 76 | 76 |
| HIPK2 | −96 | −90 | −93 |
| IKBKE (IKK epsilon) | 3 | 4 | 3 |
| MAPK12 (p38 gamma) | −203 | −203 | −203 |
| MAPKAPK5 (PRAK) | −146 | −147 | −146 |
| MARK2 | −172 | −157 | −164 |
| MET M1250T | −113 | −143 | −128 |
| MST1R (RON) | −258 | −245 | −252 |
| NEK6 | −490 | −457 | −474 |
| PHKG2 | −360 | −308 | −334 |
| PLK1 | 104 | 104 | 104 |
| PRKD1 (PKC mu) | −137 | −151 | −144 |
| PRKX | −135 | −134 | −135 |
| RET | −91 | −70 | −80 |
| RPS6KA2 (RSK3) | −266 | −267 | −267 |
| SGKL (SGK3) | −140 | −150 | −145 |
| SRPK2 | −155 | −160 | −158 |

A further kinase screen was performed on Compounds (2), (4A), and (4B) using the assay described above.

In some embodiments, provided compounds do not inhibit one, more than one, or any of the following kinases: ADRBK1 (GRK2), CAMK2A (CaMKII alpha), CAMK4 (CaMKIV), CDK2/cyclin A, CSNK1G3 (CK1 gamma 3), GRK6, GSK3B (GSK3 beta), JAK3, MAPKAPK2, MARK3, RPS6KA3 (RSK2), RPS6KA5 (MSK1), RPS6KB1 (p70S6K), SGK (SGK1), SRPK1, SYK, and TYK2.

TABLE 3

Kinase profiling of Compounds (2), (4A), and (4B)

| Compound | Kinase Tested | % Inhibition Point 1 | % Inhibition Point 2 | % Inhibition mean |
|---|---|---|---|---|
| 4A | ADRBK1 (GRK2) | 3 | 7 | 5 |
| 4A | CAMK2A (CaMKII alpha) | 20 | 24 | 22 |
| 4A | CAMK4 (CaMKIV) | 18 | 24 | 21 |
| 4A | CDK2/cyclin A | 9 | 9 | 9 |
| 4A | CSNK1G3 (CK1 gamma 3) | 30 | 31 | 31 |
| 4A | GRK6 | 42 | 43 | 42 |
| 4A | GSK3B (GSK3 beta) | 61 | 60 | 60 |
| 4A | JAK3 | 41 | 30 | 36 |
| 4A | MAPKAPK2 | 48 | 53 | 51 |
| 4A | MARK3 | 8 | 12 | 10 |
| 4A | PLK1 | 70 | 65 | 68 |
| 4A | RPS6KA3 (RSK2) | 55 | 56 | 55 |
| 4A | RPS6KA5 (MSK1) | 35 | 32 | 33 |
| 4A | RPS6KB1 (p70S6K) | 19 | 22 | 21 |
| 4A | SGK (SGK1) | 76 | 75 | 76 |
| 4A | SRPK1 | −6 | 2 | −2 |
| 4A | SYK | 21 | 24 | 23 |
| 4A | TYK2 | 7 | 11 | 9 |
| 4B | ADRBK1 (GRK2) | 7 | 6 | 7 |
| 4B | CAMK2A (CaMKII alpha) | 57 | 55 | 56 |
| 4B | CAMK4 (CaMKIV) | 52 | 46 | 49 |
| 4B | CDK2/cyclin A | −2 | 4 | 1 |
| 4B | CSNK1G3 (CK1 gamma 3) | 51 | 48 | 49 |
| 4B | GRK6 | 71 | 71 | 71 |
| 4B | GSK3B (GSK3 beta) | 92 | 93 | 93 |
| 4B | JAK3 | 65 | 64 | 65 |
| 4B | MAPKAPK2 | 90 | 90 | 90 |
| 4B | MARK3 | 34 | 36 | 35 |
| 4B | PLK1 | 98 | 101 | 100 |
| 4B | RPS6KA3 (RSK2) | 58 | 64 | 61 |
| 4B | RPS6KA5 (MSK1) | 49 | 48 | 49 |
| 4B | RPS6KB1 (p70S6K) | 35 | 44 | 40 |
| 4B | SGK (SGK1) | 72 | 73 | 73 |
| 4B | SRPK1 | 0 | 2 | 1 |
| 4B | SYK | 58 | 54 | 56 |
| 4B | TYK2 | 17 | 21 | 19 |
| 2 | ADRBK1 (GRK2) | 4 | 7 | 5 |
| 2 | CAMK2A (CaMKII alpha) | −14 | −10 | −12 |
| 2 | CAMK4 (CaMKIV) | −159 | −201 | −180 |
| 2 | CDK2/cyclin A | −297 | −301 | −299 |
| 2 | CSNK1G3 (CK1 gamma 3) | 13 | 16 | 14 |
| 2 | GRK6 | 14 | 17 | 16 |
| 2 | GSK3B (GSK3 beta) | −7 | 0 | −4 |
| 2 | JAK3 | −90 | −83 | −86 |
| 2 | MAPKAPK2 | 0 | −10 | −5 |
| 2 | MARK3 | −515 | −514 | −514 |
| 2 | PLK1 | 101 | 101 | 101 |
| 2 | RPS6KA3 (RSK2) | −200 | −212 | −206 |
| 2 | RPS6KA5 (MSK1) | −215 | −231 | −223 |
| 2 | RPS6KB1 (p70S6K) | −138 | −122 | −130 |
| 2 | SGK (SGK1) | −234 | −237 | −236 |
| 2 | SRPK1 | −49 | −38 | −44 |
| 2 | SYK | 4 | −4 | 0 |
| 2 | TYK2 | −98 | −99 | −99 |

OTHER EMBODIMENTS

The foregoing has been a description of certain non-limiting embodiments of the invention. Those of ordinary skill in the art will appreciate that various changes and modifications to this description may be made without departing from the spirit or scope of the present invention, as defined in the following claims.

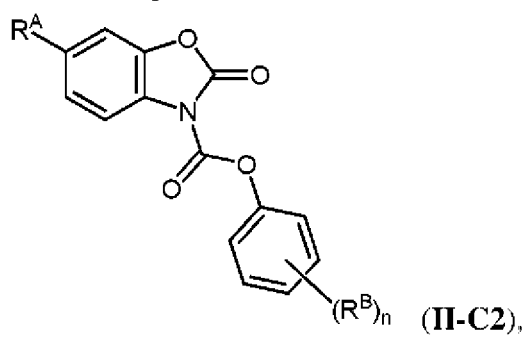
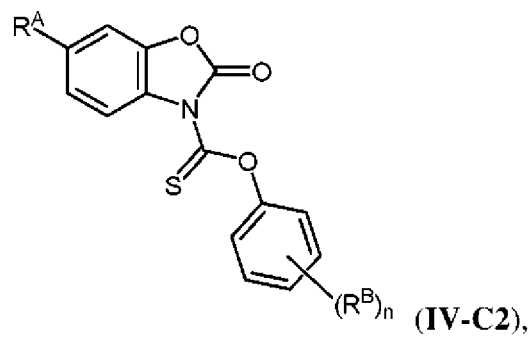
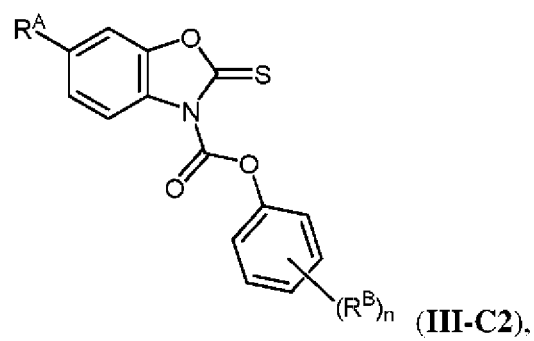
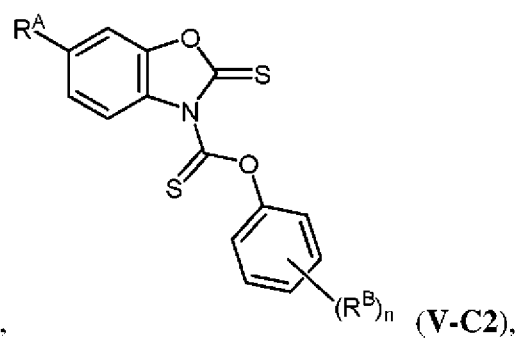

What is claimed is:

1. A compound of Formula (I-i):

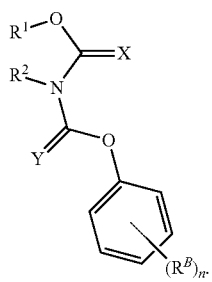

or a pharmaceutically acceptable salt thereof;
wherein:
X is O or S;
Y is O or S;
$R^1$ and $R^2$ are taken together to form a 5-membered oxazolidin-2-one ring or a 6-membered 1,3-oxazinan-2-one ring, wherein the ring is optionally substituted or fused to an optionally substituted carbocyclyl, optionally substituted heterocyclyl, optionally substituted aryl, or optionally substituted heteroaryl ring;
each instance of $R^B$ is independently selected from the group consisting of halogen, optionally substituted alkenyl, optionally substituted alkynyl, optionally substituted carbocyclyl, optionally substituted heterocyclyl, optionally substituted aryl, optionally substituted heteroaryl, —$OR^{B1}$, —$N(R^{B2})_2$, —$SR^{B1}$, —$C(=O)R^{B1}$, —$C(=O)OR^{B1}$, —$C(=O)SR^{B1}$, —$C(=O)N(R^{B2})_2$, —$OC(=O)R^{B1}$, —$OC(=O)OR^{B1}$, —$OC(=O)SR^{B1}$, —$OC(=O)N(R^{B2})_2$, —$NR^{B2}C(=O)R^{B2}$, —$NR^{B2}C(=O)OR^{B1}$, —$NR^{B2}C(=O)SR^{B1}$, —$NR^{B2}C(=O)N(R^{B2})_2$, —$SC(=O)R^{B1}$, —$SC(=O)OR^{B1}$, —$SC(=O)SR^{B1}$, —$SC(=O)N(R^{B2})_2$, —$C(=NR^{B2})R^{B1}$, —$C(=NR^{B2})OR^{B1}$, —$C(=NR^{B2})SR^{B1}$, —$C(=NR^{B2})N(R^{B2})_2$, —$OC(=NR^{B2})R^{B1}$, —$OC(=NR^{B2})OR^{B1}$, —$OC(=NR^{B2})SR^{B1}$, —$OC(=NR^{B2})N(R^{B2})_2$, —$NR^{B2}C(=NR^{B2})R^{B2}$, —$NR^{B2}C(=NR^{B2})OR^{B1}$, —$NR^{B2}C(=NR^{B2})SR^{B1}$, —$NR^{B2}C(=NR^{B2})N(R^{B2})_2$, —$SC(=NR^{B2})R^{B1}$, —$SC(=NR^{B2})OR^{B1}$, —$SC(=NR^{B2})SR^{B1}$, —$SC(=NR^{B2})N(R^{B2})_2$, —$C(=S)R^{B1}$, —$C(=S)OR^{B1}$, —$C(=S)SR^{B1}$, —$C(=S)N(R^{B2})_2$, —$OC(=S)R^{B1}$, —$OC(=S)OR^{B1}$, —$OC(=S)SR^{B1}$, —$OC(=S)N(R^{B2})_2$, —$NR^{B2}C(=S)R^{B2}$, —$NR^{B2}C(=S)OR^{B1}$, —$NR^{B2}C(=S)SR^{B1}$, —$NR^{B2}C(=S)N(R^{B2})_2$, —$SC(=S)R^{B1}$, —$SC(=S)OR^{B1}$, —$SC(=S)SR^{B1}$, —$SC(=S)N(R^{B2})_2$, —$S(=O)R^{B1}$, —$SO_2R^{B1}$, —$NR^{B2}SO_2R^{B1}$, —$SO_2N(R^{B2})_2$, —CN, —SCN, and —$NO_2$;
each occurrence of $R^{B1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{B2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{B2}$ groups are joined to form a heterocyclic ring; and n is 0, 1, 2, 3, 4, or 5; and provided that the compound is not:

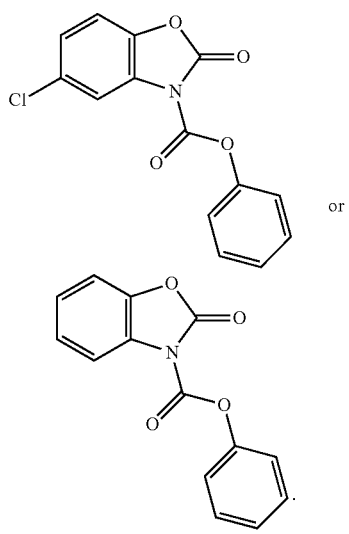

or

2. The compound of claim 1, wherein $R^1$, $R^2$, or the ring formed therefrom, is substituted with at least one substituent selected from the group consisting of —C(=O)$R^{B1}$, —C(=O)O$R^{B1}$, —C(=O)S$R^{B1}$, —C(=O)N($R^{B2}$)$_2$, —OC(=O)$R^{B1}$, —OC(=O)O$R^{B1}$, —OC(=O)S$R^{B1}$, —OC(=O)N($R^{B2}$)$_2$, —NR$^{B2}$C(=O)$R^{B2}$, —NR$^{B2}$C(=O)O$R^{B1}$, —NR$^{B2}$C(=O)S$R^{B1}$, —NR$^{B2}$C(=O)N($R^{B2}$)$_2$, —SC(=O)$R^{B1}$, —SC(=O)O$R^{B1}$, —SC(=O)S$R^{B1}$, —SC(=O)N($R^{B2}$)$_2$, —C(=NR$^{B2}$)$R^{B1}$, —C(=NR$^{B2}$)O$R^{B1}$, —C(=NR$^{B2}$)S$R^{B1}$, —C(=NR$^{B2}$)N($R^{B2}$)$_2$, —OC(=NR$^{B2}$)$R^{B1}$, —OC(=NR$^{B2}$)O$R^{B1}$, —OC(=NR$^{B2}$)S$R^{B1}$, —OC(=NR$^{B2}$)N($R^{B2}$)$_2$, —NR$^{B2}$C(=NR$^{B2}$)$R^{B2}$, —NR$^{B2}$C(=NR$^{B2}$)O$R^{B1}$, —NR$^{B2}$C(=NR$^{B2}$)S$R^{B1}$, —NR$^{B2}$C(=NR$^{B2}$)N($R^{B2}$)$_2$, —SC(=NR$^{B2}$)$R^{B1}$, —SC(=NR$^{B2}$)O$R^{B1}$, —SC(=NR$^{B2}$)S$R^{B1}$, —SC(=NR$^{B2}$)N($R^{B2}$)$_2$, —C(=S)$R^{B1}$, —C(=S)O$R^{B1}$, —C(=S)S$R^{B1}$, —C(=S)N($R^{B2}$)$_2$, —OC(=S)$R^{B1}$, —OC(=S)O$R^{B1}$, —OC(=S)S$R^{B1}$, —OC(=S)N($R^{B2}$)$_2$, —NR$^{B2}$C(=S)$R^{B2}$, —NR$^{B2}$C(=S)O$R^{B1}$, —NR$^{B2}$C(=S)S$R^{B1}$, —NR$^{B2}$C(=S)N($R^{B2}$)$_2$, —SC(=S)$R^{B1}$, —SC(=S)O$R^{B1}$, —SC(=S)S$R^{B1}$, —SC(=S)N($R^{B2}$)$_2$, —S(=O)$R^{B1}$, —SO$_2$$R^{B1}$, —NR$^{B2}$SO$_2$$R^{B1}$, —SO$_2$N($R^{B2}$)$_2$, —CN, —SCN, and —NO$_2$, wherein each occurrence of $R^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{A2}$ groups are joined to form an optionally substituted heterocyclic ring.

3. The compound of claim 1, wherein $R^1$ and $R^2$ are taken together to form a 5-membered oxazolidin-2-one ring, wherein the ring is optionally substituted or fused to an optionally substituted carbocyclyl, optionally substituted heterocyclyl, optionally substituted aryl, or optionally substituted heteroaryl ring.

4. The compound of claim 1, wherein the compound is of Formula (II-B), (III-B), (IV-B), or (V-B):

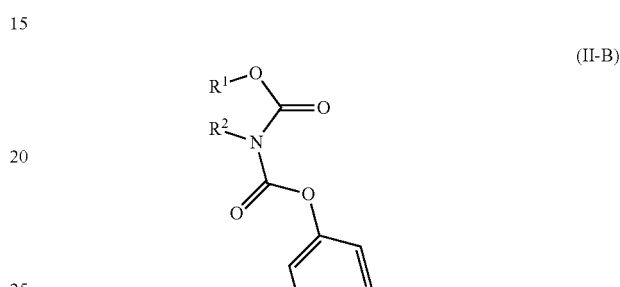

(II-B)

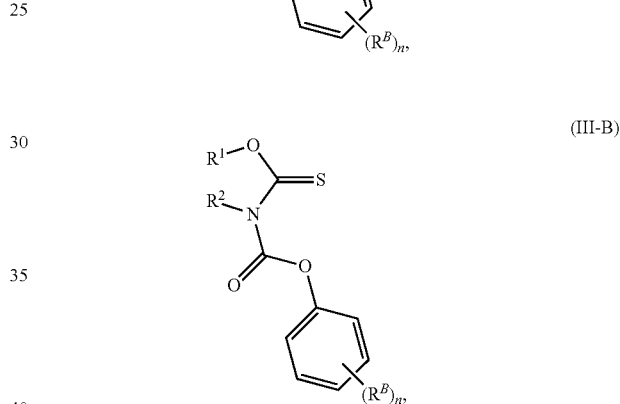

(III-B)

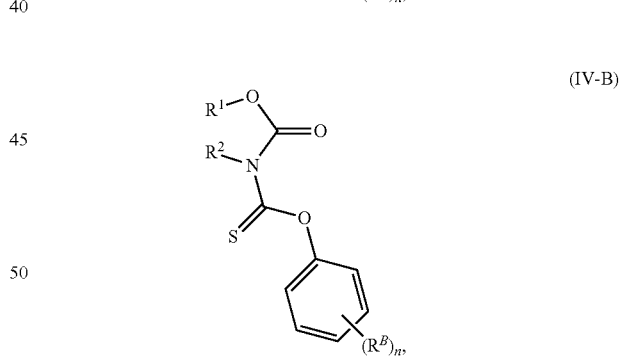

(IV-B)

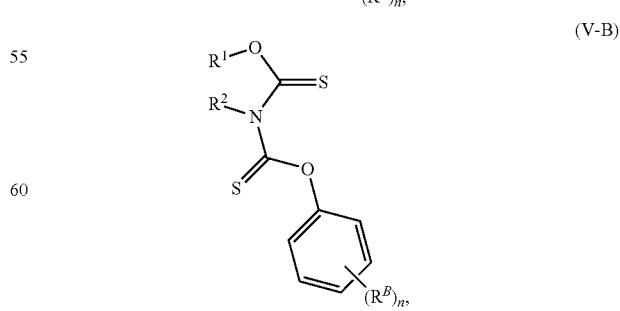

(V-B)

or a pharmaceutically acceptable salt thereof.

5. The compound of claim 1, wherein the compound is of Formula (II-C), (III-C), (IV-C), or (V-C):

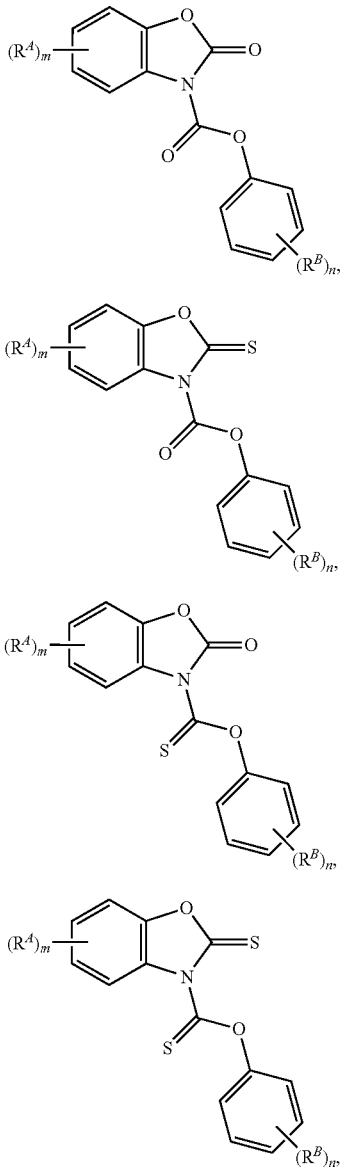

or a pharmaceutically acceptable salt thereof, wherein:

each instance of $R^A$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —$N(R^{A2})_2$, —$SR^{A1}$, —$C(=O)R^{A1}$, —$C(=O)OR^{A1}$, —$C(=O)SR^{A1}$, —$C(=O)N(R^{A2})_2$, —$OC(=O)R^{A1}$, —$OC(=O)OR^{A1}$, —$OC(=O)SR^{A1}$, —$OC(=O)N(R^{A2})_2$, —$NR^{A2}C(=O)R^{A2}$, —$NR^{A2}C(=O)OR^{A1}$, —$NR^{A2}C(=O)SR^{A1}$, —$NR^{A2}C(=O)N(R^{A2})_2$, —$SC(=O)R^{A1}$, —$SC(=O)OR^{A1}$, —$SC(=O)SR^{A1}$, —$SC(=O)N(R^{A2})_2$, —$C(=NR^{A2})R^{A1}$, —$C(=NR^{A2})OR^{A1}$, —$C(=NR^{A2})SR^{A1}$, —$C(=NR^{A2})N(R^{A2})_2$, —$OC(=NR^{A2})R^{A1}$, —$OC(=NR^{A2})OR^{A1}$, —$OC(=NR^{A2})SR^{A1}$, —$OC(=NR)N(R^{A2})_2$, —$NR^{A2}C(=NR^{A2})R^{A2}$, —$NR^{A2}C(=NR^{A2})OR^{A1}$, —$NR^{A2}C(=NR^{A2})SR^{A1}$, —$NR^{A2}C(=NR^{A2})N(R^{A2})_2$, —$SC(=NR^{A2})R^{A1}$, —$SC(=NR^{A2})OR^{A1}$, —$SC(=NR^{A2})SR^{A1}$, —$SC(=NR^{A2})N(R^{A2})_2$, —$C(=S)R^{A1}$, —$C(=S)OR^{A1}$, —$C(=S)SR^{A1}$, —$C(=S)N(R^{A2})_2$, —$OC(=S)R^{A1}$, —$OC(=S)OR^{A1}$, —$OC(=S)SR^{A1}$, —$OC(=S)N(R^{A2})_2$, —$NR^{A2}C(=S)R^{A2}$, —$NR^{A2}C(=S)OR^{A1}$, —$NR^{A2}C(=S)SR^{A1}$, —$NR^{A2}C(=S)N(R^{A2})_2$, —$SC(=S)R^{A1}$, —$SC(=S)OR^{A1}$, —$SC(=S)SR^{A1}$, —$SC(=S)N(R^{A2})_2$, —$S(=O)R^{A1}$, —$SO_2R^{A1}$, —$NR^{A2}SO_2R^{A1}$, —$SO_2N(R^{A2})_2$, —CN, —SCN, and —$NO_2$;

each occurrence of $R^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{A2}$ groups are joined to form an optionally substituted heterocyclic ring; and m is 0, 1, 2, 3, or 4.

6. The compound of claim 5, wherein at least one $R^A$ substituent is selected from the group consisting of —$C(=O)R^{B1}$, —$C(=O)OR^{B1}$, —$C(=O)SR^{B1}$, —$C(=O)N(R^{B2})_2$, —$OC(=O)R^{B1}$, —$OC(=O)OR^{B1}$, —$OC(=O)SR^{B1}$, —$OC(=O)N(R^{B2})_2$, —$NR^{B2}C(=O)R^{B2}$, —$NR^{B2}C(=O)OR^{B1}$, —$NR^{B2}C(=O)SR^{B1}$, —$NR^{B2}C(=O)N(R^{B2})_2$, —$SC(=O)R^{B1}$, —$SC(=O)OR^{B1}$, —$SC(=O)SR^{B1}$, —$SC(=O)N(R^{B2})_2$, —$C(=NR^{B2})R^{B1}$, —$C(=NR^{B2})OR^{B1}$, —$C(=NR^{B2})SR^{B1}$, —$C(=NR^{B2})N(R^{B2})_2$, —$OC(=NR^{B2})R^{B1}$, —$OC(=NR^{B2})OR^{B1}$, —$OC(=NR^{B2})SR^{B1}$, —$OC(=NR^{B2})N(R^{B2})_2$, —$NR^{B2}C(=NR^{B2})R^{B2}$, —$NR^{B2}C(=NR^{B2})OR^{B1}$, —$NR^{B2}C(=NR^{B2})SR^{B1}$, —$NR^{B2}C(=NR^{B2})N(R^{B2})_2$, —$SC(=NR^{B2})R^{B1}$, —$SC(=NR^{B2})OR^{B1}$, —$SC(=NR^{B2})SR^{B1}$, —$SC(=NR^{B2})N(R^{B2})_2$, —$C(=S)R^{B1}$, —$C(=S)OR^{B1}$, —$C(=S)SR^{B1}$, —$C(=S)N(R^{B2})_2$, —$OC(=S)R^{B1}$, —$OC(=S)OR^{B1}$, —$OC(=S)SR^{B1}$, —$OC(=S)N(R^{B2})_2$, —$NR^{B2}C(=S)R^{B2}$, —$NR^{B2}C(=S)OR^{B1}$, —$NR^{B2}C(=S)SR^{B1}$, —$NR^{B2}C(=S)N(R^{B2})_2$, —$SC(=S)R^{B1}$, —$SC(=S)OR^{B1}$, —$SC(=S)SR^{B1}$, —$SC(=S)N(R^{B2})_2$, —$S(=O)R^{B1}$, —$SO_2R^{B1}$, —$NR^{B2}SO_2R^{B1}$, —$SO_2N(R^{B2})_2$, —CN, —SCN, and —$NO_2$.

7. The compound of claim 5, wherein at least one $R^B$ substituent is selected from the group consisting of —$OR^{B1}$, —$N(R^{B2})_2$, and —$SR^{B1}$, wherein each occurrence of $R^{B1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{B2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{B2}$ groups are joined to form a heterocyclic ring.

8. The compound of claim 5, wherein the compound is of Formula (II-C7), (III-C7), (IV-C7), or (V-C7):
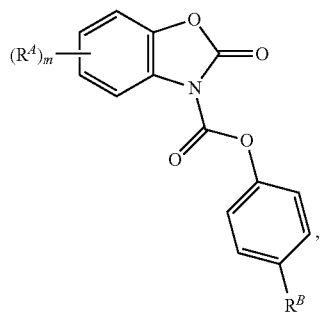
(II-C7)
(III-C7)
(IV-C7)
(V-C7)
or a pharmaceutically acceptable salt thereof.
9. The compound of claim 5, wherein the compound is of Formula (II-C2), (III-C2), (IV-C2), or (V-C2):
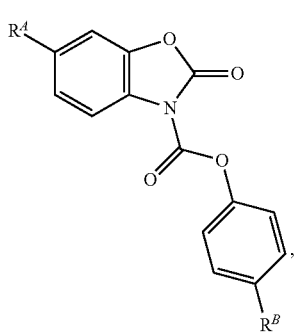
(II-C17)
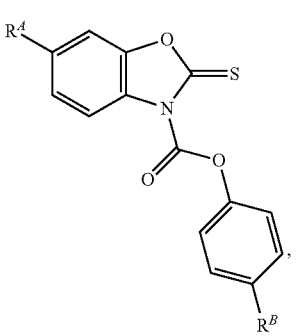
(III-C17)
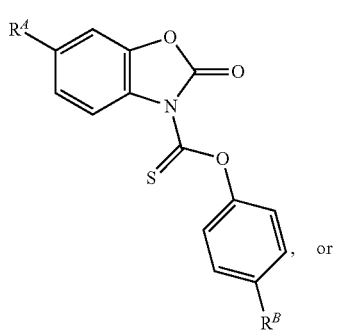
(IV-C17), or
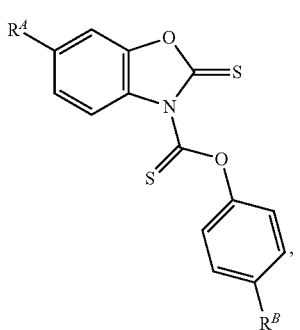
(V-C17)
or a pharmaceutically acceptable salt thereof.

10. The compound of claim 5, wherein the compound is of Formula (II-C17), (III-C17), (IV-C17), or (V-C17):
11. The compound of claim 5, wherein the compound is of Formula (II-C22), (III-C22), (IV-C22), or (V-C22):
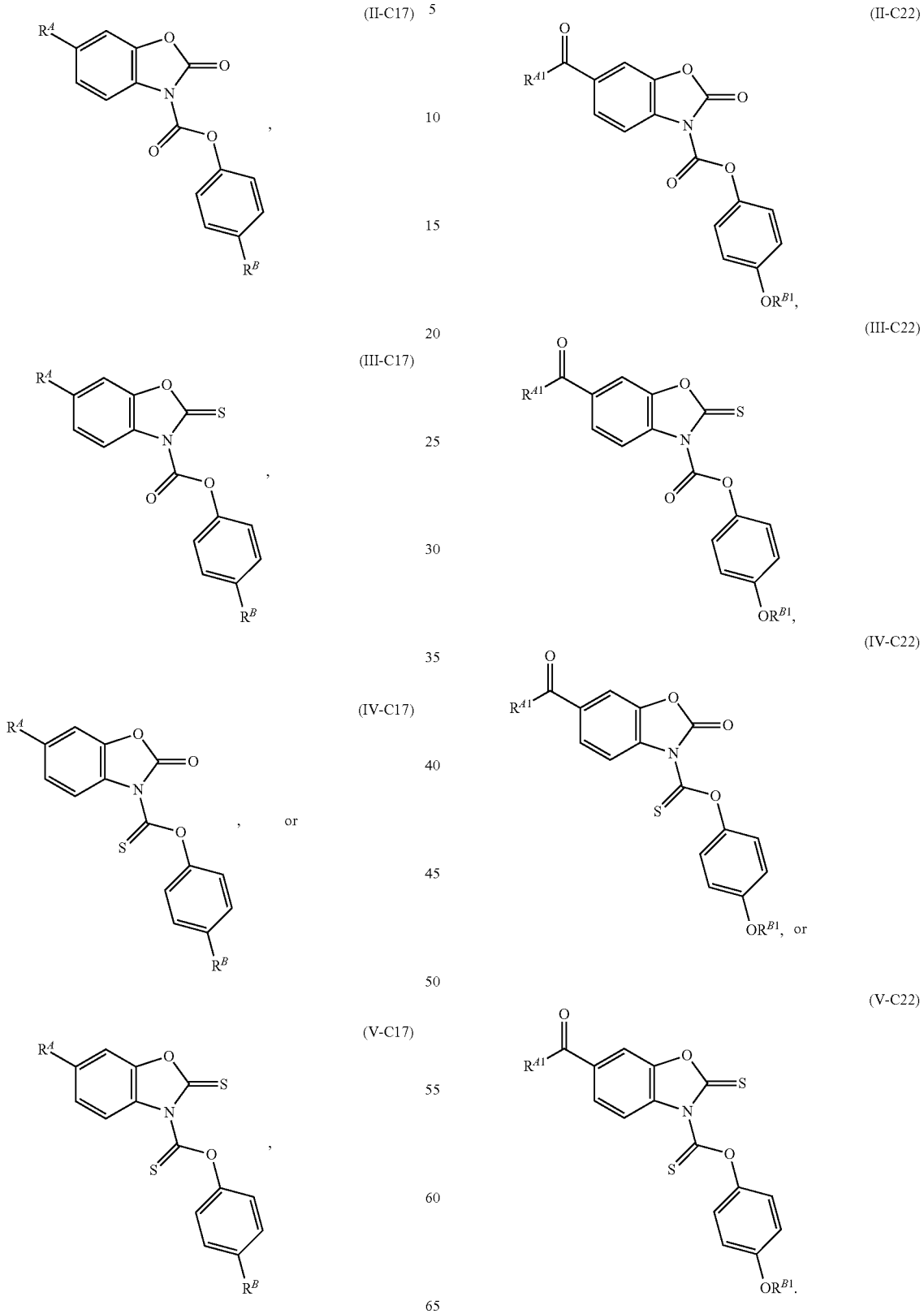
or a pharmaceutically acceptable salt thereof.
or a pharmaceutically acceptable salt thereof.

12. The compound of claim 1, wherein the compound is selected from the group consisting of:

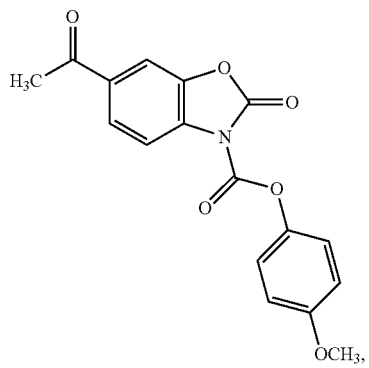

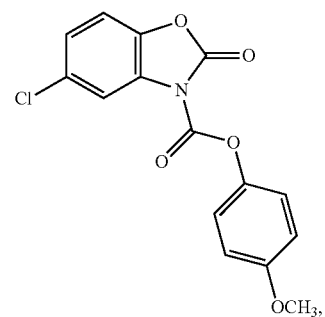

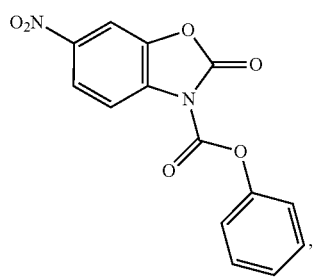

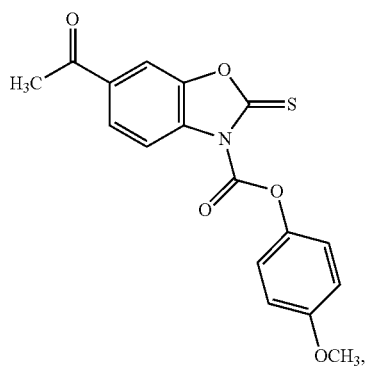 [SMILES: COc1ccc(OC(=S)n2c(=O)oc3cc(C(C)=O)ccc32)cc1]

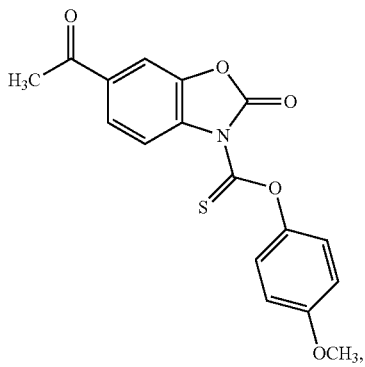

and pharmaceutically acceptable salts thereof.

13. A pharmaceutical composition comprising an effective amount of a compound of claim 1, or a pharmaceutically acceptable salt thereof, and optionally a pharmaceutically acceptable excipient.

14. The compound of claim 1, wherein $R^1$ and $R^2$ are taken together to form a 5-membered oxazolidin-2-one ring.

15. The compound of claim 1, wherein the compound is of Formula (II-B), (III-B), or (IV-B):

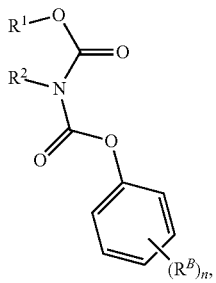
(II-B)

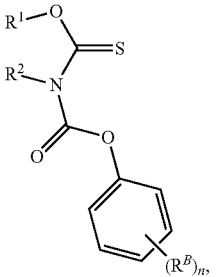
(III-B)

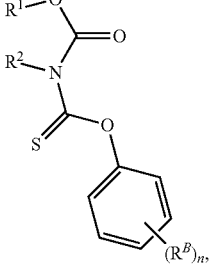
(IV-B)

or a pharmaceutically acceptable salt thereof.

16. The compound of claim 1, wherein the compound is of Formula (II-C), (III-C), or (IV-C):

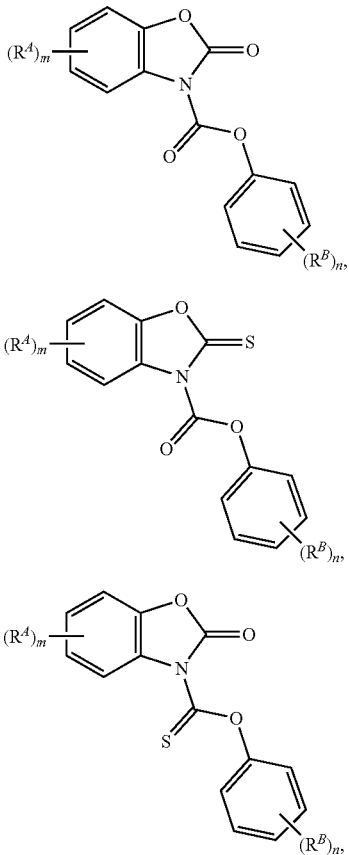

or a pharmaceutically acceptable salt thereof, wherein:

each instance of $R^A$ is independently selected from the group consisting of halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —$N(R^{A2})_2$, —$SR^{A1}$, —$C(=O)R^{A1}$, —$C(=O)OR^{A1}$, —$C(=O)SR^{A1}$, —$C(=O)N(R^{A2})_2$, —$OC(=O)R^{A1}$, —$OC(=O)OR^{A1}$, —$OC(=O)SR^{A1}$, —$OC(=O)N(R^{A2})_2$, —$NR^{A2}C(=O)R^{A2}$, —$NR^{A2}C(=O)OR^{A1}$, —$NR^{A2}C(=O)SR^{A1}$, —$NR^{A2}C(=O)N(R^{A2})_2$, —$SC(=O)R^{A1}$, —$SC(=O)OR^{A1}$, —$SC(=O)SR^{A1}$, —$SC(=O)N(R^{A2})_2$, —$C(=NR^{A2})R^{A1}$, —$C(=NR)OR^{A1}$, —$C(=NR)SR^{A1}$, —$C(=NR^{A2})N(R^{A2})_2$, —$OC(=NR^{A2})R^{A1}$, —$OC(=NR^{A2})OR^{A1}$, —$OC(=NR)SR^{A1}$, —$OC(=NR)N(R^{A2})_2$, —$NR^{A2}C(=NR^{A2})R^{A2}$, —$NR^{A2}C(=NR^{A2})OR^{A1}$, —$NR^{A2}C(=NR^{A2})SR^{A1}$, —$NR^{A2}C(=NR^{A2})N(R^{A2})_2$, —$SC(=NR^{A2})R^{A1}$, —$SC(=NR^{A2})OR^{A1}$, —$SC(=NR^{A2})SR^{A1}$, —$SC(=NR^{A2})N(R^{A2})_2$, —$C(=S)R^{A1}$, —$C(=S)OR^{A1}$, —$C(=S)SR^{A1}$, —$C(=S)N(R^{A2})_2$, —$OC(=S)R^{A1}$, —$OC(=S)OR^{A1}$, —$OC(=S)SR^{A1}$, —$OC(=S)N(R^{A2})_2$, —$NR^{A2}C(=S)R^{A2}$, —$NR^{A2}C(=S)OR^{A1}$, —$NR^{A2}C(=S)SR^{A1}$, —$NR^{A2}C(=S)N(R^{A2})_2$, —$SC(=S)R^{A1}$, —$SC(=S)OR^{A1}$, —$SC(=S)SR^{A1}$, —$SC(=S)N(R^{A2})_2$, —$S(=O)R^{A1}$, —$SO_2R^{A1}$, —$NR^{A2}SO_2R^{A1}$, —$SO_2N(R^{A2})_2$, —CN, —SCN, and —$NO_2$;

each occurrence of $R^{A1}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^{A2}$ groups are joined to form an optionally substituted heterocyclic ring; and m is 0, 1, 2, 3, or 4.

17. The compound of claim 5, wherein:

at least one instance of $R^A$ is: halogen, —$OR^{A1}$, —$N(R^{A2})_2$, —$C(=O)R^{A1}$, or —$NO_2$;

at least one instance of $R^{A1}$ is optionally substituted alkyl; and at least one instance of $R^{A2}$ is optionally substituted alkyl.

18. The compound of claim 16, wherein:

at least one instance of $R^A$ is: halogen, —$OR^{A1}$, —$N(R^{A2})_2$, —$C(=O)R^{A1}$, or —$NO_2$;

at least one instance of $R^{A1}$ is optionally substituted alkyl; and at least one instance of $R^{A2}$ is optionally substituted alkyl.

19. The compound of claim 5, wherein at least one instance of $R^B$ is —$OR^{B1}$.

20. The compound of claim 16, wherein at least one instance of $R^B$ is —$OR^{B1}$.

21. The compound of claim 1, wherein the compound is selected from the group consisting of:

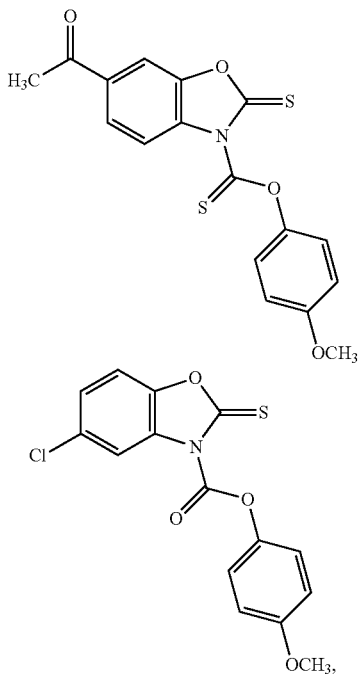

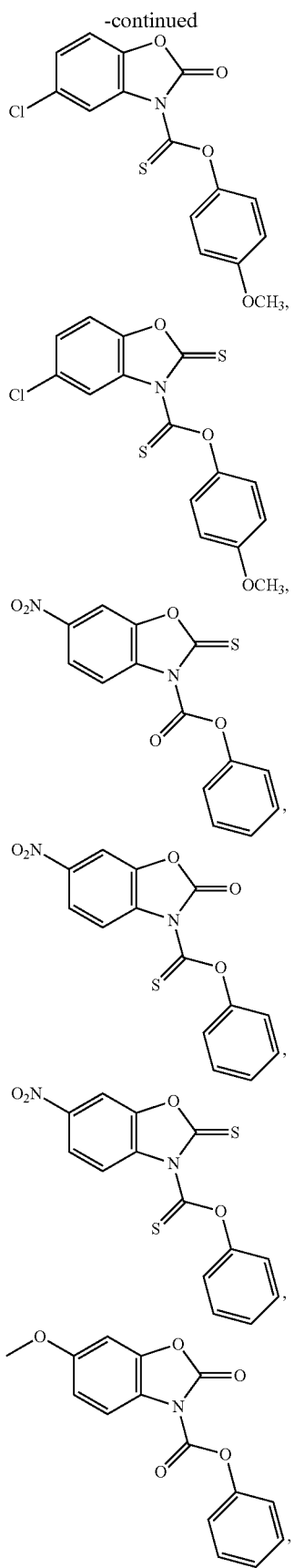
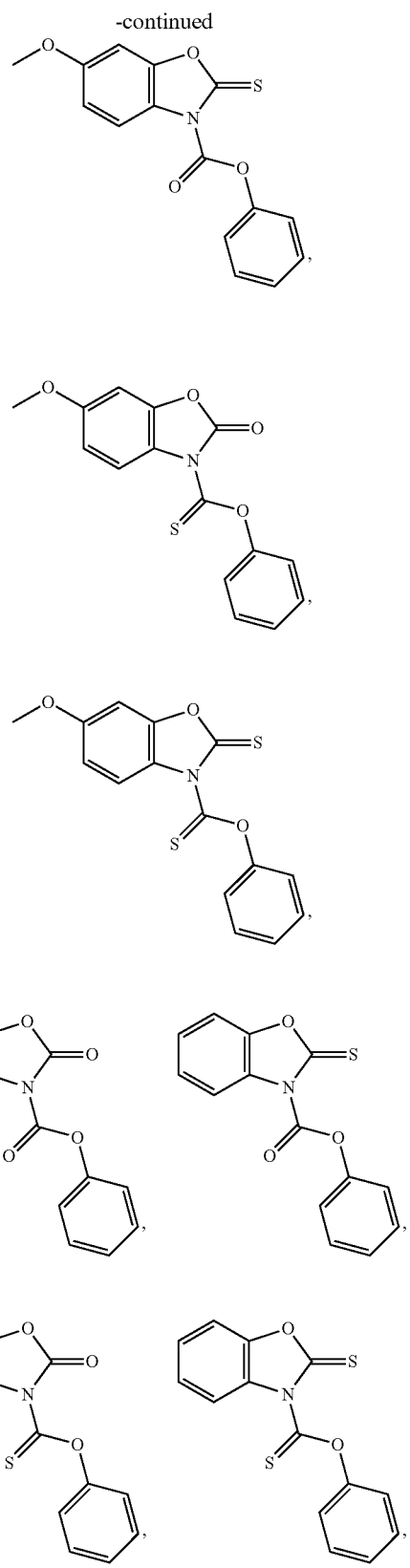
and pharmaceutically acceptable salts thereof.
* * * * *

UNITED STATES PATENT AND TRADEMARK OFFICE
CERTIFICATE OF CORRECTION

PATENT NO. : 9,573,911 B2
APPLICATION NO. : 14/131024
DATED : February 21, 2017
INVENTOR(S) : Suzanne Walker Kahne et al.

It is certified that error appears in the above-identified patent and that said Letters Patent is hereby corrected as shown below:

In the Claims

In Claim 1, at Column 127, Lines 41-54, formula:

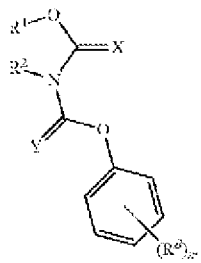

Should be replaced with the formula:

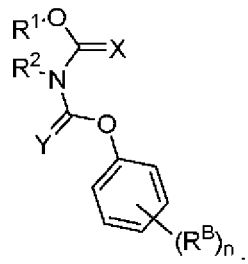

Signed and Sealed this
Twentieth Day of June, 2017

Joseph Matal
*Performing the Functions and Duties of the
Under Secretary of Commerce for Intellectual Property and
Director of the United States Patent and Trademark Office*

In Claim 8, at Column 133, Lines 5-65, the following formulae:
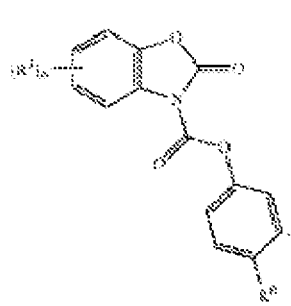
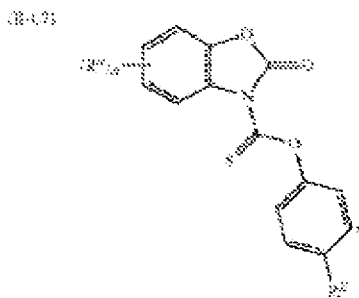
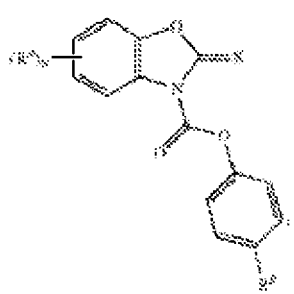
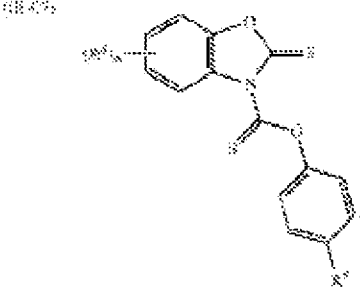
Should be replaced with the formulae:
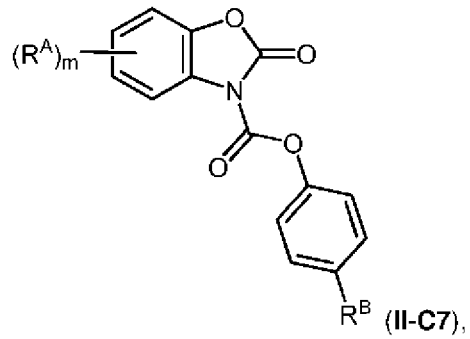
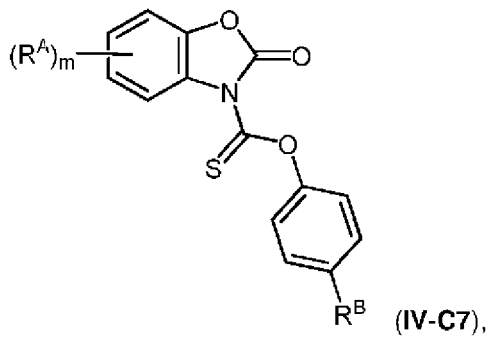
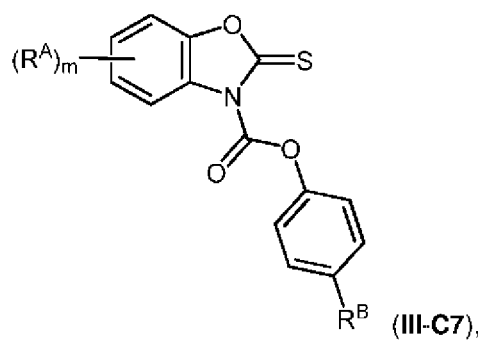
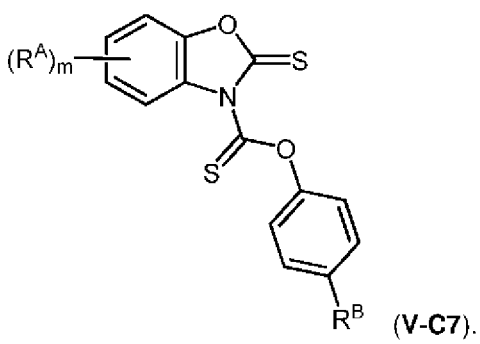

CERTIFICATE OF CORRECTION (continued)
U.S. Pat. No. 9,573,911 B2

In Claim 9, at Column 134, Lines 5-65, the following formulae:

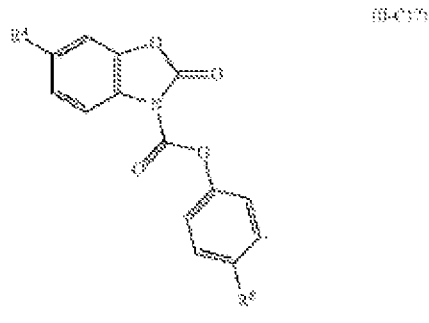
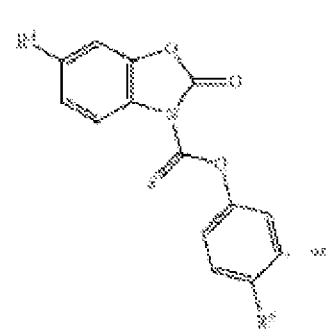
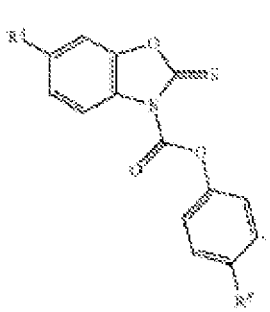
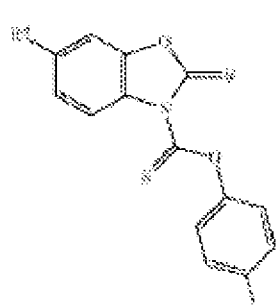

Should be replaced with the formulae:

SEQUENCE LISTING

<160> NUMBER OF SEQ ID NOS: 10

<210> SEQ ID NO 1
<211> LENGTH: 40
<212> TYPE: DNA
<213> ORGANISM: Artificial Sequence
<220> FEATURE:
<223> OTHER INFORMATION: Y841A forward primer

<400> SEQUENCE: 1
ctgcaacttc aaccagctgg ccaaaatcga cccgtctacc           40

<210> SEQ ID NO 2
<211> LENGTH: 40
<212> TYPE: DNA
<213> ORGANISM: Artificial Sequence
<220> FEATURE:
<223> OTHER INFORMATION: Y841A reverse primer

<400> SEQUENCE: 2
ggtagacggg tcgattttgg ccagctggtt gaagttgcag           40

<210> SEQ ID NO 3
<211> LENGTH: 40
<212> TYPE: DNA
<213> ORGANISM: Artificial Sequence
<220> FEATURE:
<223> OTHER INFORMATION: K842A forward primer

<400> SEQUENCE: 3
caacttcaac cagctgtacg caatcgaccc gtctaccctg           40

<210> SEQ ID NO 4
<211> LENGTH: 40
<212> TYPE: DNA
<213> ORGANISM: Artificial Sequence
<220> FEATURE:
<223> OTHER INFORMATION: K842A reverse primer

<400> SEQUENCE: 4
cagggtagac gggtcgattg cgtacagctg gttgaagttg           40

<210> SEQ ID NO 5
<211> LENGTH: 28
<212> TYPE: DNA
<213> ORGANISM: Artificial Sequence
<220> FEATURE:
<223> OTHER INFORMATION: C917A forward primer

<400> SEQUENCE: 5
ggacaccccg ctggccaacg gtcacacc           28

<210> SEQ ID NO 6
<211> LENGTH: 28
<212> TYPE: DNA
<213> ORGANISM: Artificial Sequence
<220> FEATURE:
<223> OTHER INFORMATION: C917A reverse primer

<400> SEQUENCE: 6
ggtgtgaccg ttggccagcg gggtgtcc           28

<210> SEQ ID NO 7
<211> LENGTH: 29
<212> TYPE: DNA
<213> ORGANISM: Artificial Sequence

```
<220> FEATURE:
<223> OTHER INFORMATION: T921A forward primer

<400> SEQUENCE: 7
tgtgcaacgg tcacgccacc ggtatggac                              29

<210> SEQ ID NO 8
<211> LENGTH: 29
<212> TYPE: DNA
<213> ORGANISM: Artificial Sequence
<220> FEATURE:
<223> OTHER INFORMATION: T921A reverse primer

<400> SEQUENCE: 8
gtccataccg gtggcgtgac cgttgcaca                              29

<210> SEQ ID NO 9
<211> LENGTH: 29
<212> TYPE: DNA
<213> ORGANISM: Artificial Sequence
<220> FEATURE:
<223> OTHER INFORMATION: T922A forward primer

<400> SEQUENCE: 9
gcaacggtca caccgccggt atggacgtt                              29

<210> SEQ ID NO 10
<211> LENGTH: 29
<212> TYPE: DNA
<213> ORGANISM: Artificial Sequence
<220> FEATURE:
<223> OTHER INFORMATION: T922A reverse primer

<400> SEQUENCE: 10
aacgtccata ccggcggtgt gaccgttgc                              29
```